(12) United States Patent
Ozaki et al.

(10) Patent No.: US 7,497,996 B2
(45) Date of Patent: Mar. 3, 2009

(54) LIQUID DELIVERY APPARATUS AND LIQUID DELIVERY METHOD

(75) Inventors: Nobuhiko Ozaki, Nara (JP); Hiroaki Oka, Osaka (JP); Tetsuo Yukimasa, Nara (JP); Hidenobu Yaku, Osaka (JP); Maki Yotsuhashi, Osaka (JP); Yukari Hataoka, Osaka (JP)

(73) Assignee: Panasonic Corporation, Osaka (JP)

( * ) Notice: Subject to any disclaimer, the term of this patent is extended or adjusted under 35 U.S.C. 154(b) by 125 days.

(21) Appl. No.: 11/516,008

(22) Filed: Sep. 6, 2006

(65) Prior Publication Data

US 2007/0003437 A1    Jan. 4, 2007

Related U.S. Application Data

(63) Continuation of application No. PCT/JP2005/022164, filed on Dec. 2, 2005.

(30) Foreign Application Priority Data

Jan. 24, 2005    (JP) .............................. 2005-015489

(51) Int. Cl.
    *B01L 3/02*    (2006.01)
(52) U.S. Cl. .......................... 422/100; 435/24; 435/25; 435/32; 435/283.1; 436/180; 422/99; 422/68.1; 422/82.01
(58) Field of Classification Search ........... 422/99–101, 422/68.1, 82.01; 435/32, 283.1, 24–25; 436/180
    See application file for complete search history.

(56) References Cited

U.S. PATENT DOCUMENTS

| | | | |
|---|---|---|---|
| 4,835,106 A | 5/1989 | Johnson et al. | |
| 5,061,381 A | 10/1991 | Burd | |
| 5,160,702 A | 11/1992 | Kopf-Sill et al. | |
| 5,591,643 A | 1/1997 | Schembri | |
| 2004/0259237 A1 | 12/2004 | Kellogg et al. | |

FOREIGN PATENT DOCUMENTS

CA    2053894    12/1990

(Continued)

OTHER PUBLICATIONS

International Preliminary Report on Patentability, issued in corresponding International Application No. PCT/JP2005/022164, dated on Aug. 2, 2007.

*Primary Examiner*—Jill Warden
*Assistant Examiner*—Jyoti Nagpaul
(74) *Attorney, Agent, or Firm*—McDermott Will & Emery LLP

(57) ABSTRACT

A liquid delivery apparatus 1 has a rotary substrate 2. The substrate 2 formed with a fluid passage 8A for communicating a supply chamber 6A and target chamber 7A. An inlet end portion 13 at which the fluid passage 8A is connected to the chamber 6A extends in a clockwise direction R1 of rotational directions of the substrate 2. The inlet end portion 13 holds a liquid 9 in the chamber 6A by a capillary force. The rotation drive unit 4 rotates the substrate 2 so that an inertial force exceeding the capillary force and directed to the clockwise direction R1 acts on the liquid 9 in the inlet end portion 13. Delivery behavior control of microfluid with a high degree of flexibility can be achieved.

13 Claims, 49 Drawing Sheets

FOREIGN PATENT DOCUMENTS

| | | |
|---|---|---|
| CA | 2 082 827 | 12/1991 |
| CA | 2170528 | 3/1995 |
| DE | 691 30 986 T2 | 9/1999 |
| EP | 0 629 580 A2 | 5/1990 |
| JP | 4-507288 | 12/1992 |
| JP | 5-508709 | 2/1993 |
| JP | 9-504732 | 5/1997 |
| JP | 2001-503854 | 3/2001 |
| JP | 2003-502656 | 1/2003 |
| JP | 2005-537911 | 12/2005 |
| WO | WO 90/15321 | 12/1990 |
| WO | WO 91/18656 | 12/1991 |
| WO | WO 93/08893 | 5/1993 |
| WO | WO 95/06870 | 3/1995 |
| WO | WO 98/07019 | 2/1998 |
| WO | WO 00/78455 A1 | 12/2000 |
| WO | WO 03/057369 A1 | 7/2003 |

*Fig.5*

STEP A
```
SOLUTION IS SUPPLIED FROM INLET 11 OF
ROTATION SUBSTRATE 2 INTO CHAMBER 6A
```

STEP A'
```
INLET 11 IS SEALED
```

```
ROTATION DIRECTION IS
CLOCKWISE DIRECTION R1
```

STEP B
```
ROTATION SUBSTRATE 2 IS DRIVEN WITH VELOCITY
CHARACTERISTIC 41 HAVING ACCELERATION a1
```

STEP C
```
ROTATION SUBSTRATE 2 IS STOPPED WITH VELOCITY
CHARACTERISTIC 42 HAVING ACCELERATION a2
(a2≫a1)
```

$\alpha 1$

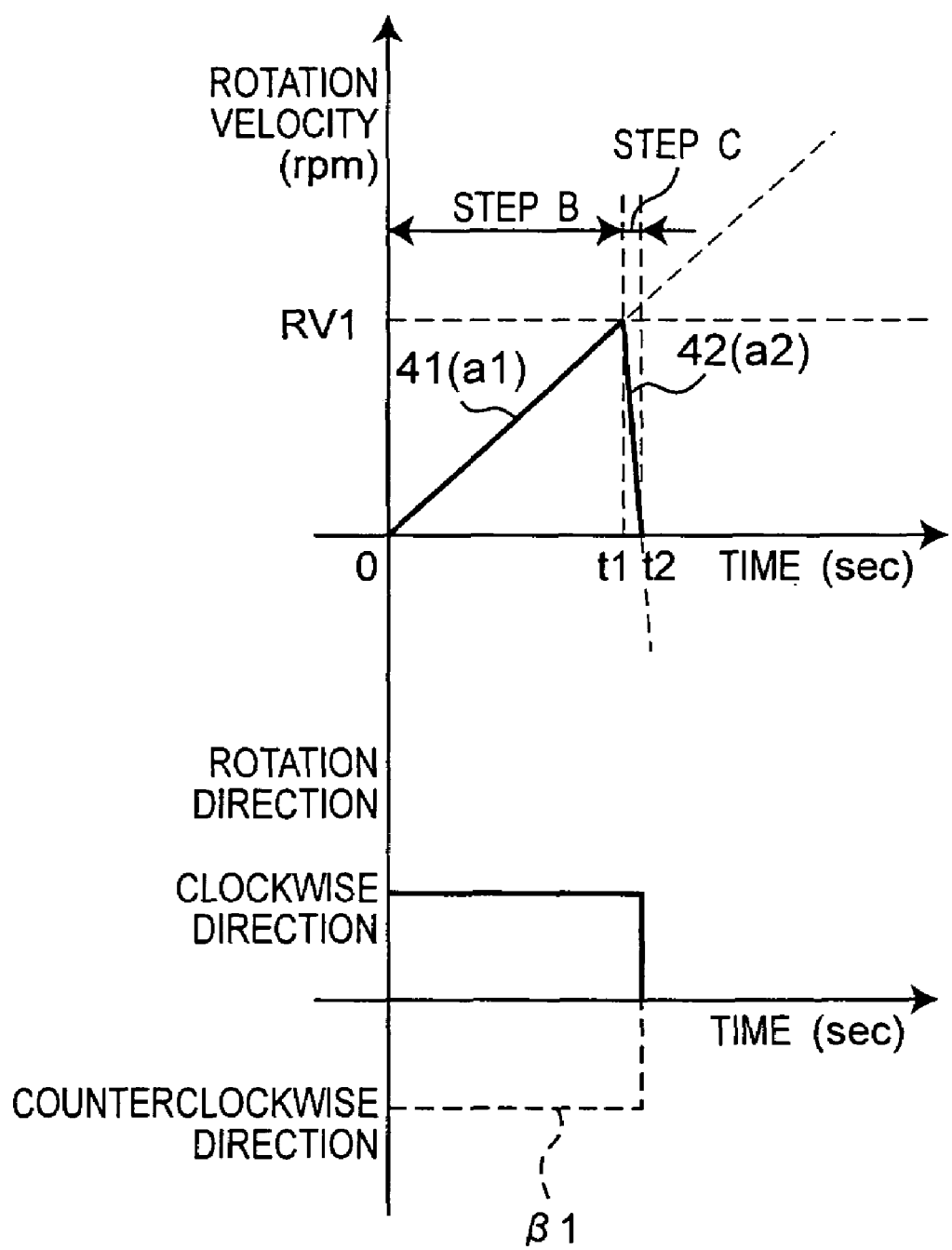

Fig.8

STEP A
SOLUTION IS SUPPLIED FROM INLET 11 OF
ROTATION SUBSTRATE 2 INTO CHAMBER 6A

STEP A'
INLET 11 IS SEALED

ROTATION DIRECTION IS
CLOCKWISE DIRECTION R1

STEP B
ROTATION SUBSTRATE 2 IS DRIVEN WITH VELOCITY
CHARACTERISTIC 41 HAVING ACCELERATION a1

STEP D
ROTATION SUBSTRATE 2 IS DRIVEN
WITH CONSTANT REVOLUTION RV1

STEP C
ROTATION SUBSTRATE 2 IS STOPPED WITH VELOCITY
CHARACTERISTIC 42 HAVING ACCELERATION a2
(a2≫a1)

α2

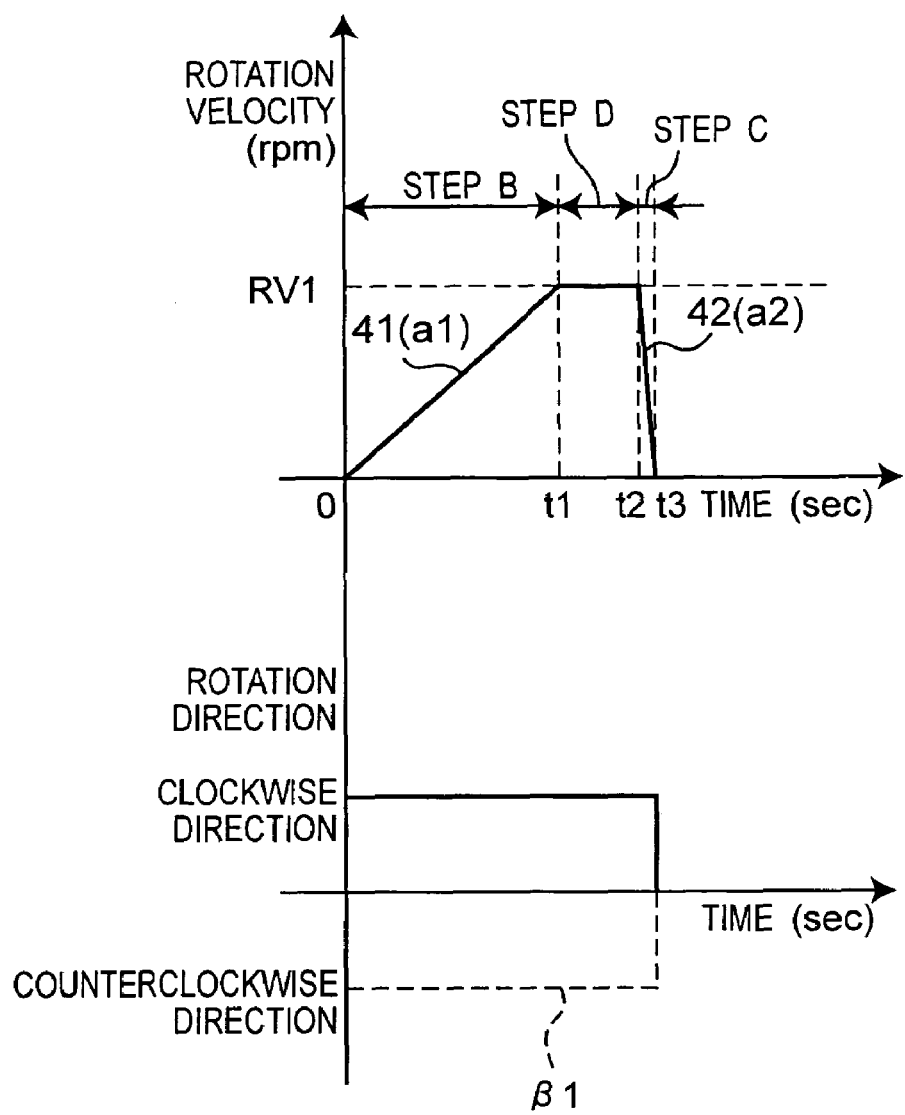

Fig.14

STEP A
SOLUTION IS SUPPLIED FROM INLET 11 OF ROTATION SUBSTRATE 2 INTO CHAMBER 6A

STEP A'
INLET 11 IS SEALED

ROTATION DIRECTION IS CLOCKWISE DIRECTION R1

STEP B
ROTATION SUBSTRATE 2 IS DRIVEN WITH VELOCITY CHARACTERISTIC 41 HAVING ACCELERATION a1

STEP D
ROTATION SUBSTRATE 2 IS DRIVEN WITH CONSTANT REVOLUTION RV1

STEP C
ROTATION SUBSTRATE 2 IS STOPPED WITH VELOCITY CHARACTERISTIC 42 HAVING ACCELERATION a2 (a2≫a1)

STEP E
ROTATION SUBSTRATE 2 IS MAINTAINED IN A ROTATION STOP STATE

Fig. 19

STEP A
SOLUTION IS SUPPLIED FROM INLET 11 OF ROTATION SUBSTRATE 2 INTO CHAMBER 6A

STEP A'
INLET 11 IS SEALED

ROTATION DIRECTION IS COUNTERCLOCKWISE DIRECTION R2

STEP F
ROTATION SUBSTRATE 2 IS DRIVEN WITH VELOCITY CHARACTERISTIC 43 HAVING ACCELERATION b1

STEP G
ROTATION SUBSTRATE 2 IS STOPPED WITH VELOCITY CHARACTERISTIC 44 HAVING ACCELERATION b2

STEP A
SOLUTION IS SUPPLIED FROM INLET 11 OF ROTATION SUBSTRATE 2 INTO CHAMBER 6A

STEP A'
INLET 11 IS SEALED

ROTATION DIRECTION IS COUNTERCLOCKWISE DIRECTION R2

STEP F
ROTATION SUBSTRATE 2 IS DRIVEN WITH VELOCITY CHARACTERISTIC 43 HAVING ACCELERATION b1

STEP H
ROTATION SUBSTRATE 2 IS DRIVEN WITH CONSTANT REVOLUTION RV2

STEP G
ROTATION SUBSTRATE 2 IS STOPPED WITH VELOCITY CHARACTERISTIC 44 HAVING ACCELERATION b2

STEP A
SOLUTION IS SUPPLIED FROM INLET 11 OF
ROTATION SUBSTRATE 2 INTO CHAMBER 6A

STEP A'
INLET 11 IS SEALED

ROTATION DIRECTION IS
COUNTERCLOCKWISE DIRECTION R2

STEP F
ROTATION SUBSTRATE 2 IS DRIVEN WITH VELOCITY
CHARACTERISTIC 43 HAVING ACCELERATION b1

STEP G
ROTATION SUBSTRATE 2 IS STOPPED WITH VELOCITY
CHARACTERISTIC 44 HAVING ACCELERATION b2

STEP I
ROTATION SUBSTRATE 2 IS MAINTAINED
IN A ROTATION STOP STATE

Fig.28

STEP A
SOLUTION IS SUPPLIED FROM INLET 11 OF ROTATION SUBSTRATE 2 INTO CHAMBER 6A

STEP A'
INLET 11 IS SEALED

ROTATION DIRECTION IS COUNTERCLOCKWISE DIRECTION R2

STEP F
ROTATION SUBSTRATE 2 IS DRIVEN WITH VELOCITY CHARACTERISTIC 43 HAVING ACCELERATION b1

STEP H
ROTATION SUBSTRATE 2 IS DRIVEN WITH CONSTANT REVOLUTION RV2

STEP G
ROTATION SUBSTRATE 2 IS STOPPED WITH VELOCITY CHARACTERISTIC 44 HAVING ACCELERATION b2

STEP I
ROTATION SUBSTRATE 2 IS MAINTAINED IN A ROTATION STOP STATE

US 7,497,996 B2

LIQUID DELIVERY APPARATUS AND LIQUID DELIVERY METHOD

This is a continuous application of International Application No. PCT/JP2005/22164, filed Dec. 2, 2005.

BACKGROUND OF THE INVENTION

The present invention relates to a liquid delivery apparatus and liquid delivery method. Particularly, the present invention relates to the liquid delivery apparatus and liquid delivery method for delivering liquid by controlling the flow of a minute amount of liquid in a minute or micro liquid passage.

Recently, a variety of health diagnostic chips have been developed. Almost all these health diagnostic chips are card-type devices having a micro liquid passage structure called a MICROTAS (μ-TAS: Micro Total Analysis System). The micro or fined liquid passage is very useful because microscopic amounts of sample need to be extracted from a biologic body. Further, the entire apparatus including the health diagnostic chip miniaturized by employing the micro liquid passages can be can be used not only in relatively large hospitals, but also for POCT (Point Of Care Test: field diagnostics thereof) applications in clinics and at home.

In macro systems, a pump is generally used as liquid delivery means. However, in micro liquid passages for manipulating extremely small quantities of fluids, a dead volume generated in a tube connected to the pump is not ignorable.

Methods advantageously used for liquid delivery in POCT applications include using a centrifugal force as a drive source. The advantage of this liquid delivery method is that no dead volume is generated and that a large number of processes can be executed concurrently and simultaneously. For example, Japanese Patent Application Laid-Open Publication No. 2001-503854 discloses a micro liquid delivery method adapting a capillary valve system. In this micro liquid delivery method, a flow of fluid is blocked by a capillary force generated in a micro liquid passage. Then, the centrifugal force generated by rotation of a rotary substrate breaks equilibrium of force so as to achieve liquid delivery from one micro chamber to other micro chamber.

However, according to the micro liquid delivery method disclosed in Japanese Patent Application Laid-Open Publication No. 2001-503854, because the centrifugal force generated by rotation serves as a drive source, an arrangement position of the valve is limited to the radially outward direction (centrifugal direction) of a rotary shaft of the rotary substrate wit respect to the supply side micro chamber. Further, the liquid delivery is also essentially limited only to one direction, namely, the centrifugal direction. Due to such restrictions relating the drive principle, the micro liquid delivery method disclosed in Japanese Patent Application Laid-Open Publication No. 2001-503854 restricts the design flexibility of the rotary substrate, places limitations upon the arrangement of liquid passage structure and behaviors of delivered liquid, and can not achieve liquid delivery with multiple functions.

SUMMARY OF THE INVENTION

It is an object of the present invention to provide a liquid delivery apparatus and liquid delivery method that achieve a liquid delivery behavior control with a high flexibility not limited to one direction, has a high degree of design flexibility, and achieve liquid delivery with multiple functions.

A first aspect of the present invention provides a liquid delivery apparatus comprising, a rotary substrate capable of rotating in at least a first rotation direction around a central axis of rotation, a first chamber formed in the rotary substrate and spatially closed except for an application port, a second chamber formed in the rotary substrate and spatially closed except for an air port, a first fluid passage formed in the rotary substrate, having a first fluid passage end portion connected to the first chamber and a second fluid passage end portion connected to the second chamber, and communicating the first chamber with the second chamber, the first fluid passage end portion extending from the first chamber along the first rotation direction of the rotary substrate, and the first fluid passage end portion holding a liquid accommodated in the first chamber by a capillary force, and a rotary drive unit capable of rotating the rotary substrate around the central axis of rotation so that an inertial force exceeding the capillary force and oriented in the first rotation direction acts on the liquid in the first fluid passage end portion.

The rotation direction is defined as a direction perpendicular to a virtual line perpendicular to the central axis of rotation and located on the same plane as the virtual line. For example, when the rotary substrate is fixed to a rotary shaft, a tangential direction perpendicular to a radial direction of the rotary shaft is regarded as the rotation direction. The first rotation direction can be either a clockwise direction or counterclockwise direction with respect to the central axis of rotation in the plan view.

The capillary force holds the liquid that has been applied to the first chamber through the application port at the first fluid passage end portion of the first fluid passage. Due to rotation of the rotary substrate driven by the rotary drive unit, the inertial force oriented in the first rotation direction acts on the liquid held in the first fluid passage end portion. When the inertial force exceeds the capillary force, the liquid accommodated in the first chamber flows into the first channel and is delivered to the second chamber. The air in the second chamber is exhausted to the outside via the air port.

For the liquid in the first chamber to be held by the capillary force and to be reliably delivered from the first chamber to the second chamber when the inertial force exceeds the capillary force, the first channel has to be a minute or micro liquid passage. Specifically, a width of the first channel is preferably set a range from 20 μm to 2000 μm, for example.

For example, the application port is a fluid passage communicating an inside of the first chamber formed in the rotary substrate with an outside of the rotary substrate. In this arrangement, an area of an opening of the application port needs to be sufficiently smaller than an area of the first chamber. Similarly, the air port is a fluid passage communicating an inside of the second chamber formed in the rotary substrate with the outside of the rotary substrate, for example. Further, the entirety or part of the second chamber can be formed of a material permeable to air but impermeable to liquid so that it functions as an air port.

The liquid is delivered from the first chamber to the second chamber via the first channel when the inertial force exceeds the capillary force holding the liquid in the first end portion, rather than by the centrifugal force. Therefore, the first liquid passage end portion, which is the boundary of the first chamber and first liquid passage, does not has to be arranged in a position outside the first chamber or on the farther side of the central axis of rotation than the first chamber. This increases flexibility relating to the arrangement of the first and second chambers and the first fluid passage.

In case that the centrifugal force serves as a drive force, the liquid delivery can be achieved only in one direction, i.e. in the centrifugal direction away from the first chamber of supply side and increasing the distance from the central axis of rotation. By contrast, in the liquid delivery apparatus of the first aspect of the present invention, the liquid can be delivered in any of the two directions, i.e. clockwise direction and counterclockwise direction, from the supply chamber 6A by setting the fist rotation direction, i.e. the extension direction of the inlet end portion 13, in any of those two directions. In other words, the liquid delivery apparatus of the first aspect of the present invention realizes the liquid delivery behavior control with a high flexibility which is not limited to one direction.

The liquid flow from the first to second chamber through the first fluid passage caused by the inertial force exceeding the capillary force encounters with flow resistance from fluid passage walls. The flow resistance acts as a component reducing a velocity of the liquid flow. However, because the flow resistance is less than the applied inertial force in minute or micro liquid passages, the liquid can be delivered in any direction from the first chamber. In other words, the second chamber can be arranged closer to the central axis of rotation than the first chamber to deliver the liquid in the centripetal direction from the first chamber. This realizes a more complex liquid delivery and increased design flexibility, thereby facilitating the design of liquid delivery apparatus.

Specifically, for generating the inertial force in the liquid in the first fluid passage end portion, the rotary drive unit rotates the rotary substrate in the first rotation direction, i.e. in the extension direction of the first fluid passage end portion from the first chamber, and then abruptly brakes the rotation of the rotary substrate. That is, after rotating the rotary substrate in the first rotation direction, the rotary drive unit stops the rotary substrate by a velocity characteristic having a first acceleration so that the first acceleration generates the inertial force exceeding the capillary force and acting on the liquid in the first fluid passage end portion.

The rotation of the rotary substrate in the first rotation direction generates the centrifugal force acting on the liquid in the first fluid passages end portion. The centrifugal force is directed in the centrifugal direction, i.e. in the direction away from the central axis of rotation. Because the direction of the centrifugal force acts is different from the direction in which the first fluid passage end portion extends from the first chamber, the liquid is held in the first chamber by the capillary force without flowing into the first fluid passage. When the rotary substrate rotating in the first rotation direction is abruptly braked, the liquid accommodated in the first chamber and held in the first fluid passage end portion will continue to move in the first rotation direction according to the law of inertia. As a result, the inertial force in the first rotation direction will act on the liquid held in the first fluid passage end portion. Specifically, the inertial force in the first rotation direction proportional to the first acceleration during stopping the rotation of the rotary substrate will act on the liquid in the first fluid passage end portion. As a result of that the inertial force exceeds the capillary force holding the liquid in the first fluid passage end portion, the liquid held in the first fluid passage end portion will flow into the first fluid passage and will flow from the second fluid passage end portion into the second chamber via the first fluid passage.

For achieving the liquid delivery by the inertial force due to the abrupt braking, an angle formed between the first fluid passage end portion and the first rotation direction may be set at a range not less than −45° and not more than +45°. Therefore, the design with respect to the direction of the first fluid passage end portion has high flexibility with advantages in view of productivity.

Alternatively, for generating the inertial force in the liquid in the first fluid passage end portion, the rotary drive unit rapidly rotates the rotary substrate in a second rotation direction, i.e. in a direction opposite to that in which the first fluid passage end portion extends from the first chamber. In other words, the rotary drive unit rotates the rotary substrate by a velocity characteristic having a second acceleration in the second rotation direction opposite to the first rotation direction so that the second acceleration generates the inertial force exceeding the capillary force and acting on the liquid in the first fluid passage end portion.

If the first rotation direction is the clockwise direction with respect to the central axis of rotation in the plan view, the second rotation direction is the counterclockwise direction with respect to the central axis of rotation. Conversely, if the first rotation direction is the counterclockwise direction with respect to the central axis of rotation in the plan view, the second rotation direction is the clockwise direction with respect to the central axis of rotation.

When the rotary substrate is rapidly rotated in the second rotation direction, the liquid accommodated in the first chamber and held in the first fluid passage end portion will maintain the stationary state according to the law of inertia. As a result, the inertial force in the direction opposite to the second rotation direction, i.e. in the first direction, will act on the liquid held in the first fluid passage end portion. Specifically, the inertial force in the first rotation direction proportional to the second acceleration while rapid rotation of the rotary substrate in the second rotation direction acts on the liquid in the first fluid passage end portion. As a result of that the inertial force exceeds the capillary force holding the liquid in the first fluid passage end portion, the liquid held in the first fluid passage end portion will flow into the first channel and will flow from the second fluid passage end portion to the second chamber via the first channel. Rapid liquid delivery from the first chamber to the second chamber can be thus realized only by rapid rotation of the rotary substrate. Therefore, the liquid delivery by rapid rotation of the rotary substrate is suitable for liquid delivery in the case of a short reaction time after mixing, such as in the case of chemical reactions.

For achieving the liquid delivery by the inertial force due to the rapid rotation, an angle formed between the first fluid passage end portion and the second rotation direction may be set at a range not less than 135° and not more than 235°. Therefore, the design with respect to the direction of the first fluid passage end portion has high flexibility with advantages in view of productivity. As described above, the second chamber can be arranged at a position closer to the central axis or rotation than the first chamber.

Preferably, the second fluid passage end portion of the first fluid passage connected to the second chamber extends in a direction perpendicular to the first rotation direction. This arrangement prevents the liquid that has flowed into the second chamber from flowing back through the first fluid passage from the second fluid passage end portion into the first chamber due to the inertial force generated by the above-described abrupt braking or rapid rotation of the rotary substrate.

It is preferable that the first fluid passage end portion of the first fluid passage has hydrophobic property.

Having hydrophobic property means that the first fluid passage end portion of the first fluid passage is made from a hydrophobic material or subjected to a treatment providing it with hydrophobic property. The hydrophobic property of the first fluid passage end portion assures that the liquid accommodated in the first chamber is reliably held in the first fluid passage end portion. Specifically, the sufficiently small width of the first fluid passage as described above and the hydrophobic property of the first the liquid does not leak into the first channel due to surface tension and is held in the first fluid passage end portion.

The entirety of the first channel may have hydrophobic property. This makes it possible not only that the liquid is held more reliably in the first fluid passage end portion, but also that the liquid is held over the entire length of the first fluid passage. Further, the larger is the length of the first channel, the more rigidly the liquid can be held in the first chamber. Therefore, when the entirety of the first channel has hydrophobic property, the above-described abrupt braking or rapid rotation of the rotary substrate needs to be repeated to deliver a certain amount of liquid from the first chamber into the second chamber. Controlling the number of cycles of the abrupt braking or rapid rotation provides more accurate deliver of set amount of the liquid from the first chamber into the second chamber. Further, adjusting the time of repeated abrupt braking or rapid rotation makes it possible to control the time required to deliver the predetermined amount of liquid from the first chamber into the second chamber. The control of time required for liquid delivery is suitable for delivering liquid when another mixing is conducted after the prescribed reaction time elapses after the initial mixing.

The entirety of the rotary substrate may have hydrophobic property. If the entire rotary substrate is hydrophobic, for example, the entire rotary substrate, rather than only a specific site such as the first fluid passage end portion, may be made from a hydrophobic material, or the entire rotary substrate may be subjected to a treatment providing it with hydrophobic properties. Therefore, productivity of the rotary substrate can be increased.

It is preferable that the second fluid passage end portion of the first fluid passage have hydrophilic property.

Having hydrophilic properties means that the second fluid passage end portion of the first channel is made from a hydrophilic material or subjected to a treatment providing it with hydrophilic property. Due to the hydrophilic property of the second fluid passage end portion, the liquid flowed into the first channel under the effect of the inertial force generated by the above-described abrupt braking or rapid rotation of the rotary substrate reliably flows from the second fluid passage end portion into the second chamber by moistening effect and capillary phenomenon. Therefore, the desirable liquid delivery behavior can be realized more accurately.

The entirety of the first fluid passage except for the first fluid passage end portion may have hydrophilic property. The hydrophilic property of the entirety of the first fluid passage except for the first fluid passage end portion achieves that the liquid flows into the second chamber more reliably by the moistening effect and capillary phenomenon.

In order to reliably hold the liquid accommodated in the first chamber in the first fluid passage end portion by a non-moistening effect and to reliably deliver the liquid from the first chamber into the second chamber if the holding in the first fluid passage end portion is canceled by the inertial force due to the abrupt braking or rapid rotation of the rotary substrate, it is preferred that the first and second chambers have hydrophilic property, that the first fluid passage end portion of the first fluid passage has hydrophobic property, and that the entirety of the first fluid passage except for the first fluid passage end portion has hydrophilic property.

It is preferred that a plurality of passage sites respectively including at least the first chamber, second chamber, and first fluid passage are formed in the rotary substrate. Providing a plurality of passage sites integrally in one rotary substrate makes it possible to deliver the liquid accommodated in the first chamber of each passage sites simultaneously into the second chamber by executing one cycle of the above-described abrupt braking or rapid rotation of the rotary substrate. Therefore, the number of processes executed concurrently and simultaneously can be increased, resulting in that a large number of samples can be treated within a short time period. Further, the large number of passage sites formed in one rotary substrate also contributes to the decrease in the treatment cost of each sample in view of the production cost of the rotary substrate.

Furthermore, the liquid delivery apparatus may further comprise a third chamber formed in the rotary substrate and spatially closed except for an air port, and a second fluid passage formed in the rotary substrate, having a third fluid passage end portion connected to the first chamber and a fourth fluid passage end portion connected to the third chamber, and communicating the first chamber with the third chamber, the third fluid passage end portion extending from the first chamber along a second rotation direction of the rotary substrate opposite to the first rotation direction, and the third fluid passage end portion holding the liquid accommodated in the first chamber by the capillary force. The rotary drive unit is capable of rotating the rotary substrate around the central axis of rotation so that the inertial force exceeding the capillary force and oriented in the second rotation direction acts on the liquid in the third fluid passage end portion.

The first fluid passage end portion connecting the first fluid passage to the first chamber extends in the first rotation direction, whereas the third fluid passage end portion connecting the second fluid passage to the first chamber extends in the second rotation direction opposite to the first rotation direction. In other words, the first and third fluid passage end portions connected to the first chamber extend in the mutually opposite directions. Therefore, depending on the direction in which the rotary drive unit rotates the rotary substrate (clockwise direction or counterclockwise direction), the liquid can be delivered from the first chamber into the second chamber via the first fluid passage and into the third chamber via the second fluid passage. In other words, one of the second and third chambers can be selected for delivering the liquid from the first chamber by selecting the direction for rotating the rotary substrate with the rotary drive unit. Further, switching the direction in which the rotary drive unit rotates the rotary substrate makes it possible to deliver the liquid continuously from the first chamber into the second chamber and third chamber. As a result, a complex reaction can be realized with one group of liquid passages.

Furthermore, the liquid delivery apparatus may further comprise a fourth chamber formed in the rotary substrate and spatially closed except for an air port, and a third fluid passage formed in the rotary substrate, having a fifth fluid passage end portion connected to the second chamber and a sixth fluid passage end portion connected to the fourth chamber, and communicating the second chamber with the fourth chamber, the fifth fluid passage end portion extending from the second chamber along the first rotation direction or along a second rotation direction of the rotary substrate opposite to the first rotation direction, and fifth fluid passage end portion holds the liquid accommodated in the second chamber by the capillary force. The rotary drive unit is capable of rotating the rotary substrate around the central axis of rotation so that the inertial force exceeding the capillary force and oriented in a direction along which the fifth fluid passage end portion extends from the second chamber acts on the liquid.

The multistage liquid delivery can be realized. Specifically, the liquid can be delivered from the first chamber to the second chamber via the first fluid passage, and then the liquid accommodated in the second chamber can be delivered to the fourth chamber via the third fluid passage. Therefore, a more complex reaction function can be realized. For example, extraction, mixing, reaction, and detection can be successively executed with one group of fluid passages.

The rotary drive unit comprises a motor for rotating the rotary substrate, and a velocity characteristic application unit for providing the motor with the velocity characteristic.

For example, a DC motor, a DC brushless motor, an AC motor, or a stepping motor can be employed as the motor. When the stepping motor is employed, the above-described rotation and abrupt braking can be easily realized by applying an external drive signal.

Further, the rotary drive unit may comprise a rotation velocity detector for detecting the rotation velocity of the rotary substrate during rotation, and a rotation velocity correction unit for correcting the velocity characteristic provided to the motor by the velocity characteristic application unit based on the rotation velocity detected by the rotation velocity detector. Because the rotary substrate can be rotated with correcting the velocity characteristic according to feedback of the actual rotation velocity, the amount of delivered liquid is stabilized and cyclic reproducibility of the amount of delivered liquid is enhanced.

The second aspect of the present invention provides a rotary substrate for a liquid delivery apparatus capable of rotating in at least a first rotation direction around a central axis of rotation. The rotary substrate is formed with a first chamber spatially closed except for an application port, a second chamber spatially closed except for an air port, and a first fluid passage having a first fluid passage end portion connected to the first chamber and a second fluid passage end portion connected to the second chamber, and communicating the first chamber with the second chamber, the first fluid passage end portion extending from the first chamber in the first rotation direction of the rotary substrate.

The second aspect of the present invention provides a liquid delivery method. The method comprises, preparing a rotary substrate capable of rotating in at least a first rotation direction around a central axis of rotation, the rotary substrate being formed with a first chamber spatially closed, a second chamber spatially closed, and a fluid passage having a first fluid passage end portion connected to the first chamber and a second fluid passage end portion connected to the second chamber and connecting the first fluid passage with the second fluid passage, the first fluid passage end portion extending from the first chamber in the first rotation direction of the rotary substrate, and the first fluid passage end portion holding a liquid accommodated in the first chamber by a capillary force, and rotating the rotary substrate around the central axis of rotation so that an inertial force exceeding the capillary force and oriented in the first rotation direction acts on the liquid in the first fluid passage end portion.

Specifically, the rotating of the rotary substrate comprises rotating the rotary substrate according to a velocity characteristic having a first acceleration in the first rotation direction, and stopping the rotation of the rotary substrate in the first rotation direction by a velocity characteristic having a second acceleration with an absolute value larger than that of the first acceleration, so that the inertial force exceeding the capillary force and oriented in the first rotation direction acts on the liquid located in the first fluid passage end portion. For example, the first acceleration is 600 rpm/sec and the second acceleration is not less than 1000 rpm/sec and not more than 60,000 rpm/sec or less.

The rotation of the rotary substrate in the first rotation direction generates the centrifugal force acting on the liquid in the first fluid passages end portion. The centrifugal force is directed in the centrifugal direction, i.e. in the direction away from the central axis of rotation. Because the direction of the centrifugal force acts is different from the direction in which the first fluid passage end portion extends from the first chamber, the liquid is held in the first chamber by the capillary force without flowing into the first fluid passage. When the rotary substrate rotating in the first rotation direction is stopped by the velocity characteristic having the second acceleration with the absolute value larger than that of the first acceleration, the liquid accommodated in the first chamber and held in the first fluid passage end portion will continue to move in the first rotation direction according to the law of inertia. As a result, the inertial force in the first rotation direction proportional to the second acceleration will act on the liquid held in the first fluid passage end portion. As a result of that, the inertial force exceeds the capillary force holding the liquid in the first fluid passage end portion, the liquid held in the first fluid passage end portion will flow into the first fluid passage and eventually flows into the second chamber.

Alternatively, the rotating of the rotary substrate comprises, rotating the rotary substrate by a velocity characteristic having a third acceleration in a second rotation direction opposite to the first rotation direction, so that the inertial force exceeding the capillary force and oriented in the first rotation direction acts on the liquid located in the first fluid passage end portion, and stopping the rotation of the rotary substrate in the second rotation direction by a velocity characteristic having a fourth acceleration with an absolute value less than that of the third acceleration. For example, the third acceleration is 00 rpm/sec, and the fourth acceleration is not less than 1000 rpm/sec and not more than 60,000 rpm/sec.

When the rotary substrate is rapidly rotated in the second rotation direction, the liquid accommodated in the first chamber and held in the first fluid passage end portion will maintain the stationary state according to the law of inertia. As a result, the inertial force in the first direction proportional to the third acceleration while rapid rotation of the rotary substrate in the second direction acts on the liquid accommodated in the first chamber and held in the first fluid passage end portion. As a result of that the inertial force exceeds the capillary force holding the liquid in the first fluid passage end portion, the liquid held in the first fluid passage end portion will flow into the first fluid passage and eventually flows into the second chamber.

Before execution of the above-mentioned abrupt stopping or rapid rotation, the liquid is applied into the first chamber from an application port communicating the first chamber with an outside of the rotary substrate.

With the liquid delivery apparatus and method of the present invention, the liquid delivery is realized by that the inertial force generated by the abrupt braking or rapid rotation of the rotary substrate, rather than the centrifugal or centripetal force, exceeds the capillary force holding the liquid. Therefore, liquid delivery behavior control with a high flexibility not limited to one direction can be realized, resulting in that the degree of design flexibility is high, and that liquid delivery can be provided with various functions.

BRIEF DESCRIPTION OF THE DRAWINGS

Other objects and characteristics of the present invention shall be clarified by the following description on the preferred embodiments with reference to the accompanying drawings.

FIG. 5 is a flowchart for explaining the first example of the operation of the liquid delivery apparatus according to the first embodiment of the present invention;

FIG. 6 is a diagram illustrating a velocity waveform and rotation direction of the first example of the operation of the liquid delivery apparatus according to the first embodiment of the present invention;

FIG. 8 is a flowchart for explaining a second example of the operation of the liquid delivery apparatus according to the first embodiment of the present invention;

FIG. 9 is a diagram illustrating a velocity waveform and rotation direction of the second example of the operation of the liquid delivery apparatus according to the first embodiment of the present invention;

FIG. 14 is a flowchart for explaining a sixth example of the operation of the liquid delivery apparatus according to the first embodiment of the present invention;

FIG. 19 is a flowchart for explaining a first example of operation of the liquid delivery apparatus according to a second embodiment of the present invention;

FIG. 22 is a flowchart for explaining a second example of the operation of the liquid delivery apparatus according to the second embodiment of the present invention;

FIG. 25 is a flowchart for explaining a fourth example of the operation of the liquid delivery apparatus according to the second embodiment of the present invention;

FIG. 28 is a flowchart for explaining a sixth example of the operation of the liquid delivery apparatus according to the second embodiment of the present invention;

DESCRIPTION OF THE PREFERRED EMBODIMENTS

The embodiments of the present invention will be described in detail with reference to the accompanying drawings.

First Embodiment

Figure 1:
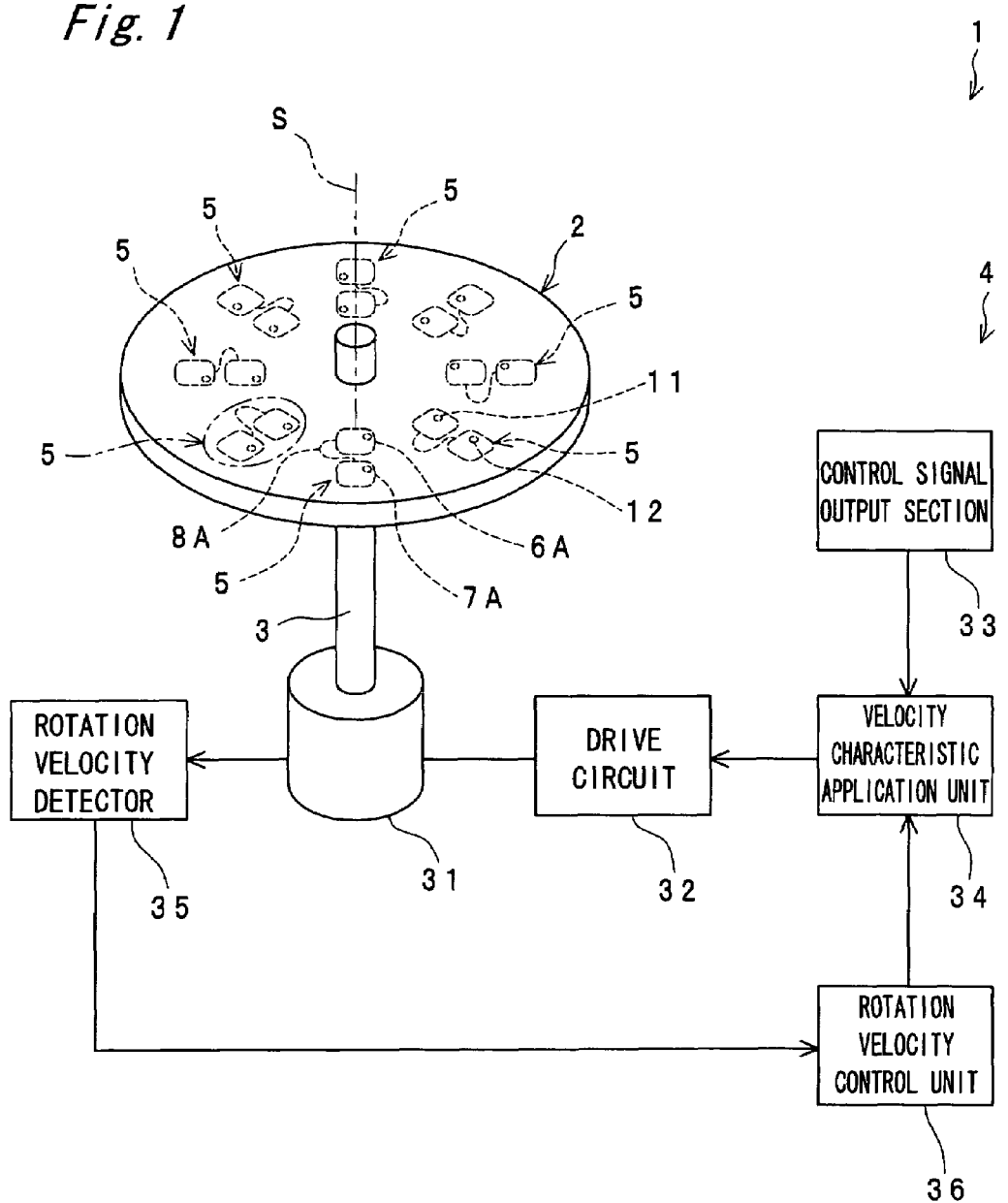
FIG. 1 is a schematic structural view illustrating a liquid delivery apparatus according to a first embodiment of the present invention.
Figure 2:
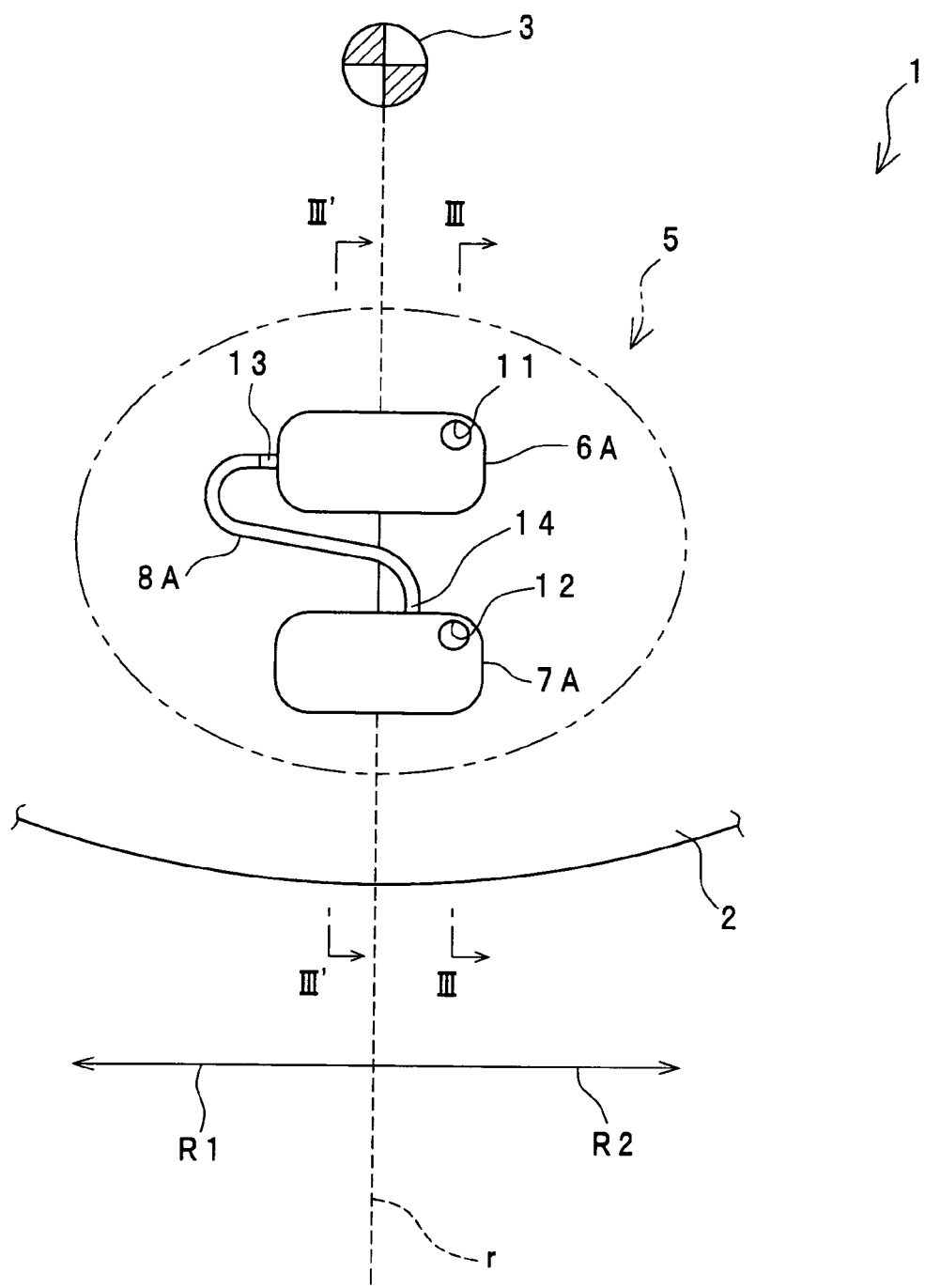
FIG. 2 is a partially enlarged plan view of the rotary substrate according to the first embodiment of the present invention.

FIGS. 1 to 2 show a liquid delivery apparatus 1 according to a first embodiment of the present invention.

The liquid delivery apparatus 1 comprises a rotary substrate 2, a rotary shaft 3 to which the rotary substrate 2 is fixed, and a rotary drive unit 4 for rotating the rotary shaft 3. The rotary shaft 3 is arranged so that an axial line (central axis of rotation) S thereof extends in a vertical direction. The rotary substrate 2 is fixed to an upper end side of the rotary shaft 3. The rotary substrate 2 has a round shape in the plan view, and the center of the rotary substrate 2 coincides with the axial line S of the rotary shaft 3. On the other hand, the lower end side of the rotary shaft 3 is linked to the below-described motor 31. The outer shape of the rotary substrate 2 can be set to any dimensions accommodating the passage sites 5. The diameter of the rotary substrate 2 is, for example, set to a range not less than 10 mm and nor more than 150 mm. Further, the thickness of the rotary substrate 2 is set to a range not less than 0.2 mm and not more than 20 mm.

The rotary substrate 2 rotates together with the rotary shaft 3. In the following descriptions, a rotation direction of the rotary shaft 3 is defined as a direction perpendicular to the radial direction "r" of the rotary shaft 3, as shown by arrows R1, R2 in FIG. 2. In other words, the rotation direction is defined as a direction perpendicular to a virtual line that is perpendicular to the axial line S of the rotary shaft 3 and located on the same plate as the virtual line. The rotary substrate 2 can be rotated in two directions, i.e. in a clockwise direction R1 and counterclockwise direction R2, in the plan view thereof.

As shown in FIG. 1, in the rotary substrate 2, a plurality of passage sites 5 are arranged radially around the rotary shaft 3. Further referring to FIGS. 2, 3A, and 3B, the passage site 5 comprises a supply chamber (first chamber) 6A, a target chamber (second chamber) 7A, and a channel or fluid passage (first fluid passage) 8A. Providing a plurality of passage sites 5 integrally in one rotary substrate 2 makes it possible to deliver the liquid accommodated in the supply chambers 6A of all the passage sites 5 simultaneously into the target chambers 7A by executing abrupt braking or rapid rotation of the rotary substrate 2 described-latter in one cycle. Therefore, integrating the passage sites 5 makes it possible to increase the number of processes executed concurrently and simultaneously, resulting in that a large number of samples can be treated within a short time period. Further, the large number of passage sites 5 formed in one rotary substrate 2 also contributes to the decrease in the treatment cost of each sample in view of the production cost of the rotary substrate 2.

The supply chamber 6A is a chamber for accumulating a solution or liquid 9 (for example, see FIG. 7A) that is the object of liquid delivery. The supply chamber 6A is formed inside the rotary substrate 2 and spatially closed to confined. However, an application port 11 with a circular cross section that passes from an upper wall of the supply chamber 6A to an upper surface of the rotary substrate 2 and communicates the inside of the supply chamber 6A with the outside of the rotary substrate 2 is formed in the rotary substrate 2. The application port 11 is used for applying the liquid 9 into the supply chamber 6A. The target chamber 7A is a chamber into which the liquid 9 is delivered from the supply chamber 6A. The target chamber 7A is formed inside the rotary substrate 2 and is spatially closed or confined. However, an air port 12 with a circular cross section that passes from the upper wall of the target chamber 7A to the upper surface of the rotary substrate 2 and communicate the inside of the target chamber 7A to the outside of the rotary substrate 2 is formed in the rotary substrate 2. This air port 12 has a function of draining the air present inside the target chamber 7A to the outside of the rotary substrate 2 when the liquid 9 flows into the target chamber 7A. The channel 8A is a channel for fluidly communicating the supply chamber 6A and the target chamber 7A each other. The channel 8A is formed inside the rotary substrate 2 and spatially closed or confined. Further, both ends of the channel 8A, i.e. an inlet end portion (first fluid passage end portion) 13 and an outlet end portion (second fluid passage end portion) 14 are respectively connected to the supply chamber 6A and target chamber 7A.

The supply chamber 6A will be described below in detail. Referring to FIG. 2, the supply chamber 6A has a generally rectangular shape in the plan view thereof, and the inlet end portion 13 of the channel 8A is opened in a side wall on the left side thereof. The application port 11 is provided in a position closer to the rotary shaft 3 than the inlet end portion 13. Specifically, the application port 11 is provided in an upper right corner of the supply chamber 6A in FIG. 2. Further, an area of the application port 11 in the plan view thereof is set to be sufficiently small comparing with the area of the supply chamber 6A in the plan view thereof. Such set position and area of the application port 11 assures that the liquid 9 does not leak or spatter through the application port 11 by an outwardly centrifugal force in the radial direction "r" acting on the liquid 9 during rotation of the rotary substrate 2 and flows to the fluid passage 8A. Therefore, such set position and area of the application port 11 allows that the application port 11 remain open while the rotary substrate 2 is rotated after the liquid 9 is applied into the supply chamber 6A. Contrary to this, in case that the application port 11 is provided in a position farther from the rotary shaft 3 than the inlet end portion 13, or when the area of the application port 11 is relatively large comparing to that of the supply chamber 6A, the application port 11 has to be sealed before the rotary substrate 2 is rotated in order to prevent the liquid 9 located inside the supply chamber 6A from leaking or spattering when the rotary substrate 2 is rotated. Dimensions and volume of the supply chamber 6A have to be determined according to the amount of liquid sample (liquid 9). The volume of the supply chamber 6A is preferably set a range not less than 0.1 µL and not more than 100 µL.

The target chamber 7A will be described below in detail. The target chamber 7A has a generally rectangular shape in the plan view thereof. Further, the target chamber 7A is arranged so as to be aligned with the supply chamber 6A in the radial direction "r" and positioned farther from the rotary shaft 3 than the supply chamber 6A. The outlet end portion 14 of the channel 8A is opened in a side wall of the target chamber 7A on the side of the rotary shaft 3 in the plan view thereof. The area of the air port 12 in the plan view thereof is set to be sufficiently smaller than the area of the target chamber 7A in the plan view thereof so that the liquid 9 does not leak or spatter through the air port 12 by an outwardly centrifugal force in the radial direction "r" acting on the liquid 9 during rotation of the rotary substrate 2. Dimensions and volume of the target chamber 7A have to be determined according to the amount of liquid sample (liquid 9). The volume of the target chamber 7A is preferably set a range not less than 0.1 µL and not more than 100 µL.

The channel 8A will be described below in detail. The channel 8A needs to be a minute or micro channel so that the liquid 9 can be reliably delivered from the supply chamber 6A to the target chamber 7A through the channel 8A. Specifically, it is preferable that the volume of the channel 8A is almost equal to or less than that of the supply chamber 6A and target chamber 7A. Further, a width of the channel 8A is preferably less than that of the supply chamber 6A and target chamber 7A. For example, the width of the channel 8A is preferably not less than 20 µm and not more than 2000 µm, more preferably not less than 10 µm and not more than 100 µm. Further, a depth of the channel 8A is preferably less than that of the supply chamber 6A and target chamber 7A. For example, when the width of the channel 8A is not less than 50 µm and not more than 500 µm, the depth of the channel 8A is preferably not less than 10 µm and not more than 100 µm. In the present embodiment, the channel 8A meanders so to be an S-like shape in the plan view thereof.

The inlet end portion 13 of the channel 8A connected to the supply chamber 6A functions as a valve for removably holding the liquid 9 accommodated in the supply chamber 6A. The inlet end portion 13 extends in the clockwise direction R1 of the two rotation directions of the rotary substrate 2 from the supply chamber 6A. Such direction of the inlet end portion 13 enables the liquid 9 in the supply chamber 6A to be introduced into the fluid passage 8A by inertial force acting on the liquid 9 during rotation of the rotary substrate 2. On the other hand, the outlet end portion 14 of the channel 8A connected to the target chamber 7A extends toward the target chamber 7A in the radial direction "r" of the rotary shaft 3, i.e. in the direction perpendicular to the rotation direction of the rotary substrate 2 (clockwise direction R1 and counterclockwise direction R2). Such direction of the outlet end portion 14 prevents the liquid 9 once flowed into the target chamber 7A from flowing back in the fluid passage 8A from the outlet end portion 14 to the supply chamber 6A.

Wettability of wall surfaces constituting the passage site 5 will be described. The channel wall of the inlet end portion 13 of the channel 8A is composed of a hydrophobic material or subjected to a treatment providing it with hydrophobic property. The hydrophobic property of the inlet end portion 13 assures that the liquid accommodated in the supply chamber 6A can be reliably held in the inlet end portion 13 by a capillary force. On the other hand, the remaining portions of the passage site 5, i.e. the wall surfaces of the supply chamber 6A, the wall surfaces of the target chamber 7A, and the wall surfaces of the entirety of the channel 8A except for the inlet end portion 13 (including the outlet end portion 14) are composed of a hydrophilic material or subjected to a treatment providing them with hydrophilic property. Due to the hydrophilic properties of these portions, the liquid that flowed from the supply chamber 6A into the channel 8A will reliably flow into the target chamber 7A by moistening effect and capillary phenomenon.

Examples of hydrophobic materials include semiconductor materials such as monocrystalline silicon, amorphous silicon, silicon carbide, silicon oxide, and silicon nitride, inorganic insulating materials selected from the group including alumina, sapphire, forsterite, silicon carbide, silicon oxide, and silicon nitride, and organic materials selected from the group including polyethylene, ethylene, polypropylene, polyisobutylene, polyethylene terephthalate (PET), unsaturated polyesters, fluorine resins, polyvinyl chloride, polyvinylidene chloride, polyvinyl acetate, polyvinyl alcohol, polyvinyl acetals, acrylic resins, polyacrylonitrile, polystyrene, acetal resins, polycarbonates (PC), polyamides, phenolic resins, urea resins, epoxy resins, melamine resins, styrene-acrylonitrile copolymer, acrylonitrile-butadiene styrene copolymer, silicone resins, polyphenylene oxide, and polysulfones. The preferred among those materials are PET and PC. Examples of materials that can provide hydrophobic property include fluorine resin coating agents and silicone coating agents. The preferred among them are fluorine resin coating agents.

Examples of hydrophilic materials include glass, quartz glass and metal materials such as aluminum, copper, and stainless steel. The metal materials need to have clean surface obtained by removing organic substances that adhered thereto. Examples of materials that can provide hydrophilic properties include surfactants such as Triton X (GE Healthcare) and polymer compounds having hydrophilic groups such as hydroxyl groups, sulfone group, and carboxyl groups. It is preferred to use surfactants.

Figure 3A:
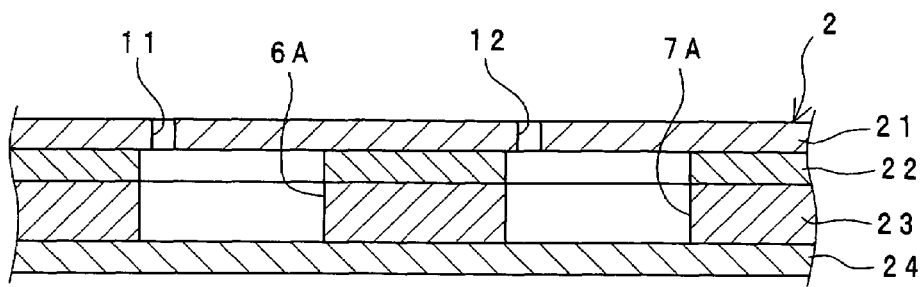
FIG. 3A is a partial cross-sectional view taken along a line III-III in FIG. 2.
Figure 3B:
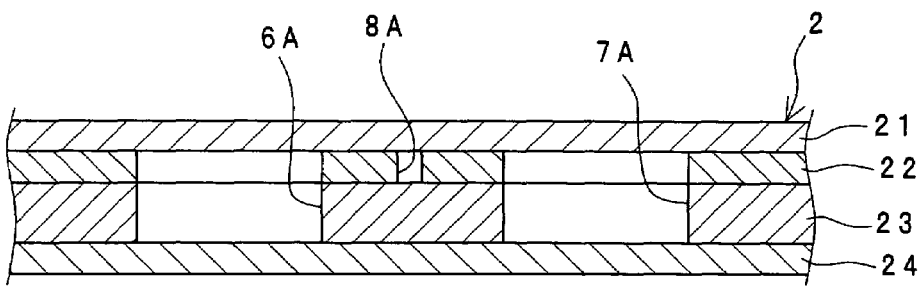
FIG. 3B is a partial cross-sectional view taken along a line III'-III' in FIG. 2.
Figure 4:
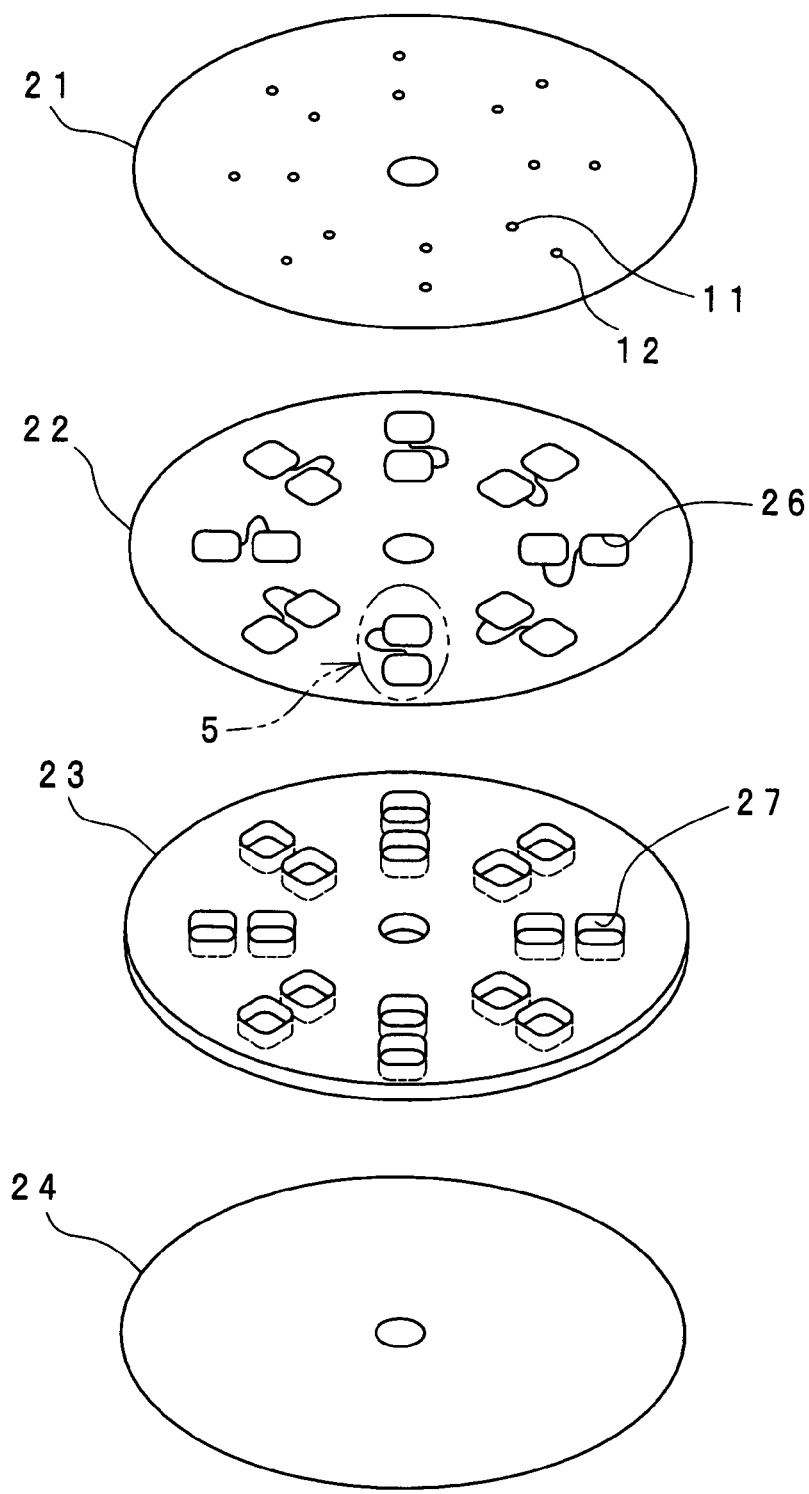
FIG. 4 is an exploded perspective view of the rotary substrate according to the first embodiment of the present invention.

The laminated structure of the rotary substrate 2 will be described below with reference to FIGS. 3A, 3B, and 4. The rotary substrate 2 has a four-layer structure in which an upper surface substrate 21, a fluid passage substrate 22, a chamber substrate 23, and a lower surface substrate 24 are bonded in a laminated state. The application port 11 and air port 12 are provided in the upper surface substrate 21 so as to pass through in a thickness direction. Groove holes 26 respectively having a shape corresponding to the supply chamber 6A, target chamber 7A, and channel 8A are formed in the channel substrate 22 so as to pass through in a thickness direction.

Groove holes 27 respectively having a shape corresponding to the supply chamber 6A and target chamber 7A are formed in the chamber substrate 23 so as to pass through in a thickness direction. The lower surface substrate 24 constitutes a bottom surface of the supply chamber 6A and target chamber 7A and is not provided with grooves or holes. The rotary substrate 2 of such multilayer structure can be manufactured by joining or bonding the substrates, thereby providing excellent productivity. Further, the depth of the channel 8A is determined by the thickness of the channel substrate 22, and the depth of the supply chamber 6A and target chamber 7A is determined by the combined thickness of the channel substrate 22 and chamber substrate 23. Therefore, a structure in which the depth of the channel 8A is less than the depth of the supply chamber 6A and target chamber 7A can be easily fabricated, and the depth of the channel 8A and the depth of the supply chamber 6A and target chamber 7A can be independently set from each other. For example, when the depth of the channel 8A is approximately 100 µm, a sheet-like channel substrate 22 in which the shape of the channel 8A, supply chamber 6A, and target chamber 7A is cut through, which is preferable in view of productivity, can be used. Further, because the lower surface substrate 24 constituting the bottom section of the supply chamber 6A and target chamber 7A is a member separate from other substrates, a reactive agent can be easily supported on the lower surface substrate 24 prior to bonding. For example, a reactive agent can be supported on the bottom section of the target chamber 7A with the object of reacting with the liquid to be delivered from the supply chamber 6A.

A variety of methods known to those skilled in the art can be employed for bonding the substrate layers. For example, an adhesive material or a sheet having adhesive property may be interposed between the substrate layers, or the layers may be bonded by other method such as ultrasound bonding, thermal fusion bonding, or laminator processing. A variety of methods known to those skilled in the art can be also used for forming the fluid passages and chambers. Examples of suitable methods include photolithography employed in fine processing of semiconductors, injection molding employed in plastic molding, machining, and transfer processing by producing a copy from a master substrate. Among these methods, photolithography is especially preferable.

The rotary drive unit 4 will be described below with reference to FIG. 1. The rotary drive unit 4 comprises a motor 31 mechanically connected to the rotary shaft 3 and adapts to rotate the rotary shaft 3 and the rotary substrate 2 fixed to the rotary shaft 3, and a drive circuit 32 for the motor 31. Further, the rotary drive unit 4 comprises a control signal output unit 33 for outputting a control signal, and a velocity characteristic application unit 34 for providing the desired velocity characteristic, for example such as shown in FIG. 6, to the drive circuit 32 of the motor 31, based on the control signal inputted from the control signal output unit 33. The control signal output unit 33 may be an external computer separate from the liquid delivery apparatus 1.

A DC motor, a DC brushless motor, an AC motor, or a stepping motor can be employed as the motor 31. The stepping motor is preferred because rapid rotation and abrupt braking of the rotary substrate 2 can be easily realized by applying an external drive signal. Further, The DC motor does not require a special drive circuit 32. When a DC brushless motor is employed as the motor 31, faster braking can be realized by the drive circuit 32 having a function of applying a reverse rotation voltage.

Further, the rotary drive unit 4 comprises a rotation velocity detector 35 for detecting the rotation velocity of the rotary substrate 2 during rotation, and a rotation velocity control unit 36 for correcting the velocity characteristic provided by the velocity characteristic application unit 34. The actual rotation velocity of the rotary substrate 2 detected by the rotation velocity detector 35 is sent to the rotation velocity control unit 36. The rotation velocity control unit 36 corrects the velocity characteristic provided by the velocity characteristic application unit 34 so as to compensate difference between the actual detected rotation velocity characteristic and the velocity characteristic to be provided to the motor 31. Because the rotary substrate 2 is rotated with correcting the velocity characteristic according to feedback of the actual rotation velocity of the rotary substrate 2, stabilized liquid delivery can be realized and cyclic reproducibility of the amount of delivered liquid can be enhanced.

Figure 7A:
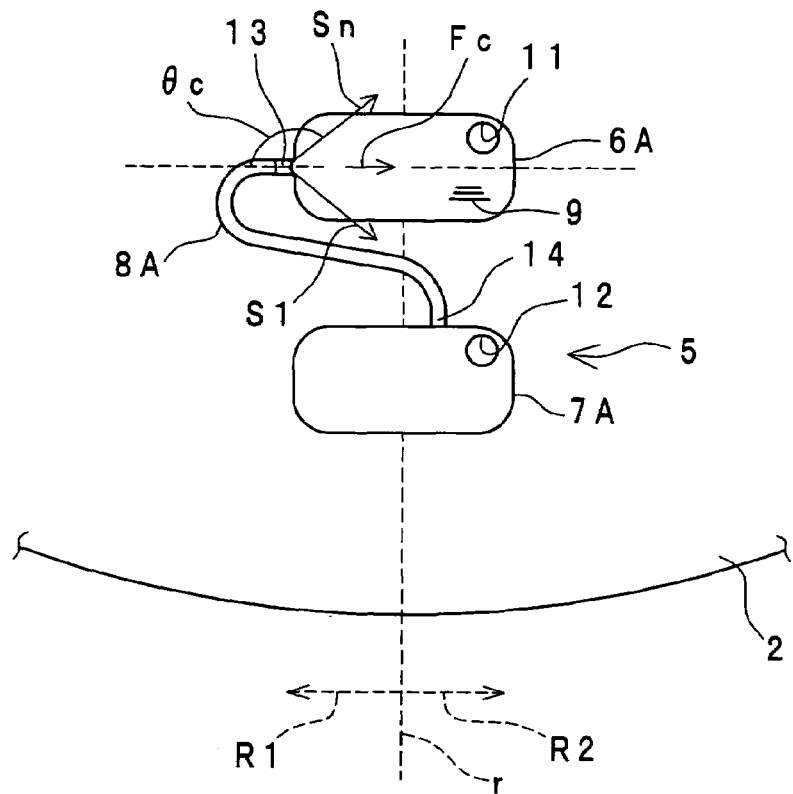
FIG. 7A is a schematic plan view for explaining the forces acting on a liquid in a fluid passage end portion before rotation of the rotary substrate starts.

A liquid delivery method using the liquid delivery apparatus 1 according to the first embodiment will be described. Referring to a flowchart shown in FIG. 5, the liquid 9 is applied from the application port 11 of the rotary substrate 2 so that the supply chamber 6A is filled with the liquid 9 (step A). Referring to FIG. 7A, as described above, the inlet end portion 13 of the liquid passage 8A connected to the supply chamber 6A has hydrophobic property and the liquid passage 8A is a minute or micro liquid passage. Therefore, the liquid 9 is held in the inlet end portion 13 by the capillary force Fc caused by surface tension, and the inside of the channel 8A is not wetted with the liquid 9. Because the wall surface of the inlet end portion 13 has hydrophobic property, the inlet end portion 13 is not wetted with the liquid 9 and a contact angle θc of the liquid 9 to the wall surface is an obtuse angle, resulting in that the capillary force Fc having such direction as to hold the liquid 9 in the supply chamber 6A is generated. Specifically, surface tensions T1 to Tn are generated on the interface of the wall surface and liquid 9, and the capillary force Fc, which is the resultant force thereof, is generated in the counterclockwise direction R2, i.e. in the direction from the inlet end portion 13 toward the inside of the supply chamber 6A. The value of the capillary force Fc can be represented by the following formula (1).

$$Fc = T \times \cos \theta c \times c \qquad (1)$$

The reference symbol "T" denotes a surface tension of water, "θc" denotes a contact angle of the liquid 9 to the wall surface of the fluid passage, and "c" denotes a circumferential length of the fluid passage.

As described above, the hydrophobic property of the inlet end portion 13 generates the capillary force Fc, which is a non-moistening phenomenon holding the liquid 9 in the supply chamber 6A at the inlet end portion 13. Further, the liquid passage 8A has to be a micro liquid passage for holding the liquid 9 in the inlet end portion 13 by the capillary force Fc. In the present embodiment, as described above, the width of the channel 8A is set to the range not less than 20 µm and not more than 2000 µm with the depth of the channel 8A smaller than that of the supply chamber 6A and target chamber 7A. Therefore, the liquid 9 can be reliably held in the inlet end portion 13 by the capillary force Fc.

Then, the application port 11 is sealed (step A') if it is necessary for preventing the liquid 9 from spattering during the rotation of the rotary substrate 2. As described above, providing the application port 11 closer to the rotary shaft 3 prevents spattering of the liquid caused by rotation. Further, the spattering is also prevented by making the opening area of the application port 11. sufficiently small by comparison with that of the supply chamber 6A, but this makes it difficult to fill the inside of the supply chamber 6A with the liquid 9 in the step A. Therefore, conduction of the step A' achieves both reliable application of the liquid 9 into the supply chamber 6A and the prevention of spattering of the liquid 9 during rotation of the rotary substrate 2.

Figure 7B:
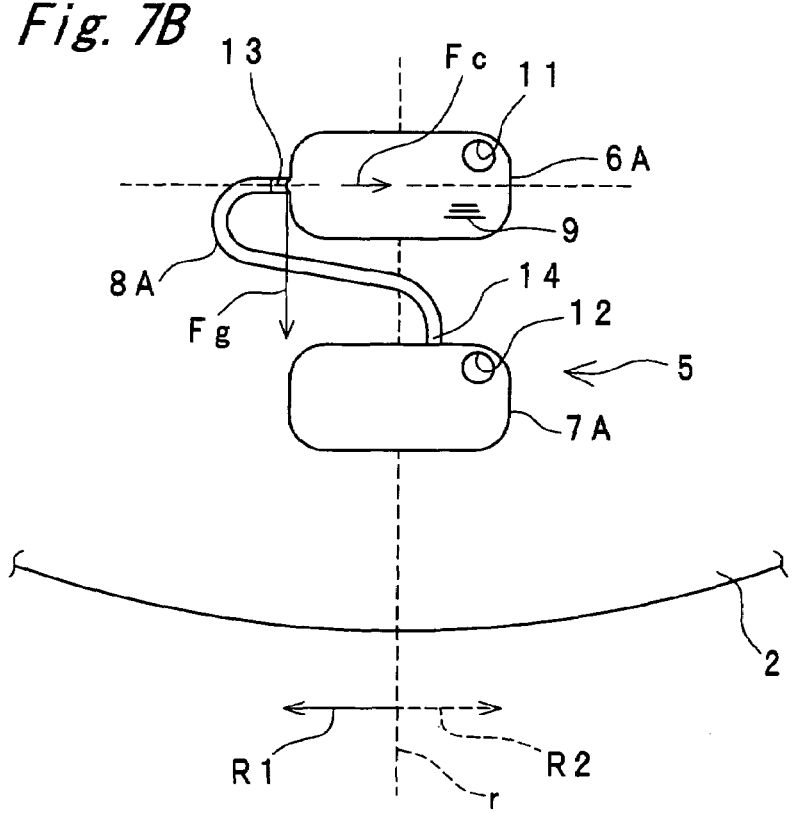
FIG. 7B is a schematic plan view for explaining the forces acting on the liquid in a fluid passage end portion while the rotary substrate rotates.

The rotary substrate 2 is then rotated in the clockwise direction R1 (direction in which the inlet end portion 13 extends from the supply chamber 6A) with a velocity characteristic 41 having a constant acceleration a1 (step B). Solid lines from the time 0 to the time t1 in FIG. 6 show the rotation velocity and rotation direction of the rotary substrate 2 in step B. The direction of acceleration a1 is the clockwise direction R1. The rotary substrate 2 starts rotating at the time 0. The rotation velocity of the rotary substrate 2 rises with the acceleration a1 and reaches the rotation velocity RV1 at the time t1. As shown in FIG. 7B, while the rotary substrate 2 rotates in the clockwise direction R1 in step B, an outwardly centrifugal force Fg acts in the radial direction r on the liquid 9 held by the capillary force Fc in the inlet end portion 13. However, the inlet end portion 13 extends in the clockwise direction R1, and the direction of the centrifugal force Fg is perpendicular to the extension direction of the inlet end portion 13. Therefore, despite the action of the centrifugal force Fg, the liquid 9 in the inlet end portion 13 is maintained in a state in which it is held by the capillary force Fc.

Then, the rotary substrate 2 being rotated according to the velocity characteristic 41 is subjected to abrupt braking according to a different velocity characteristic 42 having a constant acceleration a2 (step C). A solid line from the time t1 to the time t2 in FIG. 6 indicates the rotation velocity and rotation direction of the rotary substrate 2 in step C. The decrease in rotation velocity of the rotary substrate 2 starts from the rotation velocity RV1 at the time t1. The rotation velocity of the rotary substrate 2 decreases with the acceleration (deceleration if the clockwise direction R1 is considered as a positive direction) a2, and the rotation of the rotary substrate 2 in the clockwise direction R1 stops at the time t2. The velocity waveforms in steps B and C constitute a single triangular form. The direction of acceleration a1 in step B is a clockwise direction R1, whereas the direction of acceleration a2 in step C is the counterclockwise direction R2. In other words, the acceleration a2 of step C is opposite to the acceleration a1 of step B. Further, the absolute value of the acceleration a2 of step C is sufficiently larger than the absolute value of the acceleration a1 of step B.

Figure 7C:
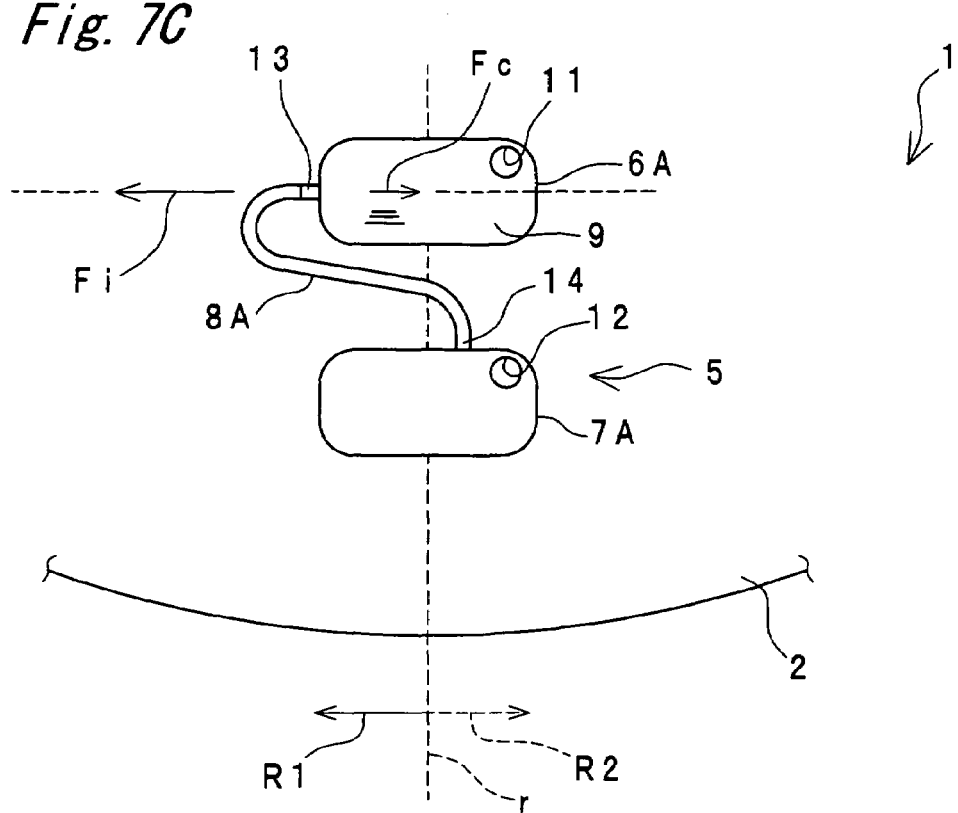
FIG. 7C is a schematic plan view for explaining the forces acting on the liquid in the fluid passage end portion when the rotary substrate is abruptly stopped.

Referring to FIG. 7C, an inertial force Fi acts on the liquid 9 in the inlet end portion 13 due to abrupt braking of the rotary substrate 2 in step C. Specifically, when the rotary substrate 2 that being rotated in the clockwise direction R1 in step B is abruptly braked in step C, the liquid 9 accommodated in the supply chamber 6A and held in the inlet end portion 13 will continue to move in the clockwise direction R1 according to the law of inertia. As a result, the inertial force Fi in the clockwise direction R1 acts on the liquid 9 held in the inlet end portion 13. The value of the inertial force Fi is proportional to the absolute value of acceleration a2 when the rotary substrate 2 is abruptly braked in step C. The inertial force Fi and acceleration a2 have a relationship represented by the following formula (2).

$$Fi = -m \times a2 \quad (2)$$

The reference symbol "m" denotes a mass of the liquid 9 held in the inlet end portion 13. The negative sign in the right side of the formula (2) indicates that the direction of the inertial force Fi is opposite to that of acceleration a2.

As described above, the inlet end portion 13 extends in the clockwise direction R1 from the supply chamber 6A, whereas the capillary force Fc acts in the counterclockwise direction R2. Therefore, the inertial force Fi acts on the liquid 9 so as to cancel the capillary force Fc and to get the fluid passage 8A wet with the liquid 9 in the inlet end portion 13. If the inertial force Fi becomes larger than the capillary force Fc holding the liquid 9 in the inlet end portion 13, that is, the inertial force Fi exceeds a pressure applied to a cross-sectional area of the inlet end portion 13, then the liquid 9 held in the inlet end portion 13 will flow into the channel 8A. Because the value of the inertial force Fi is proportional to the absolute value of acceleration a2 of step C as described above, for obtaining the inertial force Fi exceeding the capillary force Fc, the absolute value of acceleration a2 of step C needs to be large, in other words, the rotation velocity of the rotary substrate 2 in step C needs to rapidly decrease. On the other hand, because step B is executed in order to rotate the rotary substrate 2 in a stationary state with a certain rotation velocity RV1, it is not necessary to accelerate the rotary substrate 2 rapidly in step B. For those reasons, in the present embodiment, the acceleration a2 of step C is set sufficiently higher than the acceleration a1 of step B. For example, the acceleration a1 is set to a range not more than 600 rpm/sec, whereas the acceleration a2 is set to a range not less than 1000 rpm/sec and not more than 60,000 rpm/sec or less. The duration time of step B (from the time 0 to the time t1 in FIG. 6) is determined by the acceleration a1 and rotation velocity RV1 which is a finally attained velocity. Further, the duration time of step C (from the time t1 to the time t2 in FIG. 6) is determined by the acceleration a2 and rotation velocity RV1 at the start of deceleration. The following conditions are especially preferable. At step B, the acceleration a1 is set to 100 rpm/sec and acceleration is conducted for 30 sec (from the time t0 to the time t1). Then, when the rotation velocity reaches 3000 rpm, abrupt braking of step C is conducted. If the acceleration a2 of step C is set to about 6000 rpm/sec, then braking of the rotary substrate 2 is completed within 0.5 sec (the time interval from time t1 to t2 is 30.5 sec). With such velocity characteristics 41, 42, the liquid 9 having a volume of 1 µL to 10 µL can be delivered.

As described above, the entire channel 8A except for the inlet end portion 13, supply chamber 6A, and target chamber 7A have hydrophilic properties. Therefore, once holding of the liquid 9 in the inlet end portion 13 is released by the inertial force Fi, the liquid 9 in the supply chamber 6A flows through the channel 8A into the target chamber 7A due to the moistening effect and capillary phenomenon. The air present in the channel 8A and target chamber 7A is exhausted to the outside of the rotary substrate 2 through the air port 12. Because the liquid 9 spreads to the entirety of the channel 8A and target chamber 7A due to the capillary phenomenon, the liquid 9 can be quantitatively and reliably supplied to the target chamber 7A.

Figure 7D:
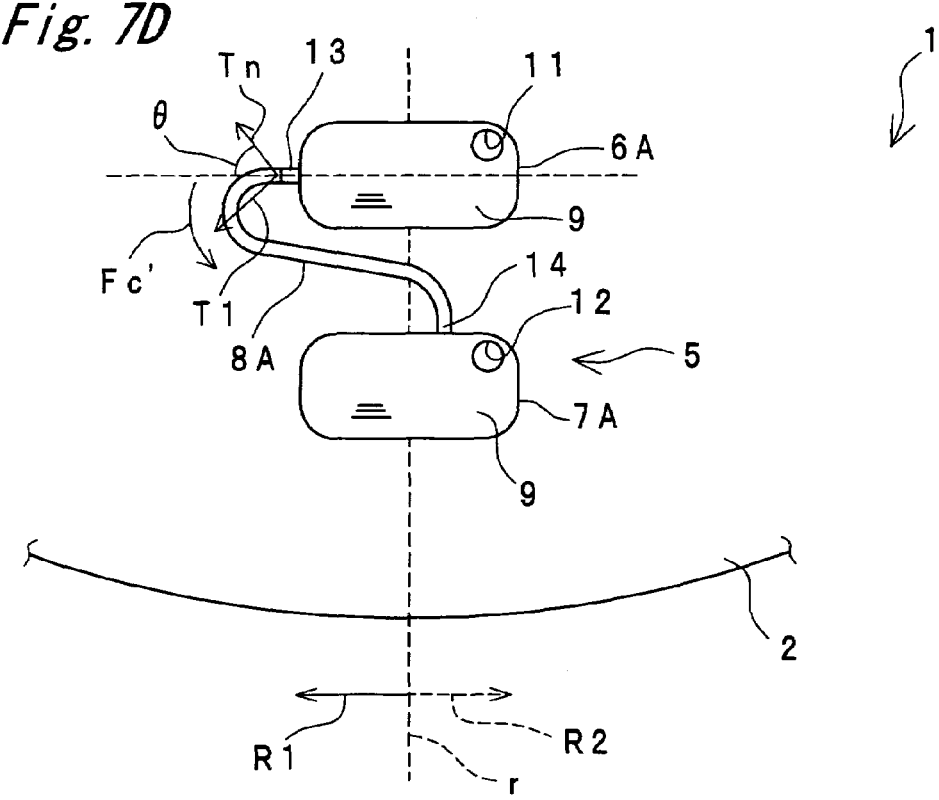
FIG. 7D is a schematic plan view for explaining the forces acting on the liquid in the fluid passage end portion while the liquid is delivered.

The capillary phenomenon will be described below in detail. As shown in FIG. 7D, when the channel wall surface of the channel 8A having hydrophilic property is wetted, the contact angle θc between the liquid and passage wall surface is an acute angle. Surface tension forces S1 to Sn are generated in the direction shown in FIG. 7D at the interface of the passage wall surface and liquid 9. The capillary force Fc', which is the resultant force of the surface tension forces S1 to Sn, is generated in the clockwise direction R1, i.e. in the direction in which the inlet end portion 13 extends from the supply chamber 6A. Therefore, if the holding of the liquid by the inlet end portion 13 is released, the capillary force Fc' acts on the liquid 9 so as that the liquid 9 flows into and occupies the channel 8A. The value of the capillary force Fc' is represented in the same manner as by the above-described formula (1).

The direction of the inlet end portion 13 will be described. In the present embodiment, the direction of the inlet end portion 13 is the clockwise direction R1. For assuring that the liquid 9 held in the inlet end portion 13 reliably flows into the channel 8A by the inertial force Fi due to the abrupt braking (step C), the inlet end portion 13 needs to extend along the clockwise direction R1 in which the inertial force Fi acts. Specifically, the direction of the inlet end portion 13 needs to be set so that the angle between the inlet end portion 13 and the clockwise direction R1 is not less than −45° and not more than +45°. This high flexibility in design relating the direction of the inlet end portion 13 is advantageous in view of productivity. Conversely, if the inlet end portion 13 extended perpendicularly to the clockwise direction R1, the inertial force F1 could not cause the liquid 9 held in the inlet end portion 13 to flow into the channel 8A.

The volume of the liquid 9 flowing from the supply chamber 6A to the target chamber 7A can be regulated by the position of the inlet end portion 13 with respect to the supply chamber 6A. For example, when the inlet end portion 13 is connected to the position on the outermost periphery in the radial direction "r" of the supply chamber 6A, almost all the liquid 9 in the supply chamber 6A will be delivered into the target chamber 7A via the channel 8A. This is because an outwardly centrifugal force in the radial direction "r" constantly acts on the liquid 9 in the supply chamber 6A due to that the rotary substrate 2 rotates in step B until immediately before the rotary substrate 2 is abruptly braked in step C. Differently to this arrangement, when the position of the inlet end portion 13 is shifted inwardly in the radial direction "r", i.e. toward the rotary shaft 3, the liquid 9 filling the supply chamber 6A, the liquid located on the outer periphery side with respect to the inlet end portion 13 will not be delivered to the target chamber 7A despite the abrupt braking of the rotary substrate 2. Such arrangement is useful when it is required to regulate the quantity of liquid to be delivered to the target chamber 7A. However, even the liquid 9 located on the outer side in the radial direction "r" with respect to the inlet end portion 13 can be delivered in a slight quantity to the target chamber 7A due to viscosity. Therefore, although the position of the inlet end portion 13 can not achieve strict quantitative accuracy of the liquid to be delivered to the target chamber 7A, it can regulate the volume of the liquid to be delivered with a certain level of accuracy.

The liquid delivery apparatus 1 of the present embodiment has various advantages listed below.

Firstly, the liquid 9 is delivered from the supply chamber 6A to the target chamber 7A via the channel 8A when the inertial force Fi, rather than the centrifugal force, exceeds the capillary force Fc holding the liquid 9 in the inlet end portion 13. Therefore, the inlet end portion 13 constituting a boundary between the supply chamber 6A and channel 8A is not required to be arranged on the outer side with respect to the supply chamber 6A, that is, in the farthest position from the rotary shaft 3 than the supply chamber 6A. This increases flexibility relating to the arrangement of the supply chamber 6A, target chamber 7A, and fluid passage 8A.

Secondly, in case that a centrifugal force serves as a drive force, the liquid delivery can be achieved only in one direction, in the centrifugal direction away from the supply side chamber and increasing the distance from the central axis of rotation. By contrast, in the liquid delivery apparatus 1 of the present embodiment, the extension direction of the inlet end portion 13 is set in the clockwise direction R1 coincided with the inertial force Fi. Further, as will be explained hereinafter with reference to FIG. 30, the extension direction of the inlet end portion 13 can be set in the counterclockwise direction R2 merely by changing the sequence of rotation drive of the rotary substrate 2. Therefore, the liquid can be delivered in any of the two directions, i.e. clockwise direction R1 and counterclockwise direction R2, from the supply chamber 6A by setting the extension direction of the inlet end portion 13 in any of those two directions. In other words, the liquid delivery apparatus 1 of the present embodiment realizes the liquid delivery behavior control with a high flexibility which is not limited to one direction.

Thirdly, the liquid flow from the supply chamber 6A to the target chamber 7A through the fluid passage 8A caused by the inertial force Fi exceeding the capillary force Fc encounters with flow resistance from fluid passage walls. The flow resistance acts as a component reducing a velocity of the liquid flow. However, because the flow resistance is less than the applied inertial force Fi in the fluid passage 8A which is a minute or micro passages, the liquid 9 can be delivered in any direction from the supply chamber 6A. In other words, as described latter in detail with reference to FIG. 31, the target chamber 7A can be arranged closer to the rotary shaft 3 than the supply chamber 6A to deliver the liquid 9 in the centripetal direction from the supply chamber 6A. This realizes a more complex liquid delivery and increased design flexibility, thereby facilitating the design of liquid delivery apparatus.

The sequence for rotating the rotary substrate 2 is not limited to those shown in FIG. 5 and FIG. 6. Possible alternatives of the sequence are presented below.

FIG. 8 and FIG. 9 illustrate a first alternative of the rotation drive sequence. In this alternative, a step where the acceleration is 0, that is, a step D where the rotary substrate 2 is rotated for a given length of time at a constant rotation velocity RV1 is executed (from the time t1 to the time t2 in FIG. 9) between step B where the rotary substrate 2 is rotated in the clockwise direction (from the time t0 to the time t1 in FIG. 9) and step C where the rotary substrate 2 is abruptly braked (from the time t2 to the time t3 in FIG. 9). After the constant-velocity rotation has been maintained in step D, the liquid 9 is delivered by the inertial force Fi generated due to the abrupt braking in step C. In measurement of the quantity of proteins in blood, the blood (sample) is separated into blood cells (particulate component) and blood plasma (liquid component), as a preliminary process for the measurement. Then only a solution having dissolved therein the proteins contained in the blood plasma has to be delivered. The rotation drive shown sequence shown in FIGS. 8 and 9 is suitable for a more complex liquid delivery control of this type. Specifically, rotating the rotary substrate 2 at the constant velocity for a given length of time in step D can separate blood into blood cells and blood plasma, and only the blood plasma component can be delivered in step C after the separation. Instead of the step D, the rotary substrate 2 may be rotated for a given length of time with acceleration different from the acceleration a1, a2 of steps B and C.

Figure 10:
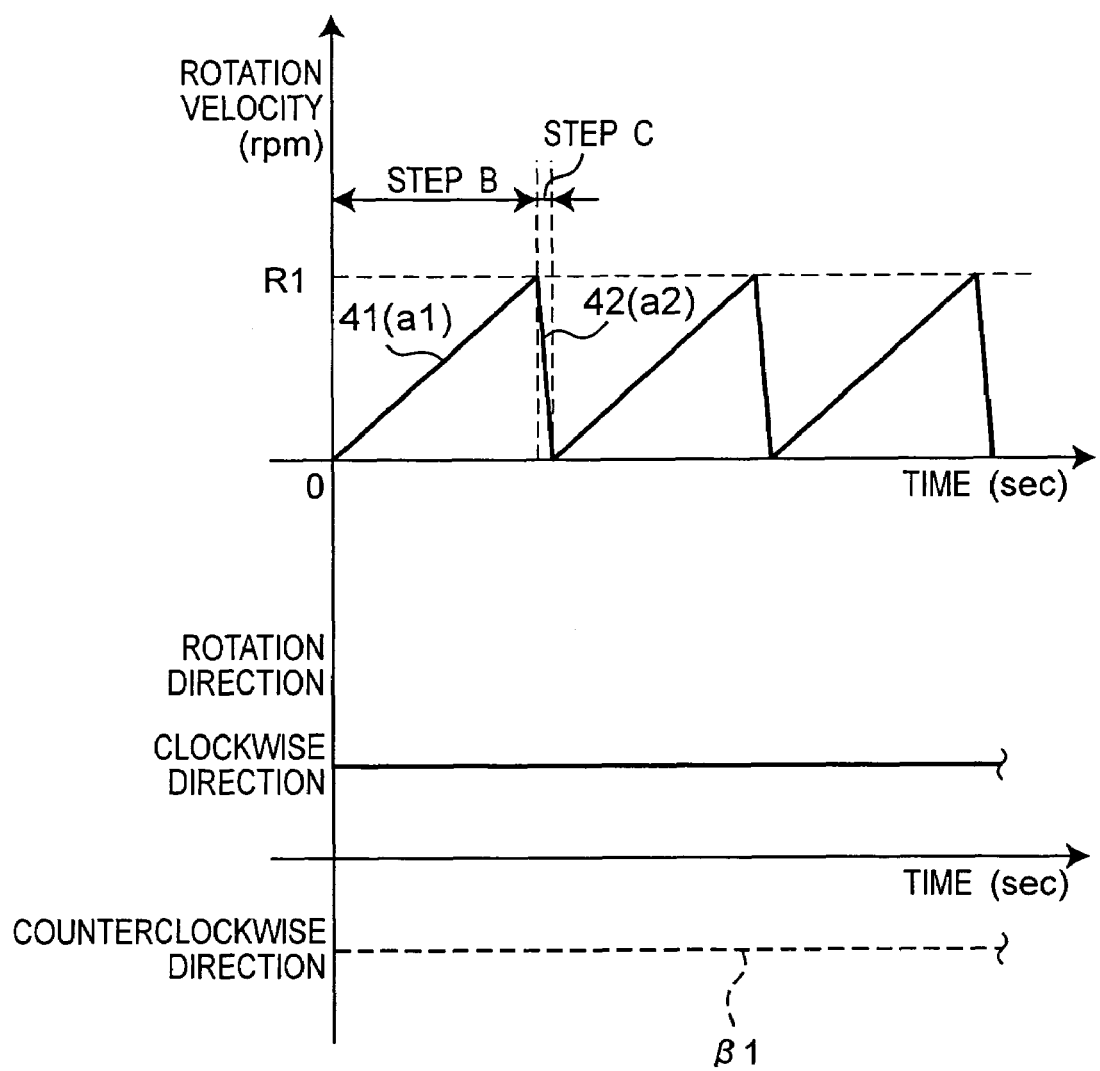
FIG. 10 is a diagram illustrating a velocity waveform and rotation direction of a third example of the operation of the liquid delivery apparatus according to the first embodiment of the present invention.

FIG. 10 illustrates a velocity waveform and rotation direction of a second alternative of the rotation drive sequence. In the second alternative, as shown schematically with a broken line α1 in FIG. 5, the step B where the rotary substrate 2 is rotated in the clockwise direction R1 and the step C where the rotary substrate 2 is abruptly braked are repeated. As a result, the velocity waveform of the rotary substrate 2 has a sawtooth appearance comprising continuously repeated triangular waves. In case that the volume of the liquid 9 accommodated in the supply chamber 6A is larger than the total volume of the fluid passage 8A, rotation drive of the rotary substrate 2 according to the second alternative can achieve intermittently continuous delivery of the liquid 9 from the supply chamber 6A to the target chamber 7A. Therefore, the sequence of the second alternative is effective when relatively large volume of liquid 9 is delivered from the supply chamber 6A to the target chamber 7A.

Figure 11:
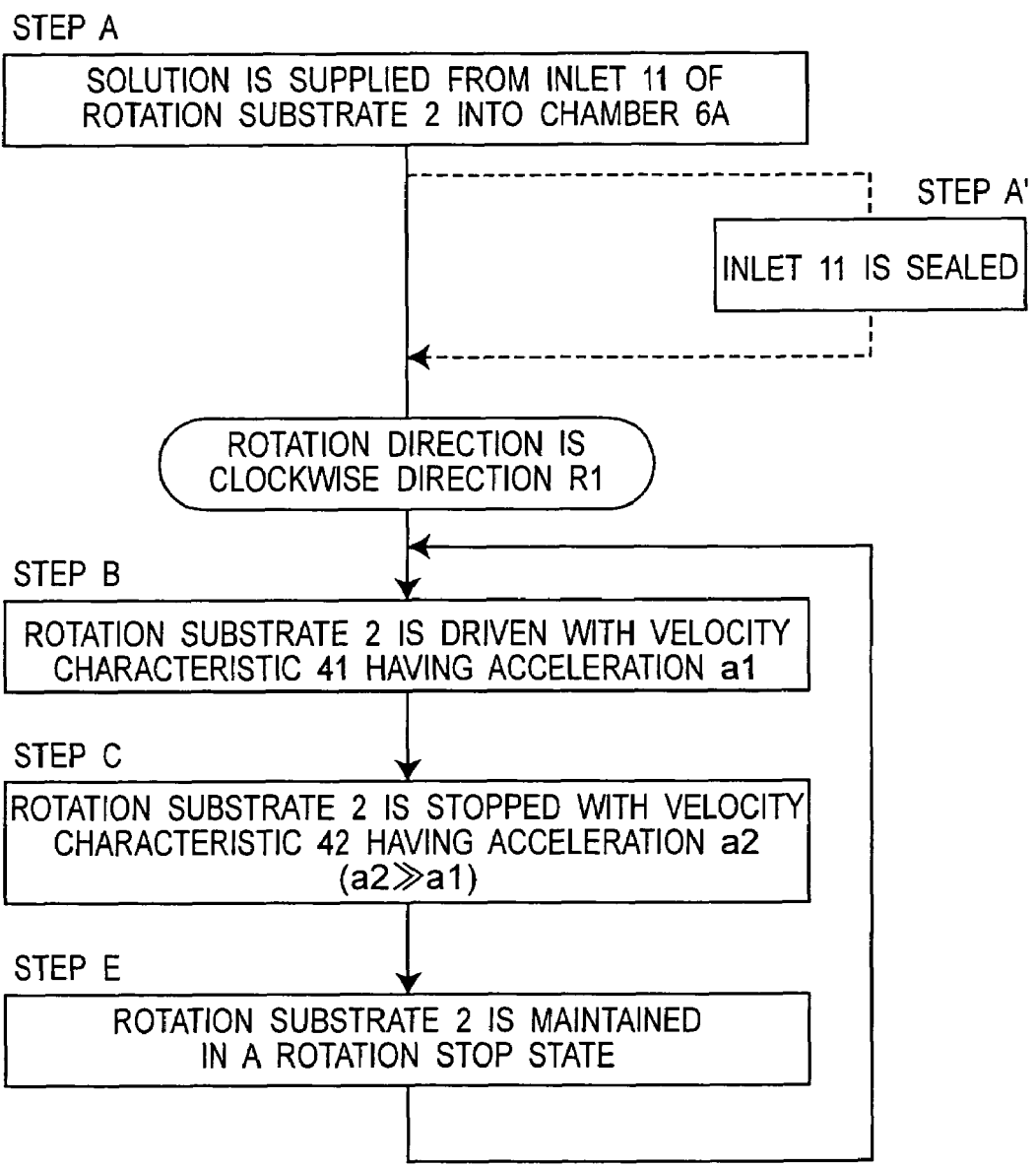
FIG. 11 is a flowchart for explaining a fourth example of the operation of the liquid delivery apparatus according to the first embodiment of the present invention.
Figure 12:
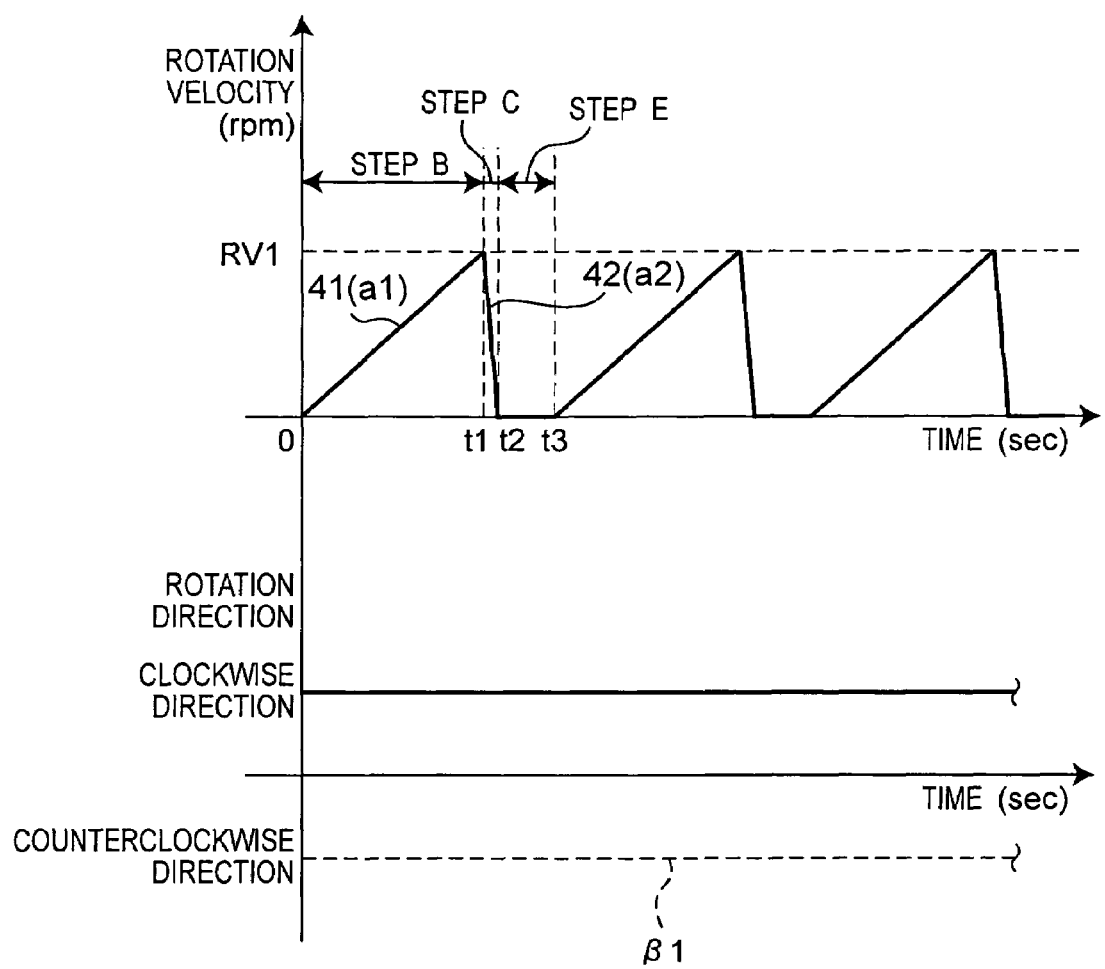
FIG. 12 is a diagram illustrating a velocity waveform and rotation direction of a fourth example of the operation of the liquid delivery apparatus according to the first embodiment of the present invention.

FIGS. 11 and 12 illustrate a third alternative of the sequence of rotation drive. In the third alternative, the step B where the rotary substrate 2 is rotated in the clockwise direction R1 (from the time 0 to the time t1 in FIG. 12) and step C where the rotary substrate 2 is abruptly braked (from the time t1 to the time t2 in FIG. 12) are repeated with execution of an interval step E (from the time instant t2 to the time instant t3 in FIG. 12), where the rotation of the rotary substrate 2 is halted for a given length of time, each time steps B and C are completed. For example, after the liquid 9 has been delivered from the supply chamber 6A to the target chamber 7A in step B, the delivered liquid 9 and an enzyme previously supported in the target chamber 7A can be reacted during the time interval by step E. Instead of the step E, the rotary substrate 2 may be rotated at a constant low velocity for a given time interval each time the steps B and C are completed.

Figure 13:
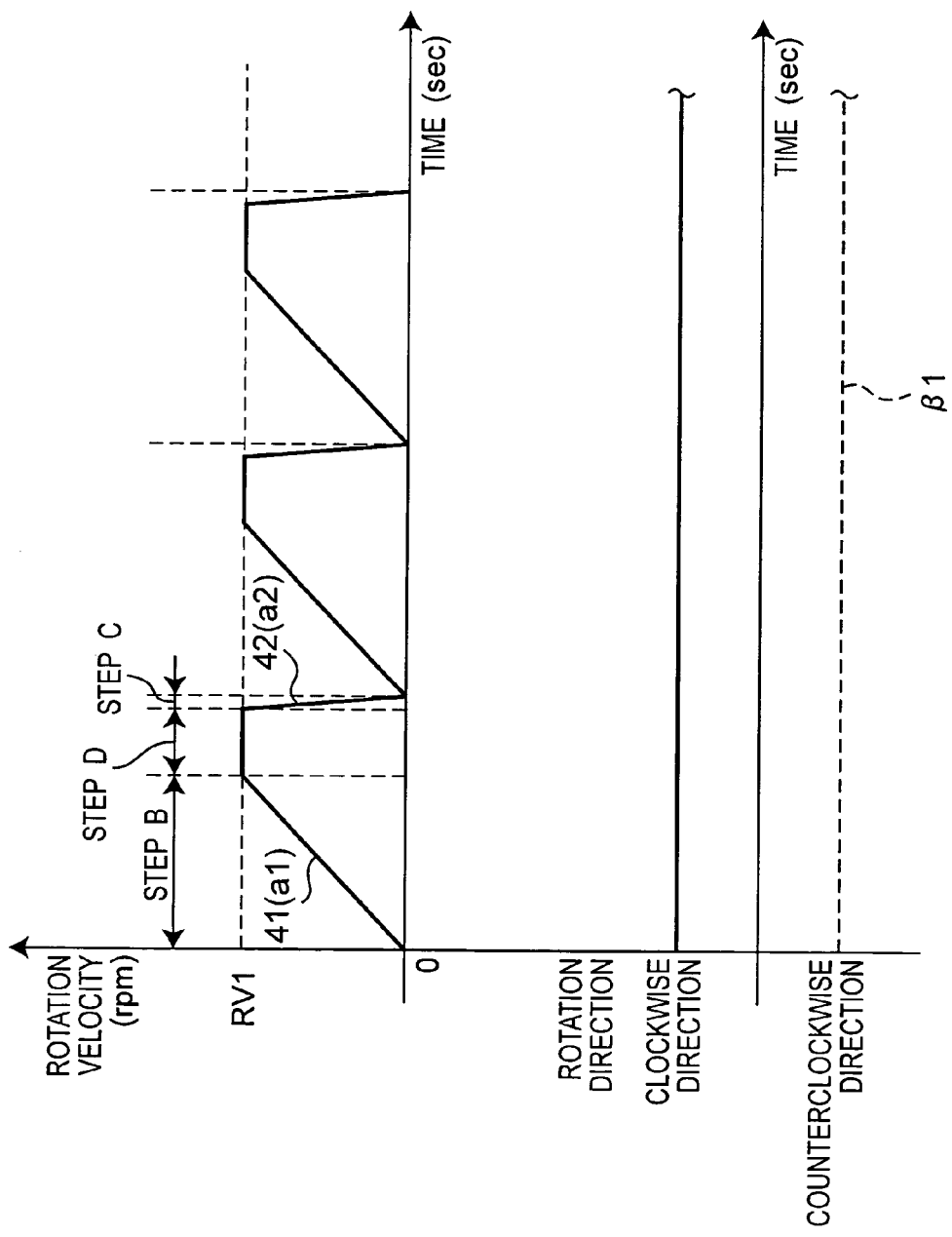
FIG. 13 is a diagram illustrating a velocity waveform and rotation direction of a fifth example of the operation of the liquid delivery apparatus according to the first embodiment of the present invention.

FIG. 13 illustrates a velocity waveform and rotation direction of a fourth alternative of the rotation drive sequence. In the fourth alternative, as shown schematically by the broken line α2 in FIG. 8, the step B, step D, and step C are continuously repeated in this order.

Figure 15:
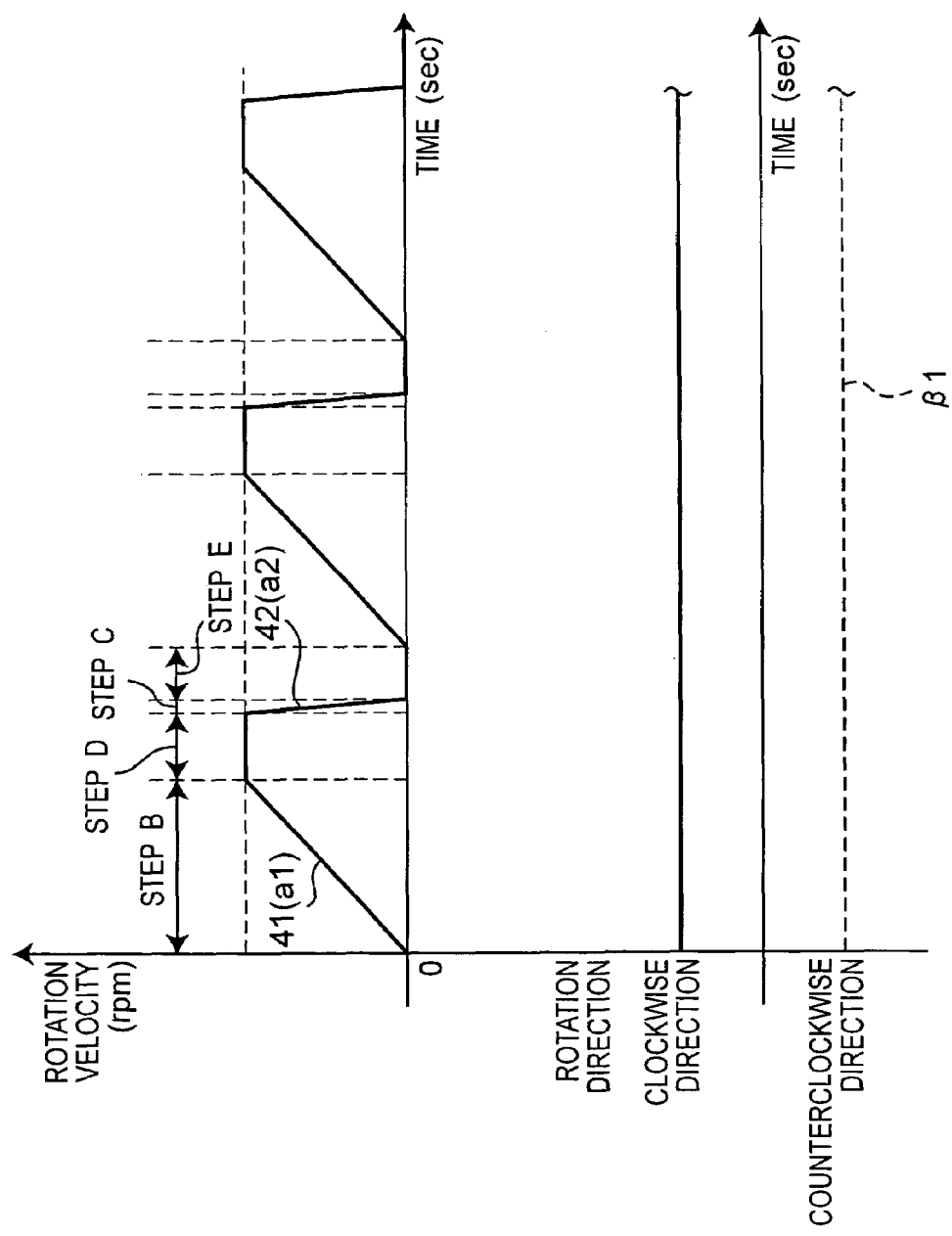
FIG. 15 is a diagram illustrating the velocity waveform and rotation direction of the sixth example of the operation of the liquid delivery apparatus according to the first embodiment of the present invention.

In a fifth alternative of the rotation drive sequence shown in FIGS. 14 and 15, the step B, step D, step C, and step E are continuously repeated in this order.

In the above description, the rotation of the rotary substrate 2 in both the steps B and C is a uniform accelerated motion. However, the acceleration of rotation of the rotary substrate 2 in those steps can be fluctuated, as long as the inertial force Fi exceeding the capillary force Fc is generated.

Various alternatives relating to the structure of the liquid delivery apparatus 1 will be described below. Those alternatives are not limited to the first embodiments and are also applicable to second to tenth embodiments described latter.

The external shape of the rotary substrate 2 is not limited to a disk and the rotary substrate can be in the form of a cube, rectangular parallelepiped, polygonal including pentagonal, or star-like shape. The shape of the supply chamber 6A and target chamber 7A is not limited to an almost rectangular shape and can be any shape such as a cylindrical rod-like shape.

The cross-sectional shape of the application port 11 and air port 12 is not limited to a circle and can have another shape such as an elliptical or polygonal shape. The application port 11 is not limited to the passage passing through from the upper wall of the supply chamber 6A to the top surface of the rotary substrate 2 and may be arranged in any location. Further, the air port 12 is not limited to the passage connecting the inside of the target chamber 7A to the outside of the rotary substrate 2 and may be formed by attaching a material that is permeable to air but impermeable to liquid to a portion of the wall surface constituting the target chamber 7A or fluid passage 8A. By adopting such arrangement, the air port 12 can have a relatively large area because the leak of liquid 9 through the air port 12 during rotation of the rotary substrate 2 does not have to be taken into account.

Alternatives of the laminated structure of the rotary substrate 2 will be described below.

Figure 16:
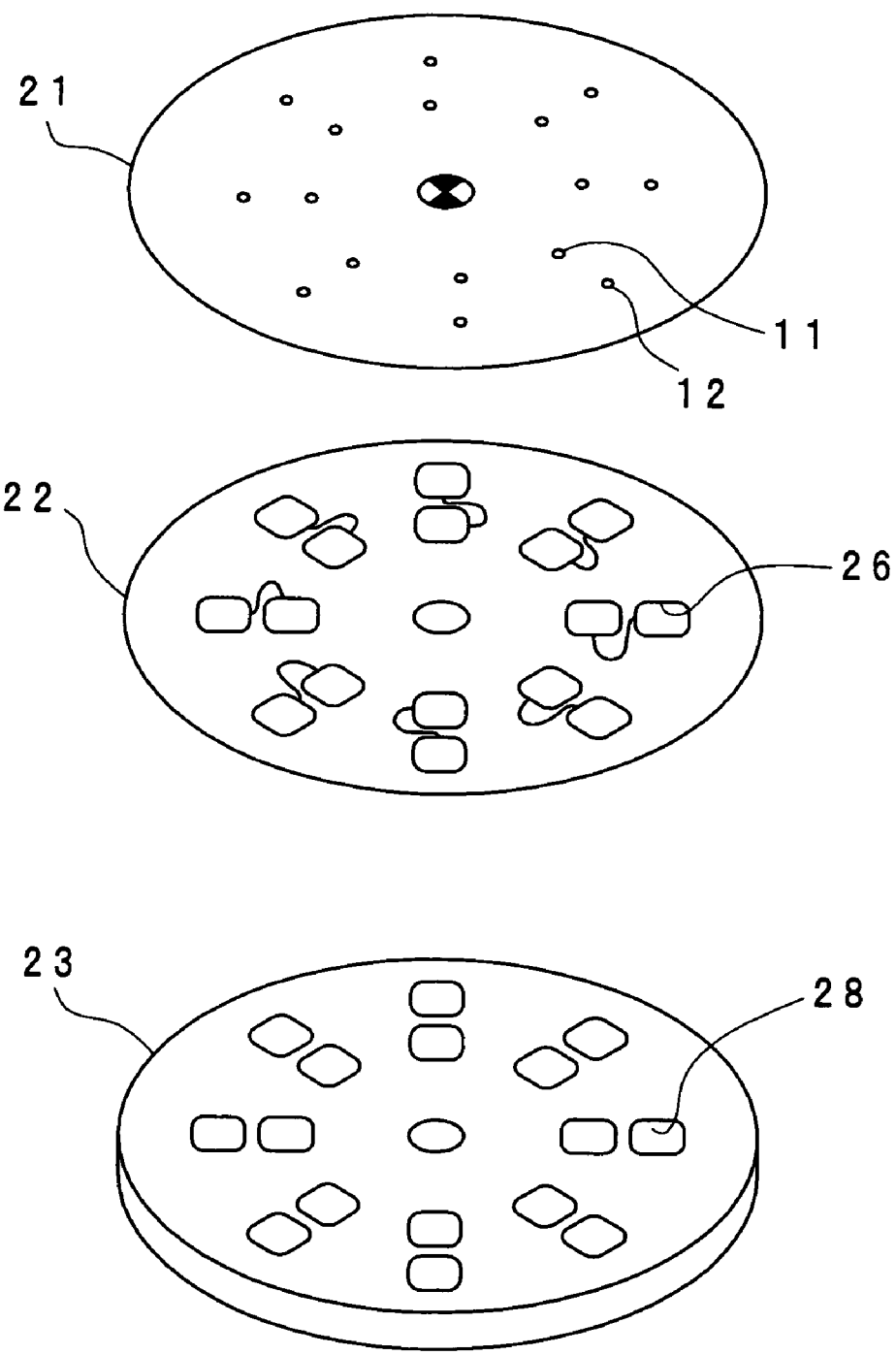
FIG. 16 is an exploded perspective view illustrating a first alternative of the rotary substrate.

The rotary substrate 2 of a first alternative shown in FIG. 16 has a three-layer structure comprising the upper surface substrate 21, fluid passage substrate 22, and chamber substrate 23. The application ports 11 and air ports 12 are provided in the upper surface substrate 21. The groove holes 26 having the shape corresponding to the supply chamber 6A, target chamber 7A, and fluid passage 8A are provided in the channel substrate 22. Recesses 28 having a bottom and corresponding to the supply chamber 6A and target chamber 7A are provided in the chamber substrate 23.

Figure 17:
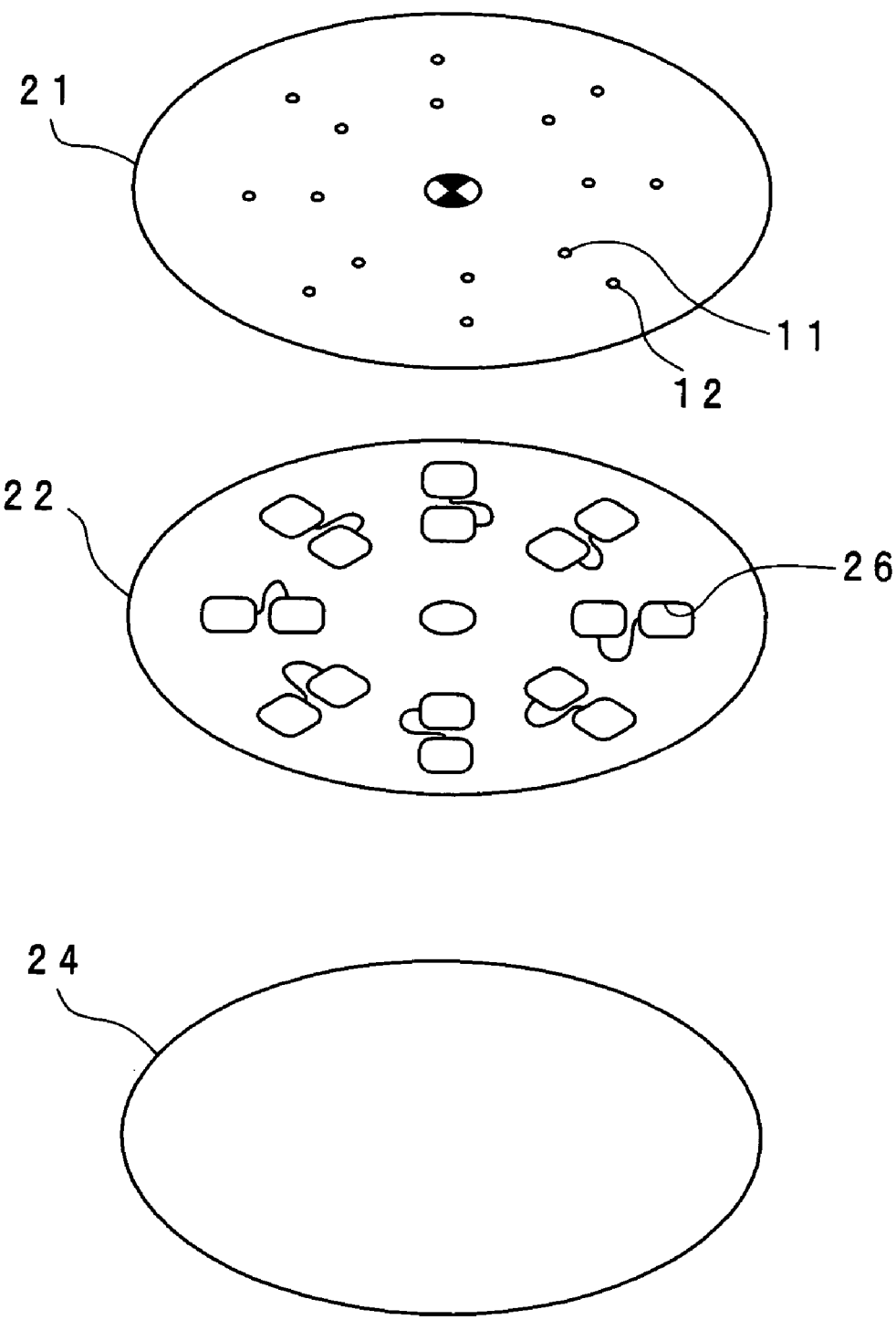
FIG. 17 is an exploded perspective view illustrating a second alternative of the rotary substrate.

The rotary substrate 2 of a second alternative shown in FIG. 17 has a three-layer structure comprising the upper surface substrate 21 provided with the application ports 11 and air ports 12, fluid passage substrate 22 provided with grooves hole 26 passing through in the thickness direction, and lower surface substrate 24 serving as a bottom portion for each of the supply chambers 6A and target chambers 7A.

Figure 18:
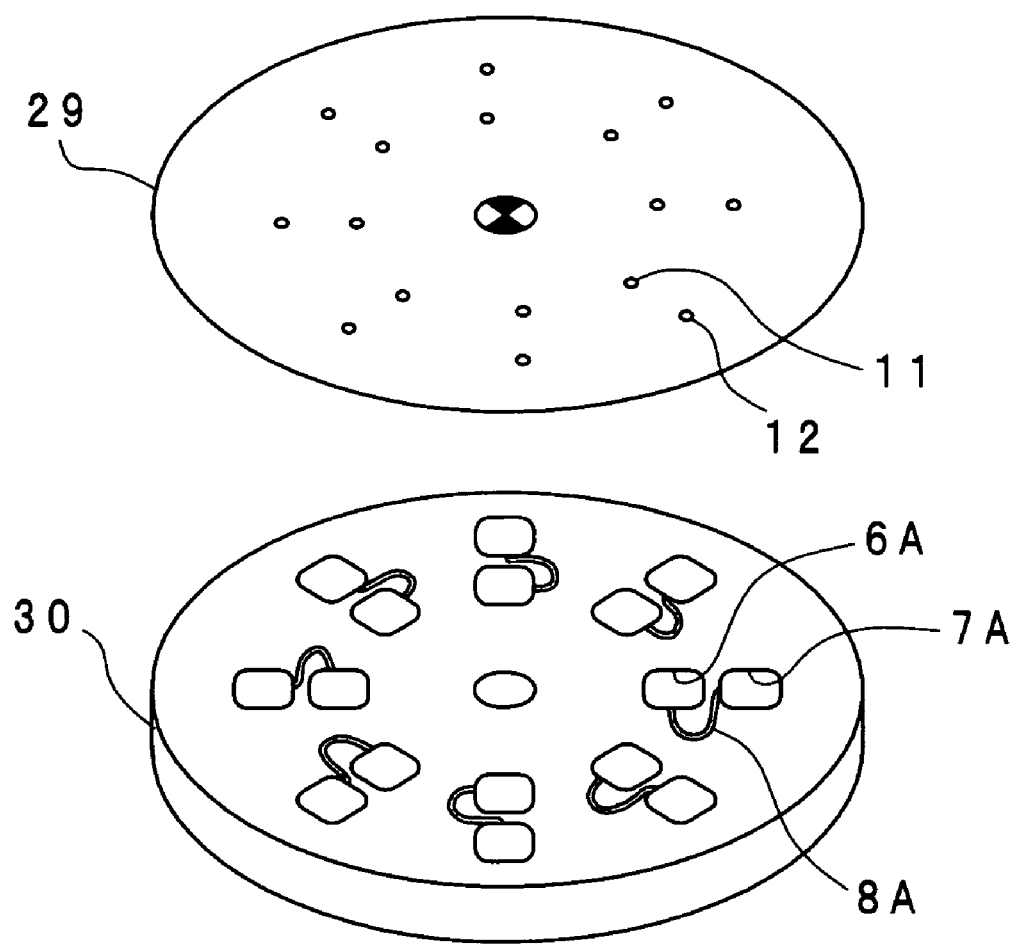
FIG. 18 is an exploded perspective view illustrating a third alternative of the rotary substrate.

The rotary substrate 2 of a third alternative shown in FIG. 18 has a two-layer structure comprising an upper substrate 29 provided with application ports 11 and an air ports 12 and a lower substrate 30 provided with the supply chambers 6A, target chambers 7A, and fluid passages 8A.

An example of the method for fabricating the rotary substrate 2 of the third alternative by photolithographic process will be described. This fabrication process comprises a step of coating a photoresist on the lower substrate 30 and forming the fluid passages 8A by lithography, a step of forming the supply chambers 6A and target chambers 7A, a step of forming the application ports 11 and air ports 12 in the upper substrate 29, and a step of sealing the upper openings of the passage sites 5 of the lower substrate 30 with the upper substrate 19. The process will be successively explained below starting from the step of forming the fluid passages 8A. A negative thick-film photoresist is coated on a glass substrate that has been cleaned. The photoresist is selected according to a size of the fluid passage. For example, KMPR1030 (manufactured by Kayaku Microchem Corp.) is preferable as the photoresist in view of suitability for forming thick film and aspect ratio. A rotation coating system such as a spin coater can be used. When the KMPR1030 is spin coated by a spin coater, pre-rotation operation is conducted for 10 seconds at 500 rpm and main rotation operation is conducted for 30 seconds at 1000 rpm. The film thickness can be changed by regulating the rotation speed at the main rotation process. For example, a thickness of 57 µm and 48 µm can be obtained respectively by rotation speeds during the main rotation process of 1000 rpm and 1070 rpm. Then, pre-baking is conducted for 20 minutes at a temperature of 95° C. and exposure is conducted by using a mask formed with passages and chambers. The exposure intensity and exposure time are appropriately corrected according to the film thickness. For example, the preferable exposure intensity is approximately 1700 mJ/cm$^2$. Then, PEB (Post Exposure Bake) for 6 minutes at a temperature of 95° C. and development are executed, thereby patterns of fluid passages and chambers being formed by photolithography. The chamber sites of the lower substrate 30 are then formed by cutting or sand blasting. Finally, the upper substrate 29 having the application ports 11 and air ports 12 is bonded onto the lower substrate 30.

Alternatives relating to the wettablity of the supply chamber 6A, target chamber 7A, and fluid passage 8A will be described below.

As the first alternative, in order to improve productivity, not only the inlet end portion 13 but the entirety of the channel 8A may have hydrophobic property. By this arrangement, not only the liquid 9 can be more reliably held by the inlet end portion 13, but the liquid 9 can be held over the entire length of the channel 8A. Further, the longer is the channel 8A, the more rigidly can the liquid 9 be held inside the supply chamber 6A. Therefore, when the entirety of the fluid passage 8A has hydrophobic property, for delivering a certain quantity of the liquid 9 from the supply chamber 6A to the target chamber 7A, it is necessary to repeat the step for generating the inertial force as shown in FIG. 10, FIG. 12, FIG. 13, and FIG. 15. A more accurately determined amount of liquid 9 can be delivered from the supply chamber 6A to the target chamber 7A by controlling the number of repetition cycles. Further, by adjusting the duration time of repeating the steps for generating the inertial force, it is possible to control the time required for delivering the determined quantity of liquid 9 from the supply chamber 6A to the target chamber 7A. This control of the time required for delivering the liquid is suitable for liquid delivery in case that mixing is carried out and after the predetermined reaction time another mixing is further carried out.

As a second alternative, the entirety of the passage site 5 may have hydrophobic property. Because the entirety of the passage site 5 can be composed of a hydrophobic material or the entirety of the passage site 5 can be subjected to a treatment providing it with hydrophobic property, productivity can be increased.

Further, as a third alternative, the entirety of the rotary substrate 2 may have hydrophobic property. Because the entirety of the rotary substrate 2 can be composed of a hydrophobic material or the entirety of the rotary substrate 2 can be subjected to a treatment providing it with hydrophobic properties, productivity can be increased.

Second Embodiment

The structure of a liquid delivery apparatus 1 according to a second embodiment of the present invention is same as that of the first embodiment described with reference to FIGS. 1 to 4. Therefore, in the following description, those figures will be referred to. In the liquid delivery apparatus 1 according to the second embodiment, the steps or sequences for rotating the rotary substrate 2 executed by the rotary drive unit 4 are different from those of the first embodiment. This difference will be generally described. In the first embodiment, the rotary drive unit 4 rotates the rotary substrate 2 in the clockwise direction R1 coincide with the extension direction of the inlet end portion 13 (step B) followed by abrupt braking of this rotation for generating the inertial force Fi that releases the liquid 9 held by the inlet end portion 13. Contrarily, in the second embodiment, the rotary drive unit 4 rotates the rotary substrate rapidly (with rapid acceleration) in the counterclockwise direction R2 opposite to the extension direction of the inlet end portion 13, thereby generating the inertial force Fi for releasing the liquid 9 held by the inlet end portion 13.

Figure 21A:
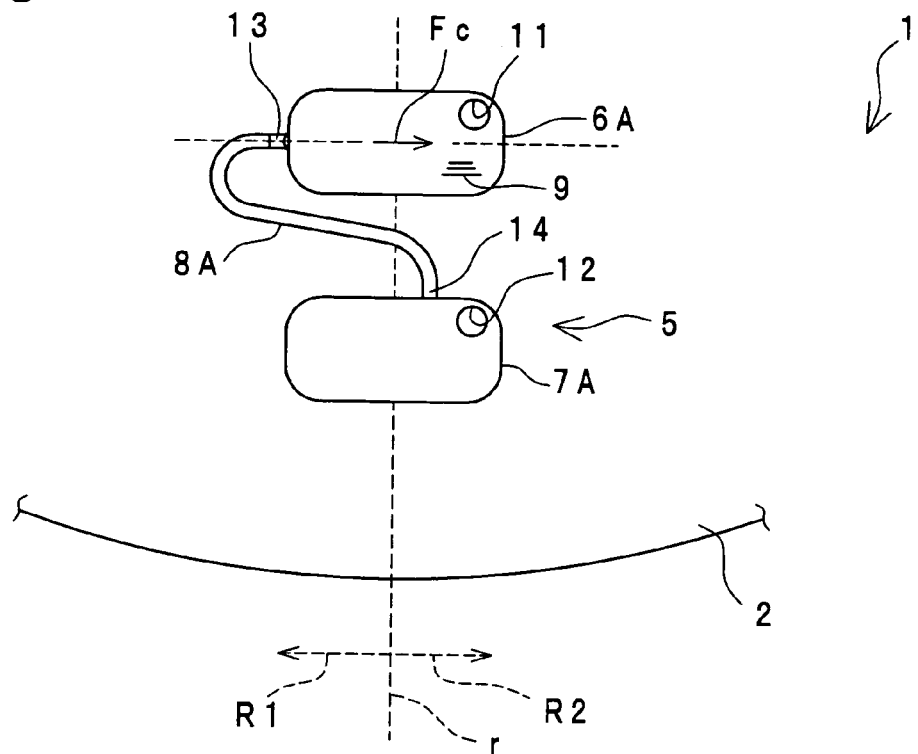
FIG. 21A is a schematic plan view for explaining the forces acting on the liquid in the fluid passage end portion before the rotation of the rotary substrate starts.

A liquid delivery method using the liquid delivery apparatus 1 according to the second embodiment will be described. Referring to a flowchart shown in FIG. 19, the liquid 9 is applied from the application port 11 of the rotary substrate 2 so that the supply chamber 6A is filled with the liquid 9 (step A). If necessary, the application port 11 is then sealed. Referring to FIG. 21A, because the inlet end portion 13 has hydrophobic property, the capillary force Fc in the counterclockwise direction Rc opposite to the extension direction of the inlet end portion 13 (clockwise direction R1) acts on the liquid 9 in the inlet end portion 13. The liquid 9 in the supply chamber 6A is held in the inlet end portion 13 by the capillary force Fc.

Then, the rotary substrate 2 in a stationary state is rapidly rotated in the counterclockwise direction R2 (direction opposite to the extension direction of the inlet end portion 13 from the supply chamber 6A) with a velocity characteristic 43 having a constant acceleration b1 (step F).

Figure 20:
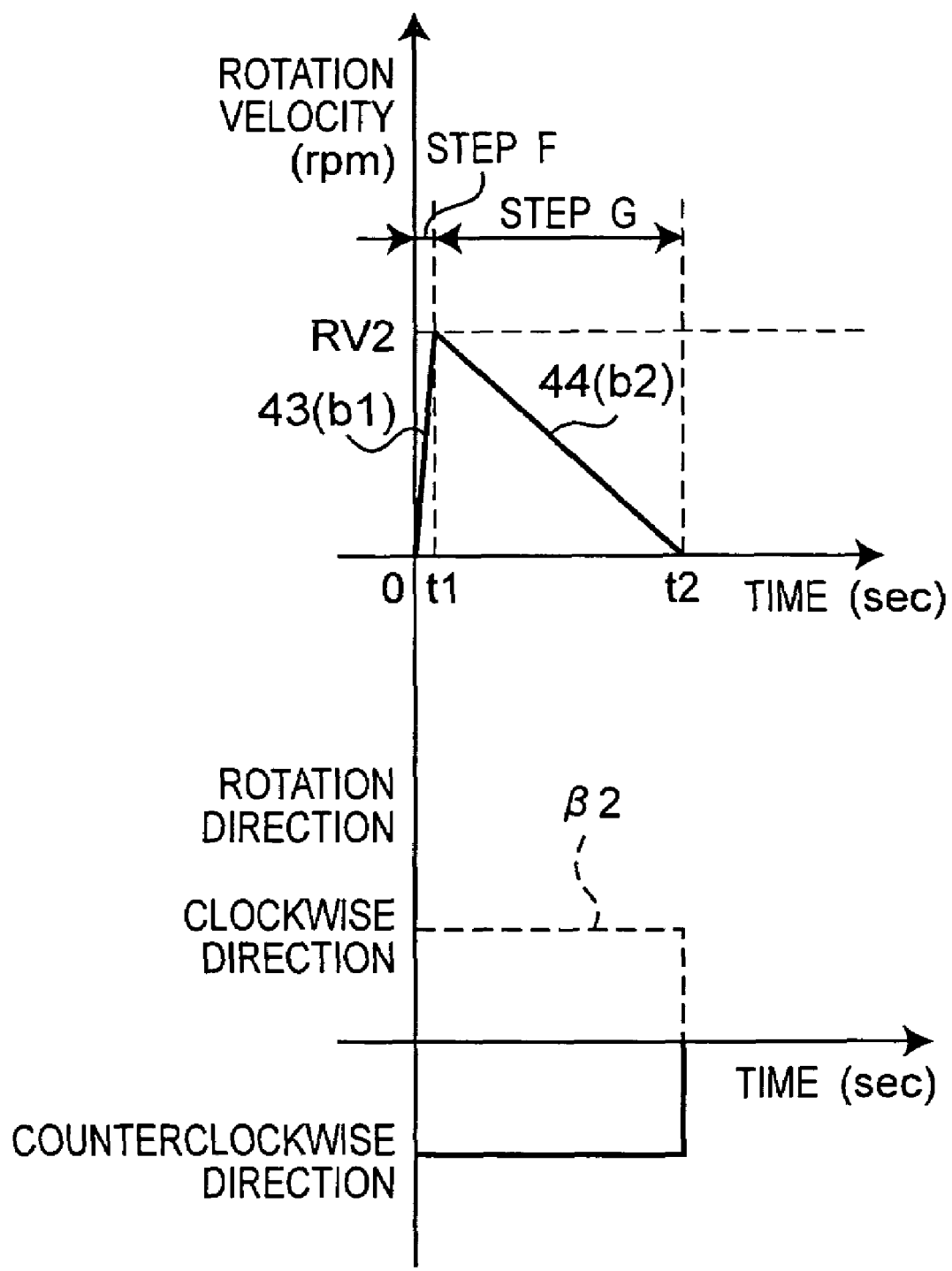
FIG. 20 is a diagram illustrating a velocity waveform and rotation direction of the first example of the operation of the liquid delivery apparatus according to the second embodiment of the present invention.
Figure 21B:
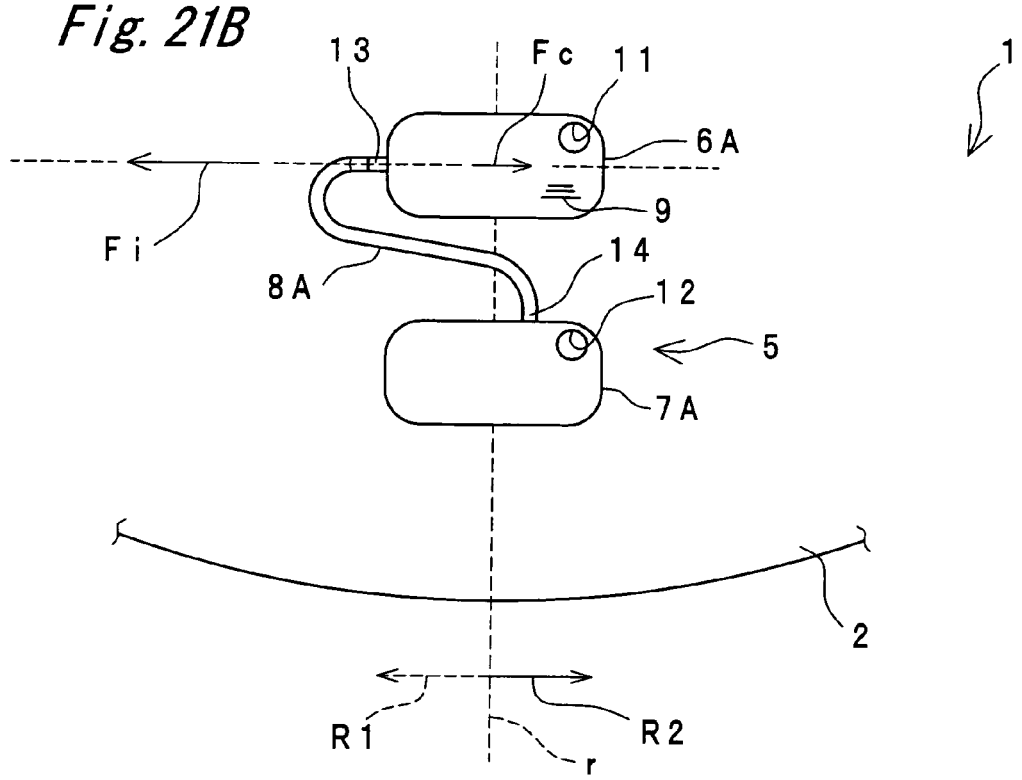
FIG. 21B is a schematic plan view for explaining the forces acting on the liquid in the fluid passage end portion when the rotary substrate is rapidly rotated.
Figure 21C:
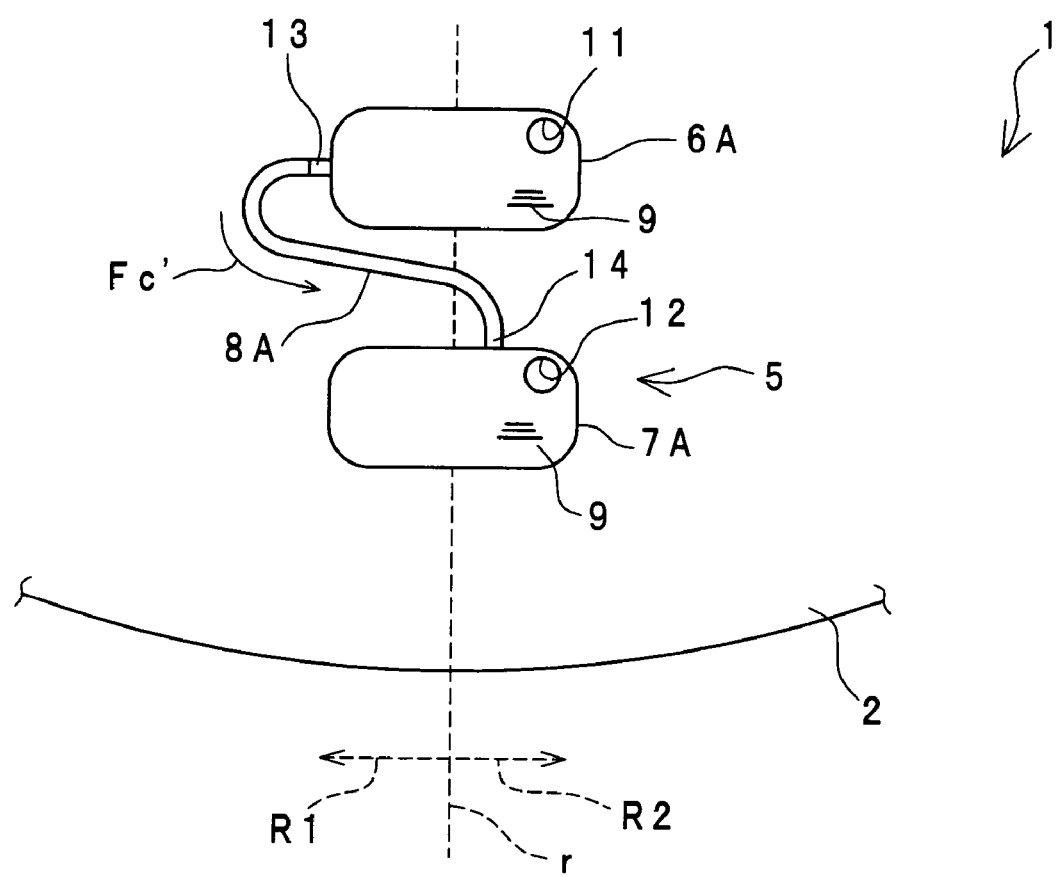
FIG. 21C is a schematic plan view for explaining the forces acting on the liquid in the fluid passage end portion when the liquid is delivered.

Solid lines from the time 0 to the time t1 in FIG. 20 show the rotation velocity and rotation direction of the rotary substrate 2 in step F. The direction of acceleration b1 is the counterclockwise direction R2. The rotary substrate 2 starts rotating at the time instant 0. The rotation velocity of the rotary substrate 2 rises with the acceleration b1 and reaches the rotation velocity RV2 at the time t1. As shown in FIG. 21B, due to the rotation in the counterclockwise direction R2, the inertial force Fi acts on the liquid in the inlet end portion 13. Specifically, when the rotary substrate 2 starts rotating in the counterclockwise direction R2, the liquid 9 accommodated in the supply chamber 6A and held in the inlet end portion 13 will maintain the stationary state due to the law of inertia. As a result, the inertial force Fi in the clockwise direction R1 acts on the liquid 9 held in the inlet end portion 13. The value of the inertial force Fi is proportional to the absolute value of the acceleration b1 during the rotation of the rotary substrate 2 in step F. The inertial force Fi acts on the liquid 9 so as to cancel the capillary force Fc and to get the fluid passage 8A wet with the liquid 9 in the inlet end portion 13. If the inertial force Fi becomes larger than the capillary force Fc holding the liquid 9 in the inlet end portion 13, then the liquid 9 held in the inlet end portion 13 will flow into the channel 8A. Because the fluid passage 8A and supply chamber 6A have hydrophobic property, once the holding of liquid in the inlet end portion 13 is released, the capillary force Fc' toward the target chamber 7A acts on the liquid 9 as shown in FIG. 21C. Because the liquid 9 spreads to the entirety of the channel 8A and target chamber 7A due to the capillary phenomenon, the liquid 9 can be quantitatively and reliably supplied to the target chamber 7A.

Then, the rotary substrate 2 is braked according to a velocity characteristic 44 having a constant acceleration b2 (step G). Solid lines from the time t1 to the time t2 in FIG. 20 show the rotation velocity and rotation direction of the rotary substrate 2 in step G. The decrease in rotation velocity of the rotary substrate 2 starts from the rotation velocity RV2 at the time instant t1. The rotation velocity of the rotary substrate 2 decreases with the acceleration (deceleration if the counterclockwise direction R2 is considered as a positive direction) b2, and the rotation of the rotary substrate 2 in the counterclockwise direction R2 stops at the time t2. The direction of acceleration b1 in step F is the counterclockwise direction R2, whereas the direction of the acceleration b2 in step G is the clockwise direction R1. In other words, the acceleration b2 of step G is opposite to the acceleration b1 of step F.

The value of the inertial force Fi is proportional to the absolute value of the acceleration b1 of step F. Therefore, for the inertial force Fi to exceed the capillary force Fc, the absolute value of the acceleration b1 of step F needs to be large, in other words, the rotary substrate 2 needs to be rapidly rotated. On the other hand, because step G is executed for only stopping the rotation of the rotary substrate 2, rapid decrease in rotation velocity during step G is not necessary. For those reasons, in the present embodiment, the acceleration b1 of step F is set sufficiently larger than the acceleration b2 of step G. For example, the acceleration b1 is set to a range not less than 1000 rpm/sec and not more than 60,000 rpm/sec, the acceleration b2 is set to a range not more than 600 rpm/sec. The duration time of step F (from the time 0 to the time t1 in FIG. 20) is determined by the rotation velocity RV2 reached from the stop state and the acceleration b1. Further, the duration time of step G (from the time t1 to the time t2 in FIG. 20) is determined by the rotation velocity RV2 when the deceleration starts and the acceleration b2.

In the liquid delivery apparatus 1 of the second embodiment, rapid liquid delivery from the supply chamber 6A to the target chamber 7A can be realized by rapidly rotating the rotary substrate 2 in step G. Therefore, this apparatus is suitable for delivering liquids when the reaction time after mixing, such as a chemical reaction, is short.

Figure 23:
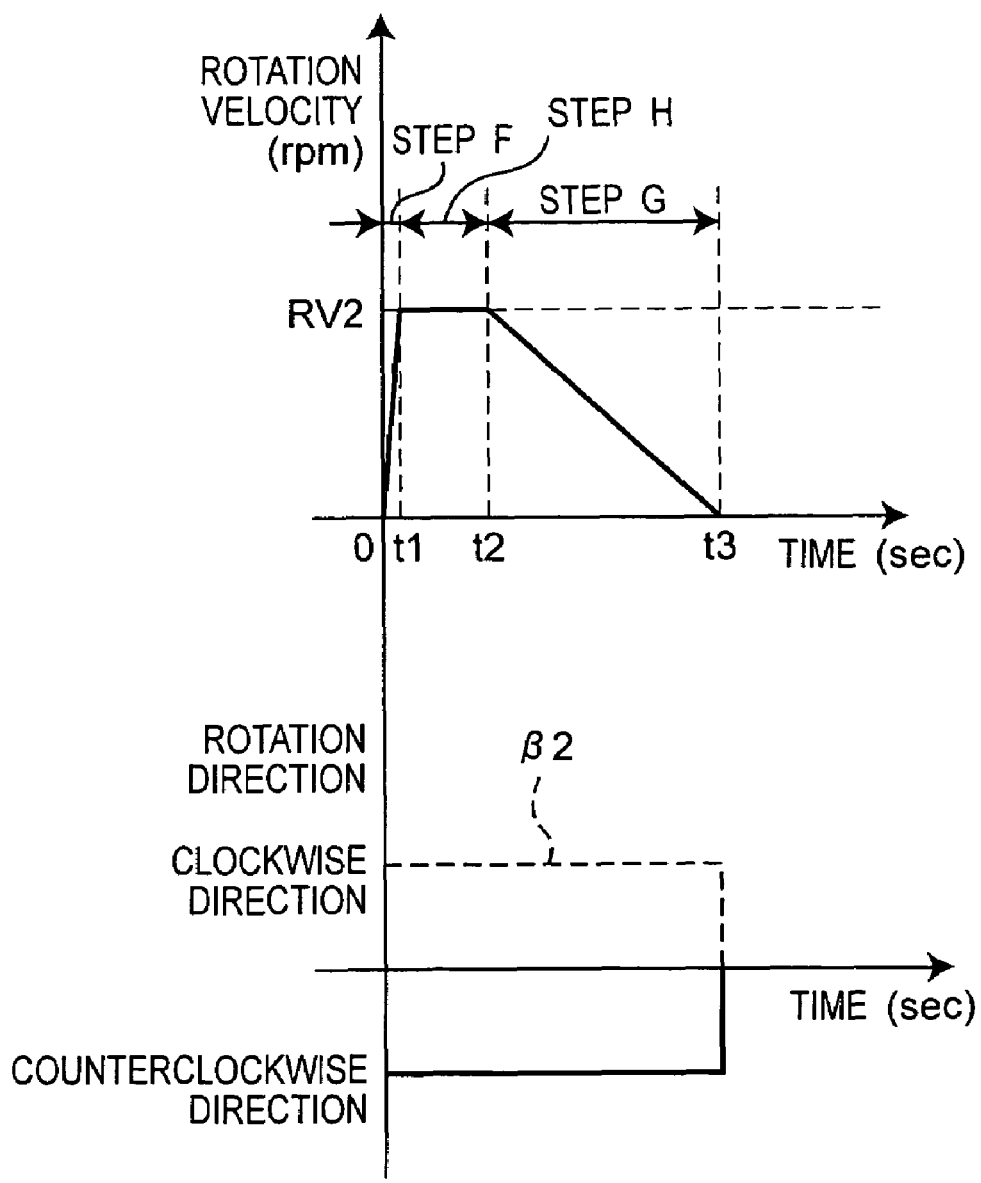
FIG. 23 is a diagram illustrating a velocity waveform and rotation direction of the second example of the operation of the liquid delivery apparatus according to the second embodiment of the present invention.

FIGS. 22 and 23 show a first alternative of the sequence of rotation drive in the second embodiment. In this alternative, a step H where the rotary substrate is rotated for a given length of time at a constant rotation velocity RV2 is executed (from the time t1 to the time t2 in FIG. 23) between step F where the rotary substrate 2 is rapidly rotated in the counterclockwise direction R2 (from the time instant t0 to the time instant t1 in FIG. 23) and step G where the rotary substrate 2 is braked (from the time t2 to the time t3 in FIG. 23). The step H where the rotary substrate 2 is rotated at the constant velocity RV2 makes it possible to execute a more complex liquid delivery control.

Figure 24:
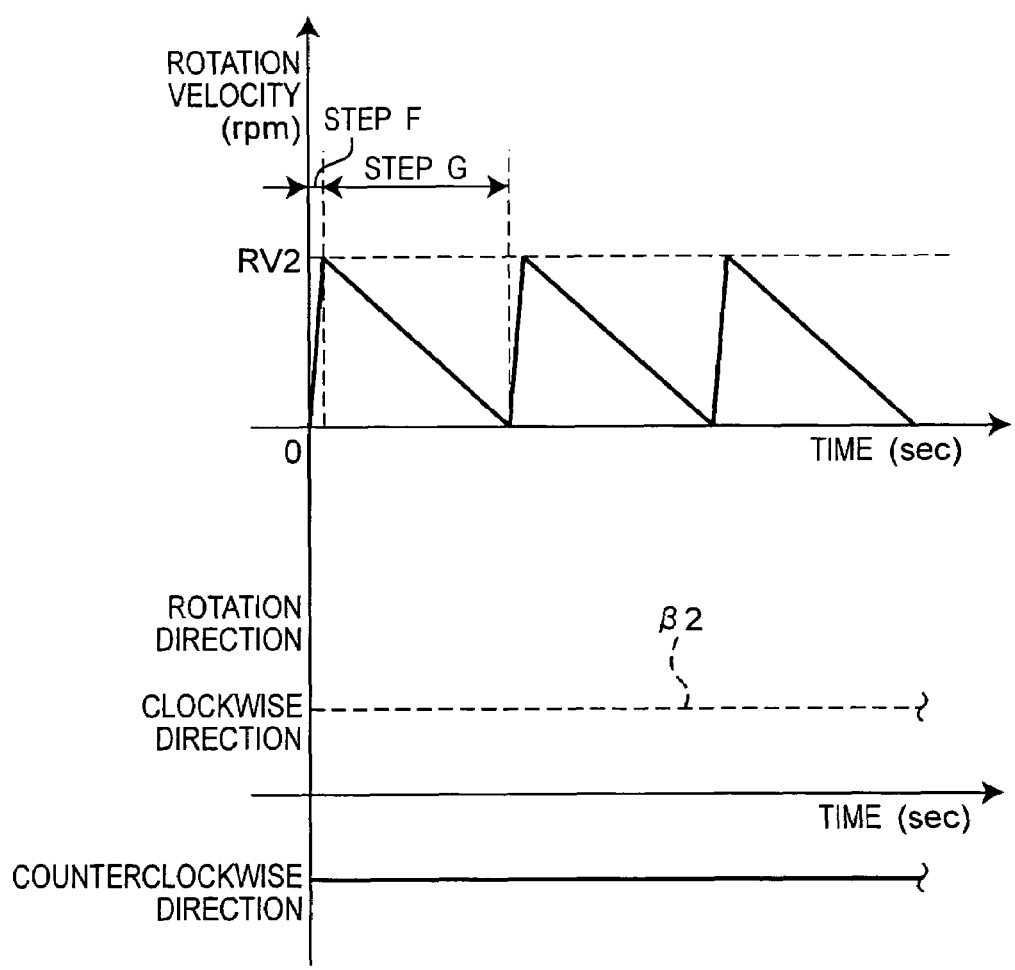
FIG. 24 is a diagram illustrating a velocity waveform and rotation direction of a third example of the operation of the liquid delivery apparatus according to the second embodiment of the present invention.

FIG. 24 shows a velocity waveform and rotation direction of a second alternative of the rotation drive sequence. In the second alternative, as shown schematically by the broken line α3 in FIG. 19, step F where the rotary substrate 2 is rapidly rotated in the counterclockwise direction R2 and step G where the rotation of the rotary substrate 2 is braked are continuously repeated. Because the intermittent liquid delivery in a continuous mode is possible, this alternative is effective when relatively large volume of liquid 9 is to be delivered from the supply chamber 6A to the target chamber 7A.

Figure 26:
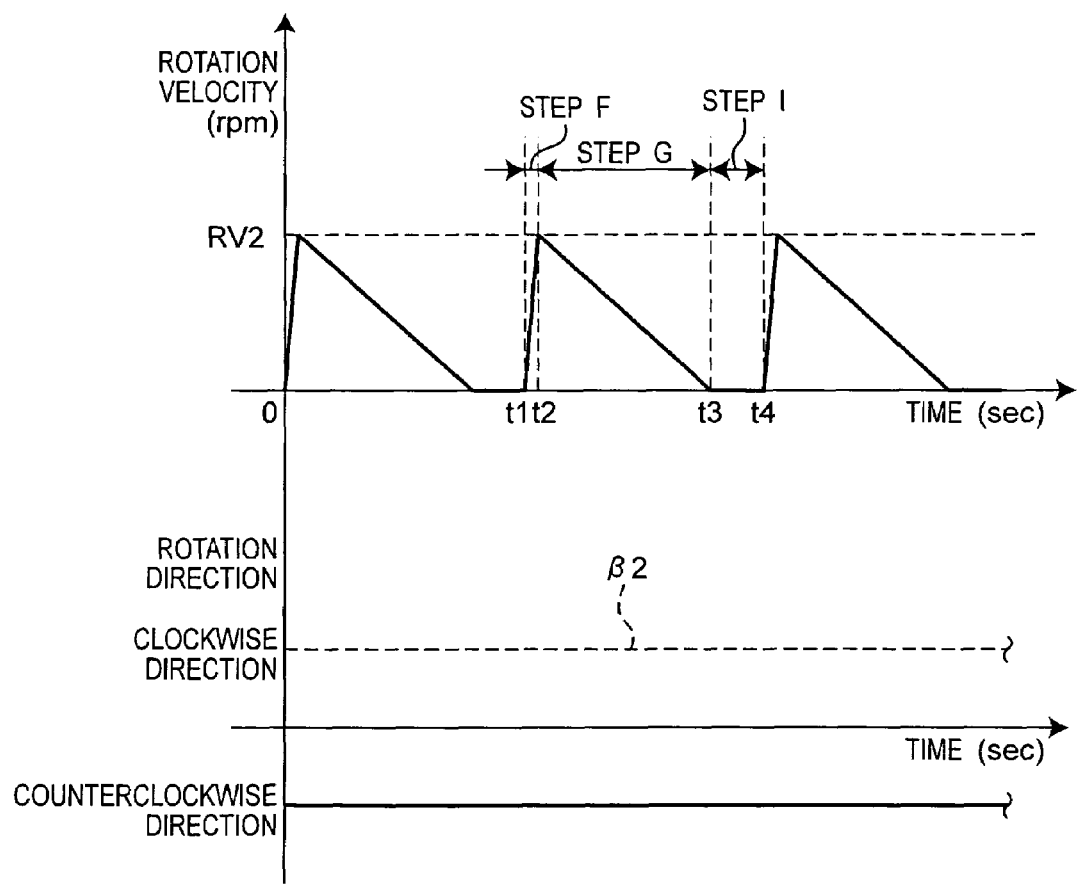
FIG. 26 is a diagram illustrating a velocity waveform and rotation direction of the fourth example of the operation of the liquid delivery apparatus according to the second embodiment of the present invention.

FIGS. 25 and 26 illustrate a third alternative of the rotation drive sequence. In the third alternative, step F where the rotary substrate 2 is rotated in the counterclockwise direction R2 (from the time t1 to the time t2 in FIG. 26) and step G for braking the rotary substrate 2 (from the time t2 to the time t3 in FIG. 26) are repeated with execution of an interval step I (from the time t3 to the time t4 in FIG. 26), where rotation of the rotary substrate 2 is halted for a given length time, each time steps F and G are completed. Providing the interval step I makes it possible to conduct intermittently continuous liquid delivery while conducting a reaction of liquid 9 in the target chamber 7A.

Figure 27:
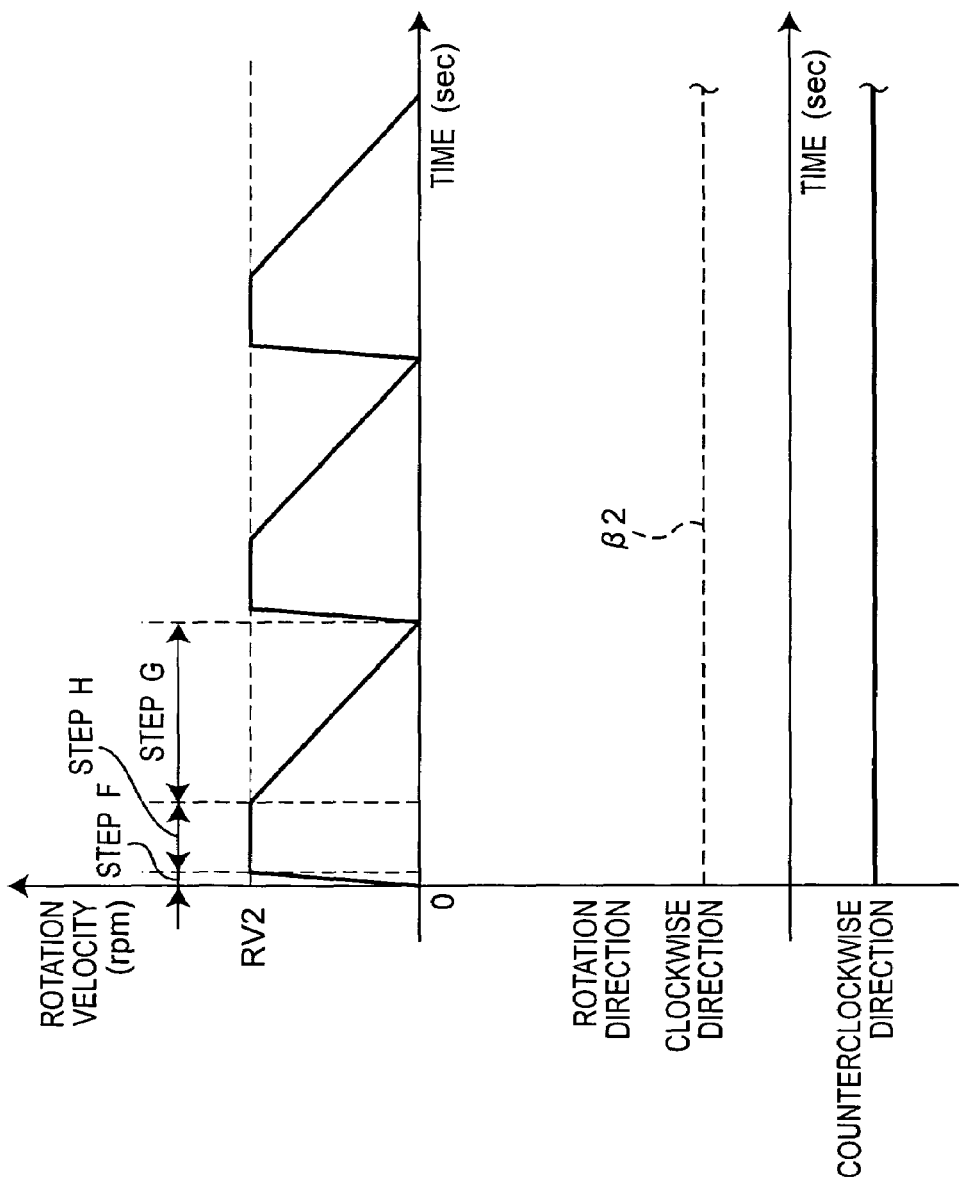
FIG. 27 is a diagram illustrating a velocity waveform and rotation direction of a fifth example of the operation of the liquid delivery apparatus according to the second embodiment of the present invention.

FIG. 27 shows a velocity waveform and rotation direction of a fourth alternative of the rotation drive sequence. In the fourth alternative, as shown schematically by the broken line α4 in FIG. 22, the step F, step H, and step G are continuously repeated in this order.

Figure 29:
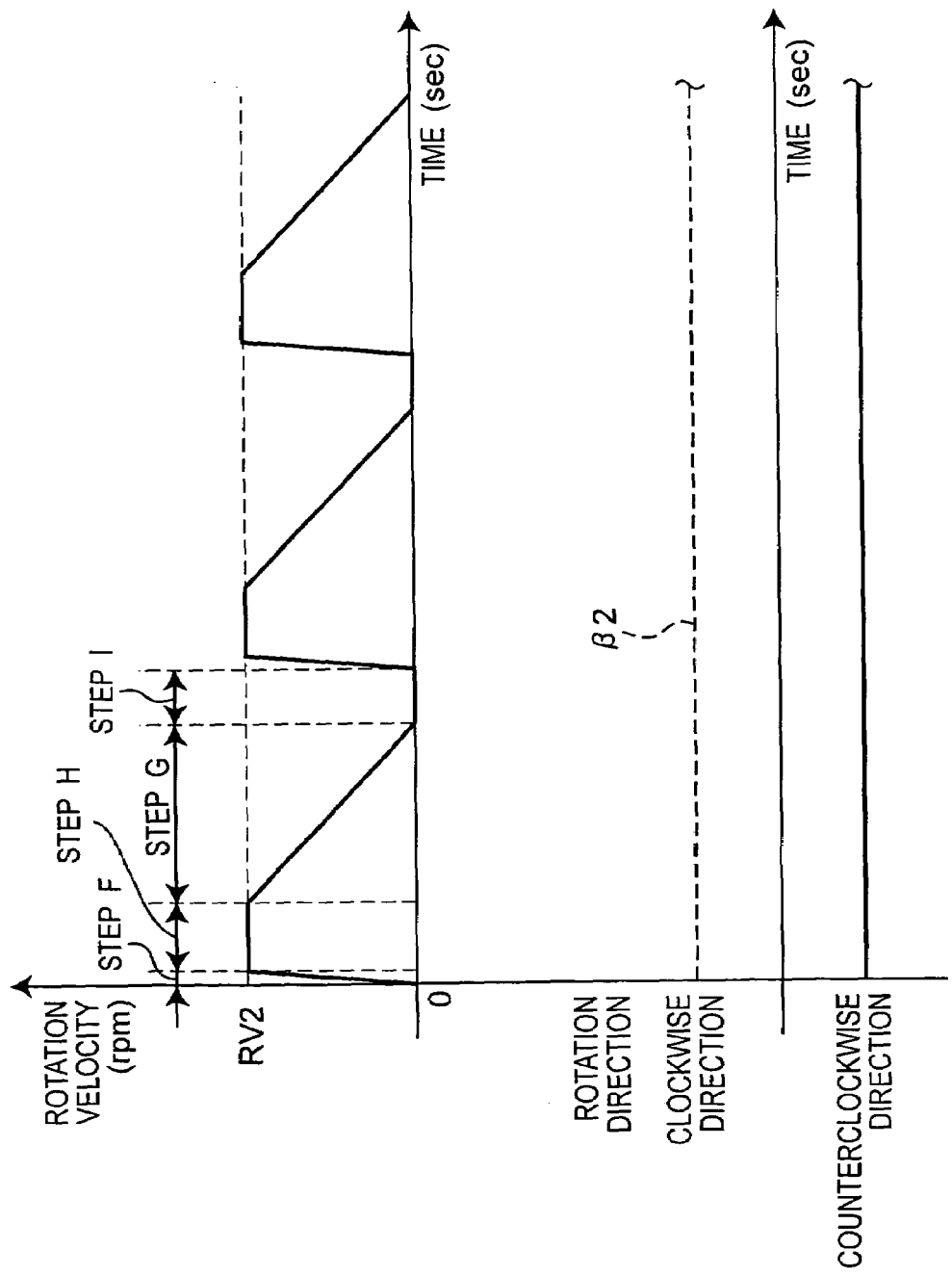
FIG. 29 is a diagram illustrating a velocity waveform and rotation direction of the sixth example of the operation of the liquid delivery apparatus according to the second embodiment of the present invention.

In a fifth alternative of the rotation drive sequence shown in FIGS. 28 and 29, the step F, step H, step G, and step I are continuously repeated in this order.

Figure 30:
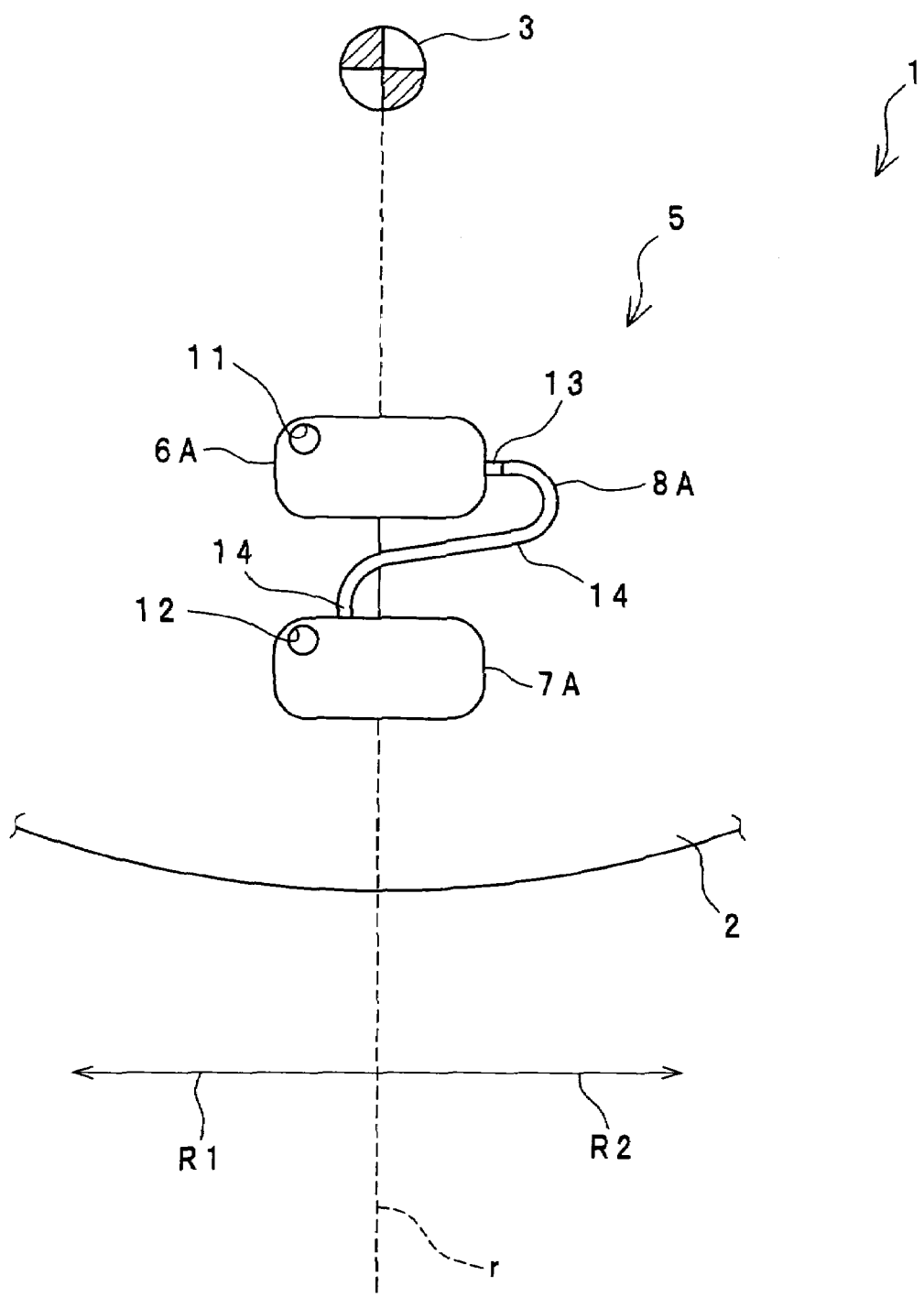
FIG. 30 is a partial enlarged plan view illustrating the rotary substrate of the liquid delivery apparatus according to a modification of the first and second embodiments.

FIG. 30 shows a liquid delivery apparatus 1 according to a modification of the first and second embodiments. Comparison of FIG. 2 and FIG. 30 clearly demonstrates that in the first and second embodiments the inlet end portion 13 of the channel 8A extends in the clockwise direction R1 from the supply chamber 6A. Contrarily, in the present modification, the inlet end portion 13 of the channel 8A extends in the counterclockwise direction R2 from the supply chamber 6A. For releasing the liquid 9 held in the inlet end portion 13 of the liquid delivery apparatus 1 according to the present modification by the inertial force Fi generated by the abrupt braking as same manner as in the first embodiment (step C), the rotation direction of the rotary substrate 2 in step B and step C (step D if executed) need to be set to the counterclockwise direction R2 as shown by broken lines β1 in FIGS. 6, 9, 10, 12, 13, and 15. On the other hand, for releasing the liquid 9 held in the inlet end portion 13 of the liquid delivery apparatus 1 according to the present modification by the inertial force Fi generated by the rapid rotation as same manner as in the second embodiment (step F), the rotation direction of the rotary substrate 2 in step F and step G (step H if executed) need to be set to the clockwise direction R1 as shown by broken lines β2 in FIGS. 20, 23, 24, 26, 27, and 29.

In general, the following relationship exists between the direction of the inlet end portion 13 and the rotation direction of the rotary substrate 2. In order to release the liquid held in the inlet end portion 13, it is necessary to generate the inertial force Fi in the direction where the inlet end portion 13 extends from the supply chamber 6A. Therefore, in case that the inertial force Fi is generated by rapid braking (step C), the rotary substrate 2 needs to be rotated in the same direction as the extension direction of the inlet end portion 13 from the supply chamber 6A when rapid braking starts. Further, in case that the inertial force Fi is generated by rapid rotation (step F), the rotary substrate 2 needs to be rotated in the direction opposite to the extension direction of the inlet end portion 13 form the supply chamber 6A.

Third Embodiment

Figure 31:
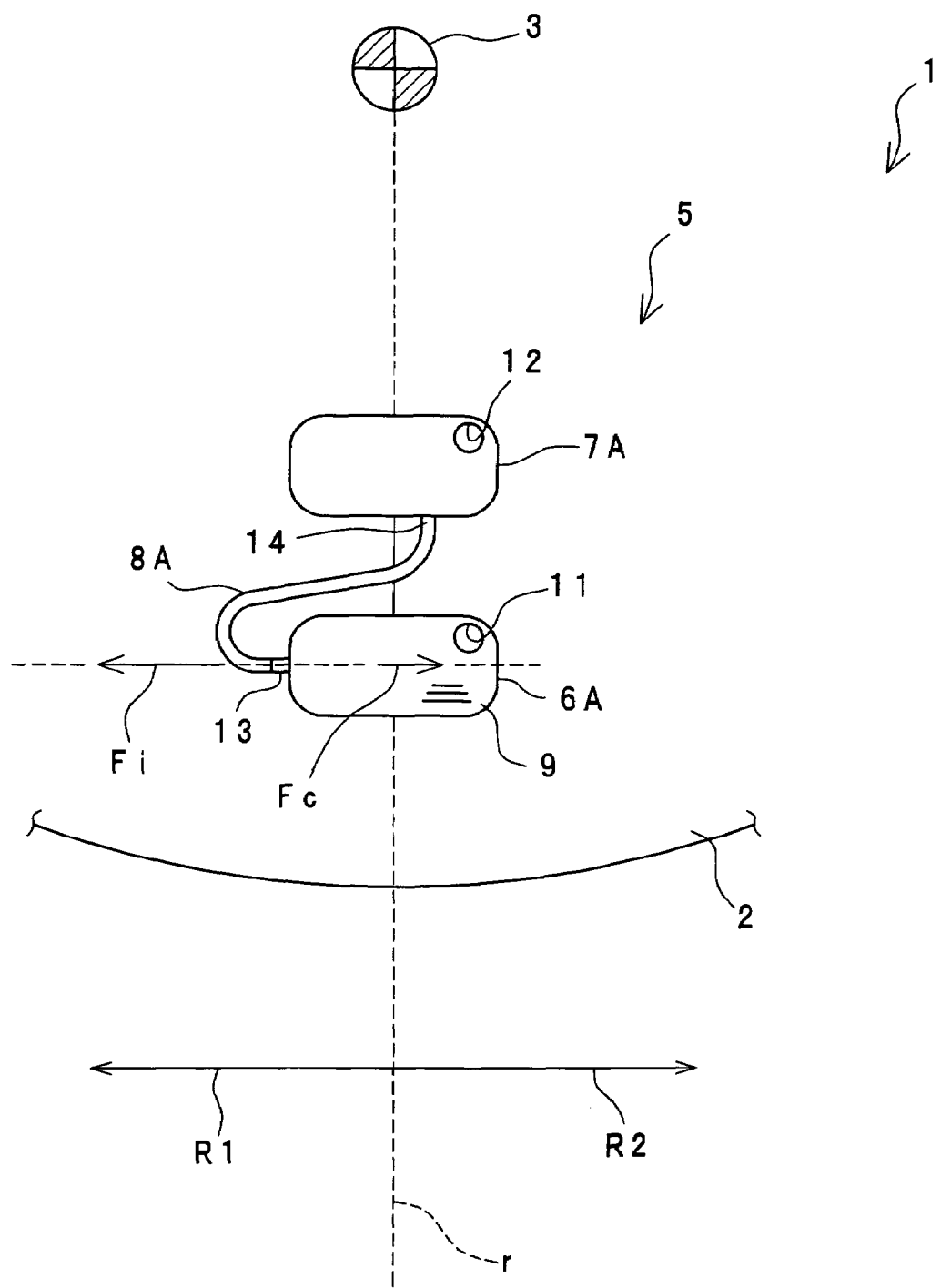
FIG. 31 is a partial enlarged plan view illustrating the rotary substrate of the liquid delivery apparatus according to a third embodiment of the present invention.

In a liquid delivery apparatus 1 of a third embodiment of the present invention shown in FIG. 31, the target chamber 7A is disposed on the inner side of the rotary substrate 2, i.e. in a position closer to the rotary shaft 3 than the supply chamber 6A. The inlet end portion 13 of the channel 8A extends in the clockwise direction R1 from the supply chamber 6A. The inertial force Fi in the clockwise direction R1 is generated when the rotary substrate 2 rotating in the clockwise direction R1 is rapidly braked (step C shown in FIGS. 6 and 8) as in the first embodiment, or when the rotary substrate 2 is rapidly rotated in the counterclockwise direction R2 (step F shown in FIGS. 20 and 22) as in the second embodiment. When the inertial force Fi exceeds the capillary force Fc, the holding of the liquid 9 in the inlet end portion 13 is released and the liquid 9 accommodated in the supply chamber 6A flows through the channel 8A into the target chamber 7A. Because the target chamber 7A is disposed in a position closer to the rotary shaft 3 than the supply chamber 6A as described above, the liquid 9 flows in the radial direction "r" of the rotary shaft 3, i.e. in the direction toward the rotary shaft 3 as the rotation center. With the liquid delivery using a centrifugal force as a driving force, the direction of liquid delivery is limited to the direction away from the rotation center. However, in accordance with the present invention, because the inertial force Fi serves as a drive force, liquid delivery in the centripetal direction, as in the present embodiment, can be achieved. This realizes a complex liquid delivery behavior with a simple fluid passage structure.

Other structures and operations of the third embodiment are identical to those of the first embodiment.

Figure 32:
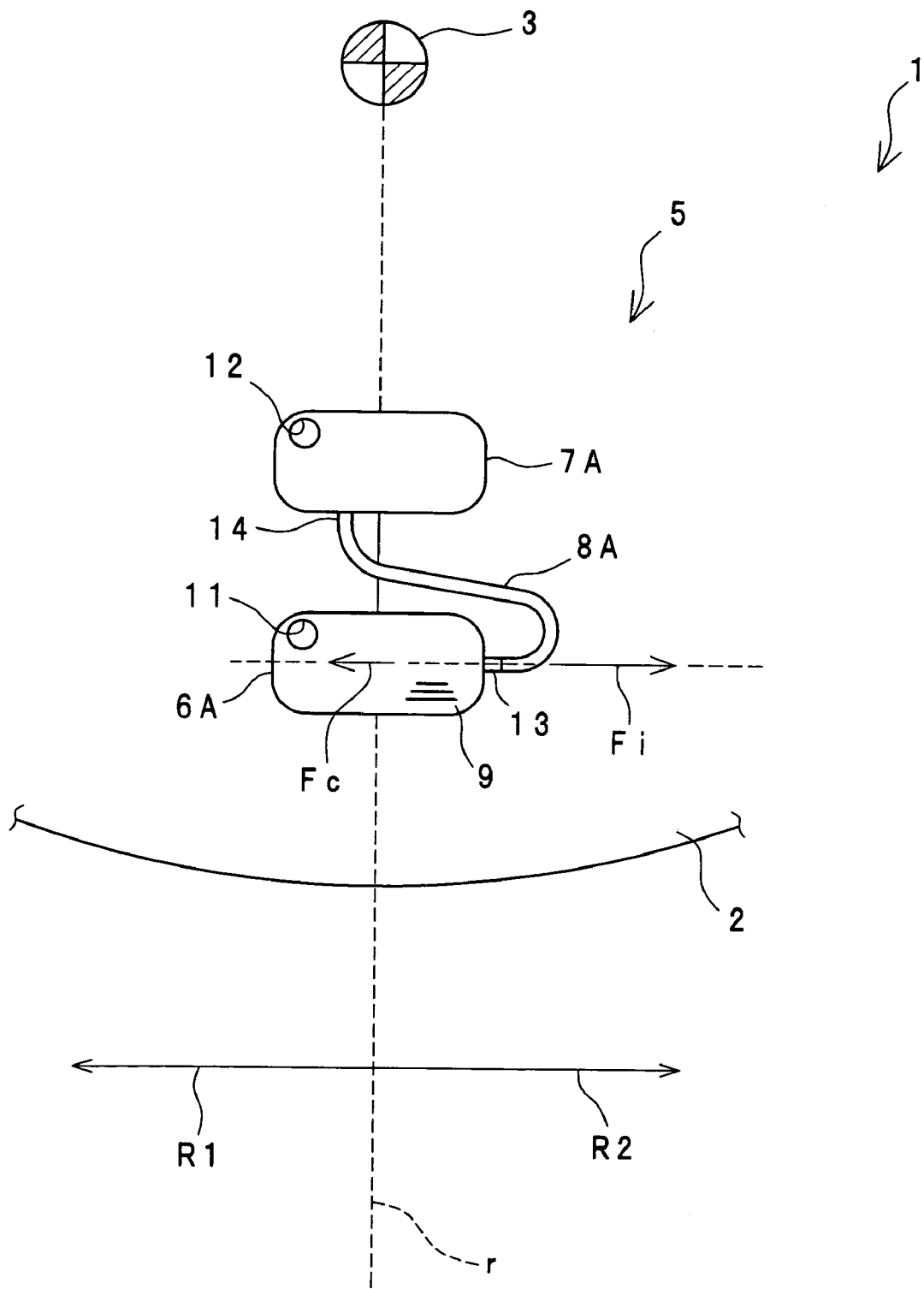
FIG. 32 is a partial enlarged plan view illustrating the rotary substrate of the liquid delivery apparatus according to a first modification of the third embodiment of the present invention.

FIG. 32 shows a first modification of the third embodiment. The inlet end portion 13 extends in the counterclockwise direction R2 from the supply chamber 6A. The inertial force Fi in the counterclockwise direction R2 is generated when the rotary substrate 2 rotating in the counterclockwise direction R2 is abruptly braked (step C in FIGS. 6 and 8) or when the rotary substrate 2 is rapidly rotated in the clockwise direction R1 (step F in FIGS. 20 and 22). If the holding of the liquid in the inlet end portion 13 is released by the inertial force Fi, the liquid 9 flows through the channel 8A toward the rotary shaft 3 and then flows into the target chamber 7A.

Figure 33:
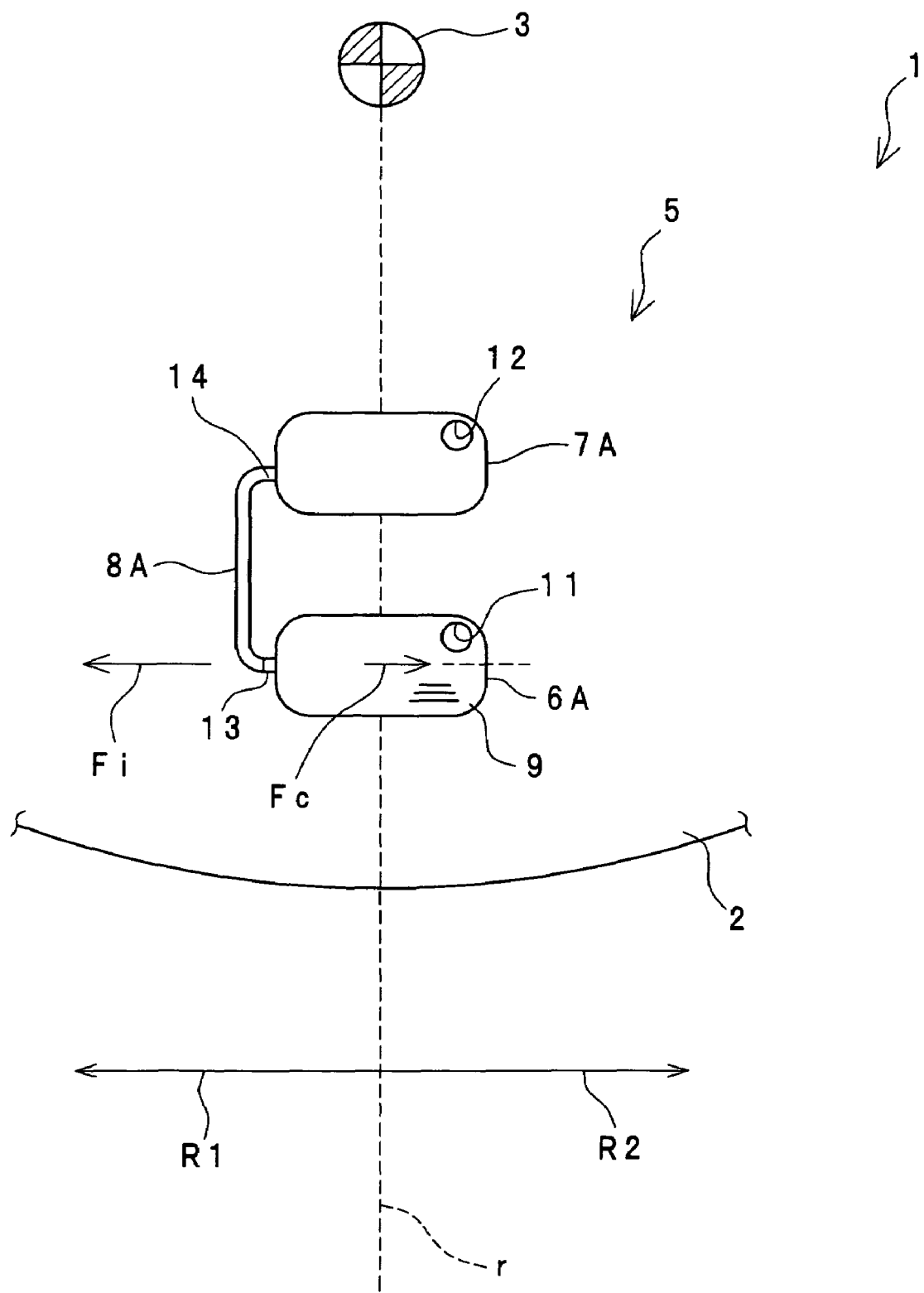
FIG. 33 is a partial enlarged plan view illustrating the rotary substrate of the liquid delivery apparatus according to a second modification of the third embodiment of the present invention.
Figure 34:
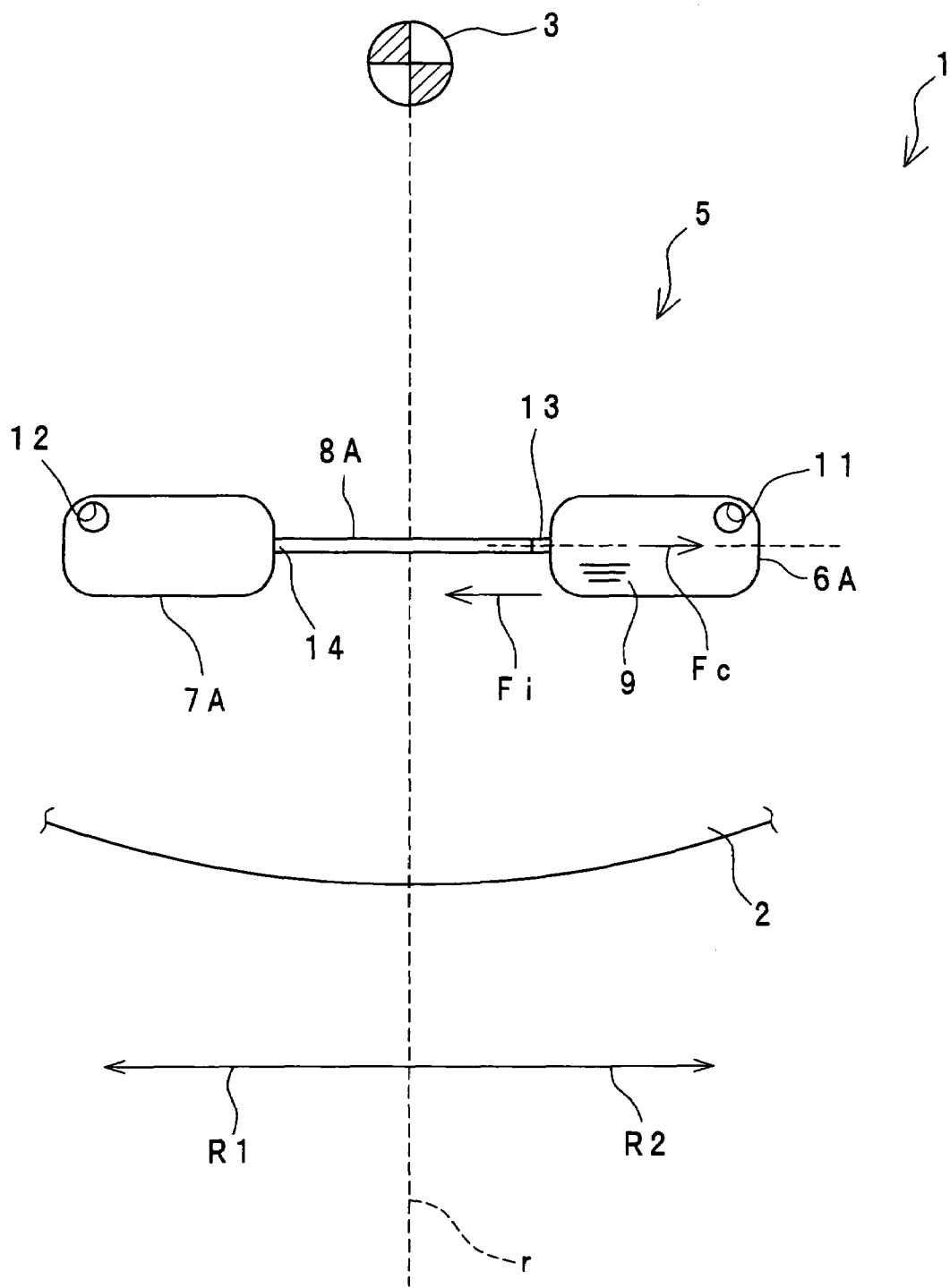
FIG. 34 is a partial enlarged plan view illustrating the rotary substrate of the liquid delivery apparatus according to a third modification of the third embodiment of the present invention.

In a second modification shown in FIG. 33, the channel 8A extends inwardly in the radial direction "r" without meandering. Further, in a third modification shown in FIG. 34, the supply chamber 6A and supply chamber 7A are arranged in a row perpendicular to the radial direction "r".

Fourth Embodiment

Figure 35:
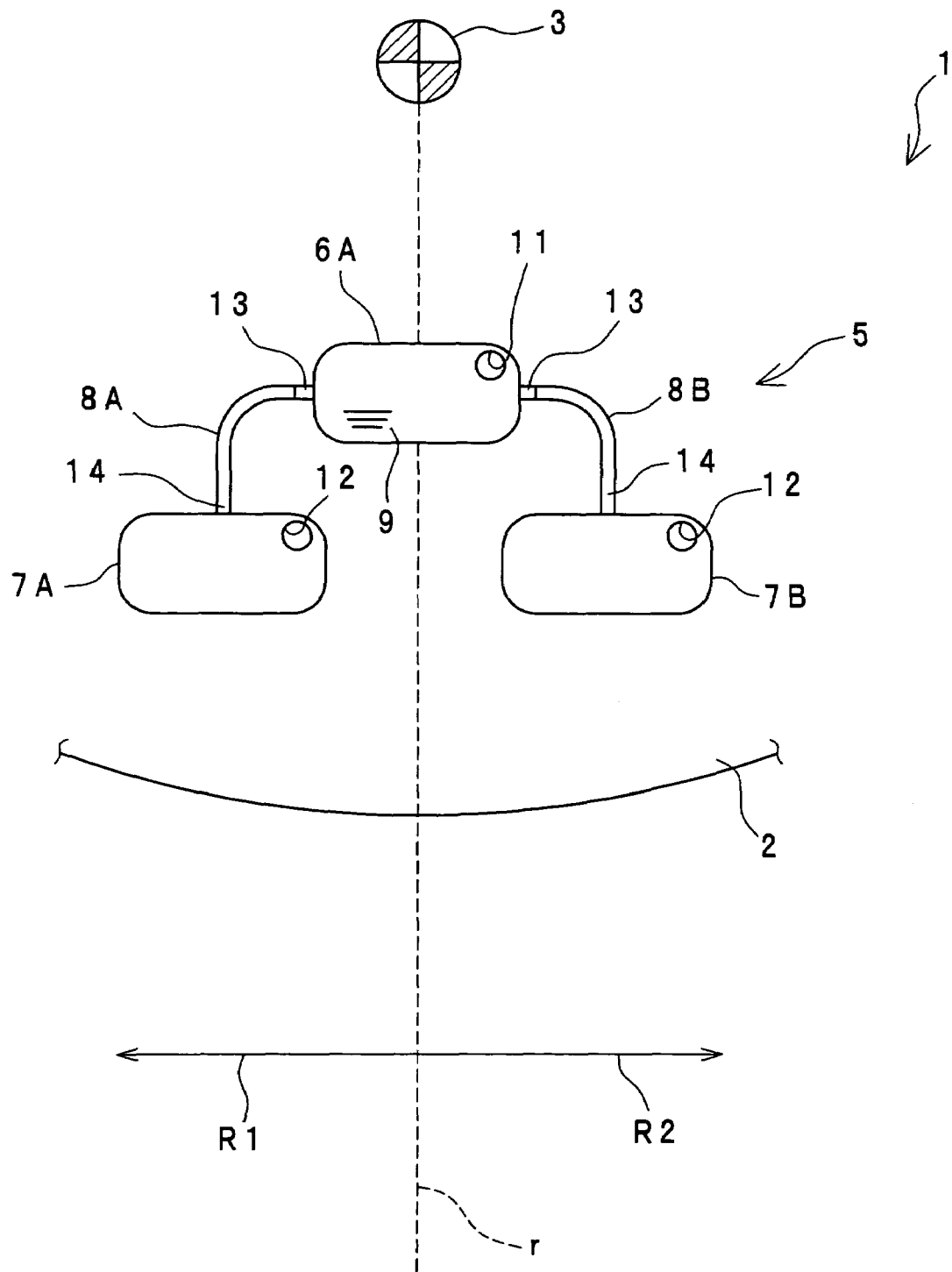
FIG. 35 is a partial enlarged plan view illustrating the rotary substrate of the liquid delivery apparatus according to a fourth embodiment of the present invention.

In a liquid delivery apparatus 1 of a fourth embodiment of the present invention shown in FIG. 35, the passage site 5 comprises an additional target chamber (third chamber) 7B in addition to the supply chamber 6A and target chamber 7A. Similarly to the target chamber 7A, the target chamber 7B is formed in the rotary substrate 2 so as to be spatially closed except for the air port 12. Further, the passage site 5 comprises a channel (second channel) 8B communicating the supply chamber 6A with the target chamber 7B, in addition to the channel 8A communicating the supply chamber 6A with the target chamber 7A. Similarly to the channel 8A, the channel 8B is formed in the rotary substrate 2 so as to be spatially closed.

Both of the target chambers 7A and 7B are arranged so as to be positioned outside in the radial direction "r" with respect to the supply chamber. The target chamber 7A is arranged on the clockwise direction "R1" side (left side in FIG. 35) to the supply chamber 6A. Therefore, the inlet end portion 13 of the fluid passage 8A extends in the clockwise direction R1 from the supply-chamber 6A. On the other hand, the target chamber 7B is arranged on the counterclockwise direction "R2" side (right side in FIG. 35) to the supply chamber 6A. Therefore, the inlet end portion (fourth fluid passage end portion) 13 of the fluid passage 8B extends in the counterclockwise direction R2 from the supply chamber 6A. The outlet end portion 14 of the fluid passage 8A extends outwardly in the radial direction "r" in order to prevent a counterblow. Similarly, the outlet end portion (fifth fluid passage end portion) 14 of the fluid passage 8B also extends outwardly in the radial direction "r". The inlet end portions 13 of the fluid passages 8A and 8B have hydrophobic property. Remaining portions of the fluid passages 8A and 8B other than the inlet end portions 13, as well as the supply chamber 6A, target chamber 7A, and target chamber 7B have hydrophilic property.

If the rotary substrate 2 rotating in the clockwise direction R1 is abruptly braked (step C in FIGS. 6 and 8) or if the rotary substrate 2 is rapidly rotated in the counterclockwise direction R2 (step F in FIGS. 20 and 22), after the liquid has been applied into the supply chamber 6A via the application port 11 (step A), the inertial force Fi in the clockwise direction R1 is generated. When the inertial force Fi exceeds the capillary force Fc, the liquid 9 held in the inlet end portion 13 of the channel 8A flows from the supply chamber 6A into the target chamber 7A through the fluid passage 8A. On the other hand, if the rotary substrate 2 rotating in the counterclockwise direction R2, rather than in the clockwise direction R1, is abruptly braked, or if the rotary substrate 2 is rapidly rotated in the clockwise direction R1, rather than in the counterclockwise direction R2, the inertial force Fi in the counterclockwise direction R2 is generated. When this inertial force Fi exceeds the capillary force Fc, the liquid 9 held in the inlet end portion 13 of the channel 8B flows from the supply chamber 6A to the target chamber 7B through the fluid passage 8B. Thus, the liquid 9 can be selectively delivered from the supply chamber 6A to the left side target chamber 7A or to the right side target chamber 7B, depending on the rotation direction of the rotary substrate 2 at the abrupt braking or rapid rotation.

Figure 36:
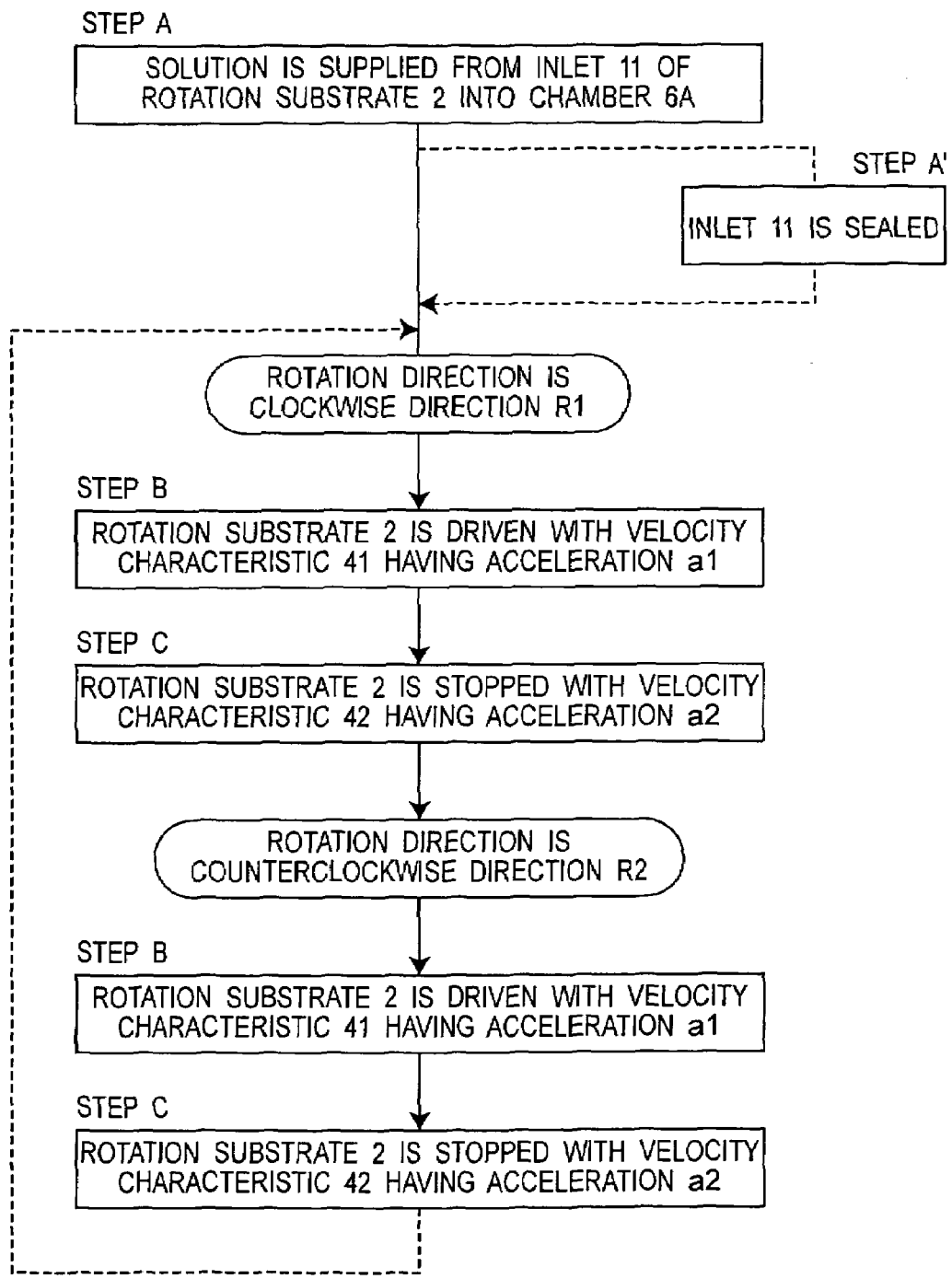
FIG. 36 is a flowchart for explaining the operation of the liquid delivery apparatus according to the fourth embodiment of the present invention.
Figure 37:
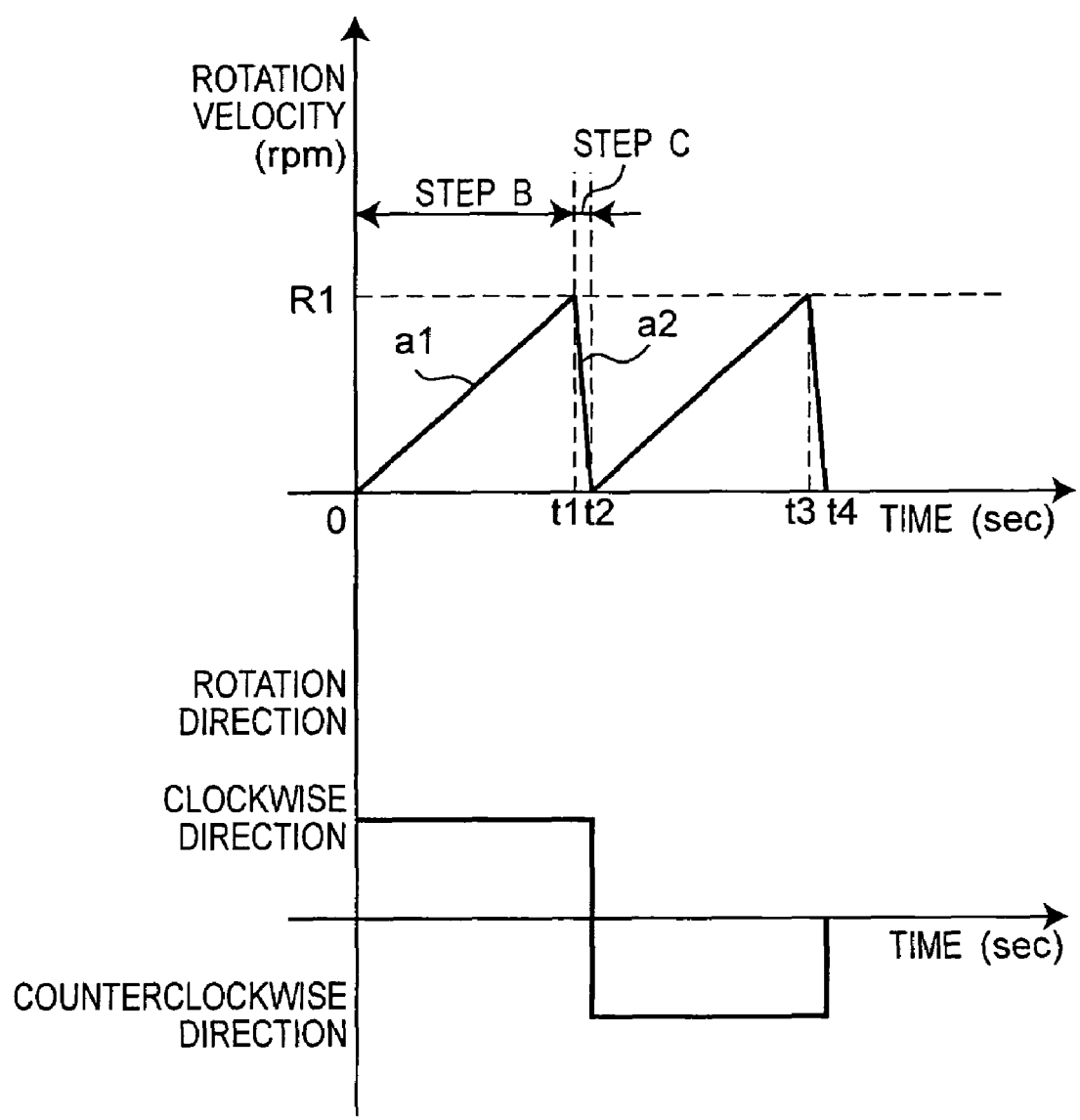
FIG. 37 is a diagram illustrating a velocity waveform and rotation direction of the operation of the liquid delivery apparatus according to the fourth embodiment of the present invention.

Further, by switching the rotation direction of the rotary substrate 2, it is possible to deliver the liquid 9 continuously and alternately from the supply chamber 6A to the target chambers 7A and 7B. FIGS. 36 and 37 show an example of such continuous switching of the liquid delivery direction. Referring to FIG. 36, after the liquid 9 has been applied into the supply chamber 6A (step A), the rotary substrate 2 is rotated in the clockwise direction R1 with a velocity characteristic 41 having a constant acceleration a1 (step B, from the time 0 to the time t1 in FIG. 37). Then, the rotary substrate 2 rotating according to the velocity characteristic 41 is rapidly braked with a velocity characteristic 42 having a constant acceleration a2 (step C, from the time t1 to the time t2 in FIG. 37). As a result, the inertial force Fi in the clockwise direction R1 acts on the liquid 9 in the inlet end portion 13 of the fluid passage 8A, and the liquid 9 in the supply chamber 6A flows into the target chamber 7A through the channel 8A. Then, with the rotation direction of the rotary substrate 2 reversed from the clockwise direction R1 to the counterclockwise direction R2, the step B (from the time t2 to the time t3 in FIG. 37) and step C (from the time t3 to the time t4 in FIG. 37) are executed. By abruptly stopping the rotation of the rotary substrate in the counterclockwise direction Re, the inertial force Fi in the counterclockwise direction R2 acting on the liquid 9 in the inlet end portion 13 of the fluid passage 8A is generated, and then the liquid 9 located in the supply chamber 6A flows into the target chamber 7B through the fluid passage 8B.

Other structures and operations of the fourth embodiment are identical to those of the first embodiment.

Figure 38:
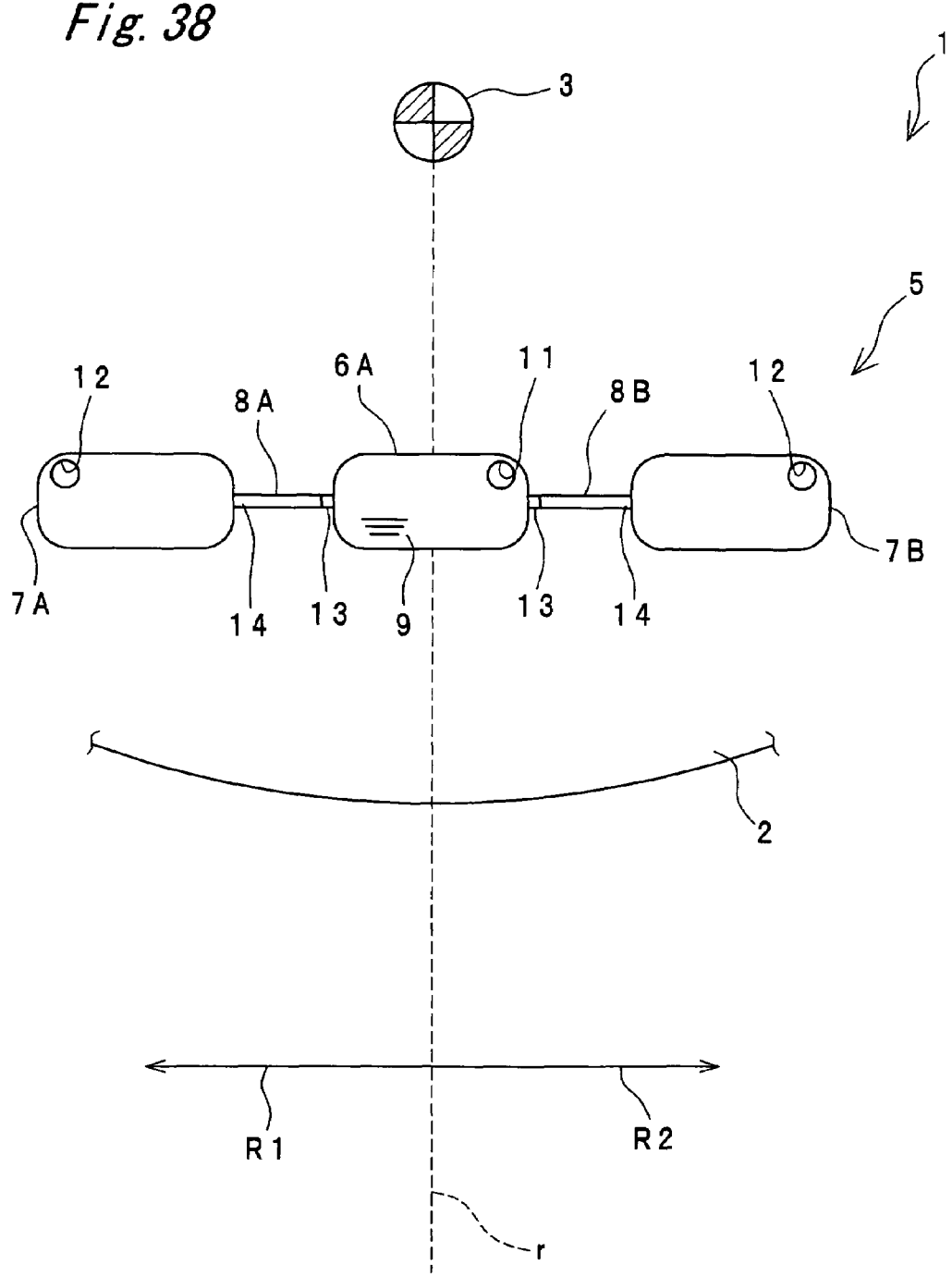
FIG. 38 is a partial enlarged plan view illustrating the rotary substrate of the liquid delivery apparatus according to a modification of the fourth embodiment of the present invention.

In a modification of the fourth embodiment shown in FIG. 38, the supply chamber 6A and the target chambers 7A and 7B disposed on the left and right side of the supply chamber 6A are arranged in a row direction perpendicular to the radial direction "r" of the rotary shaft 3.

Fifth Embodiment

Figure 39:
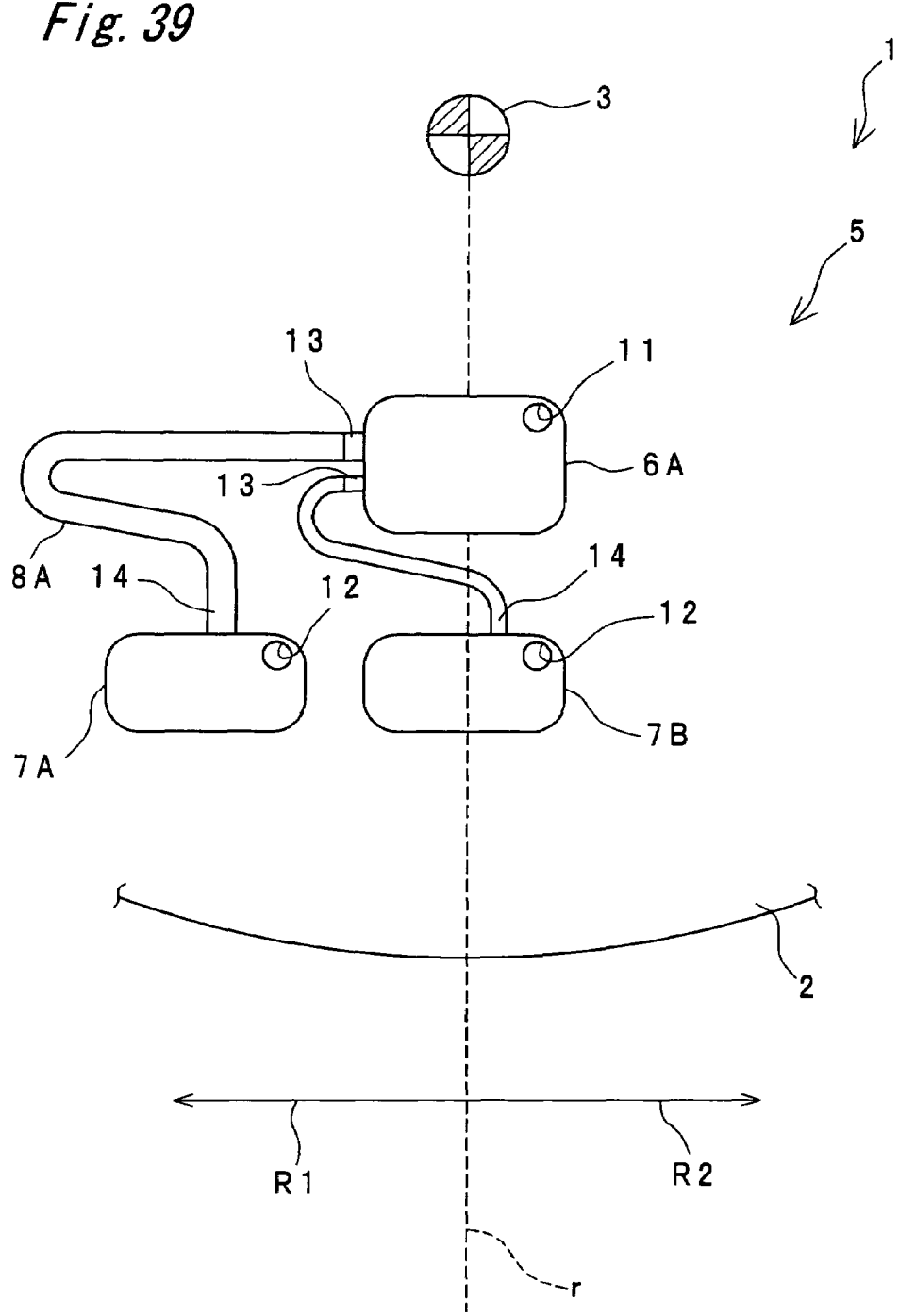
FIG. 39 is a partial enlarged plan view illustrating the rotary substrate of the liquid delivery apparatus according to a fifth embodiment of the present invention.
Figure 40:
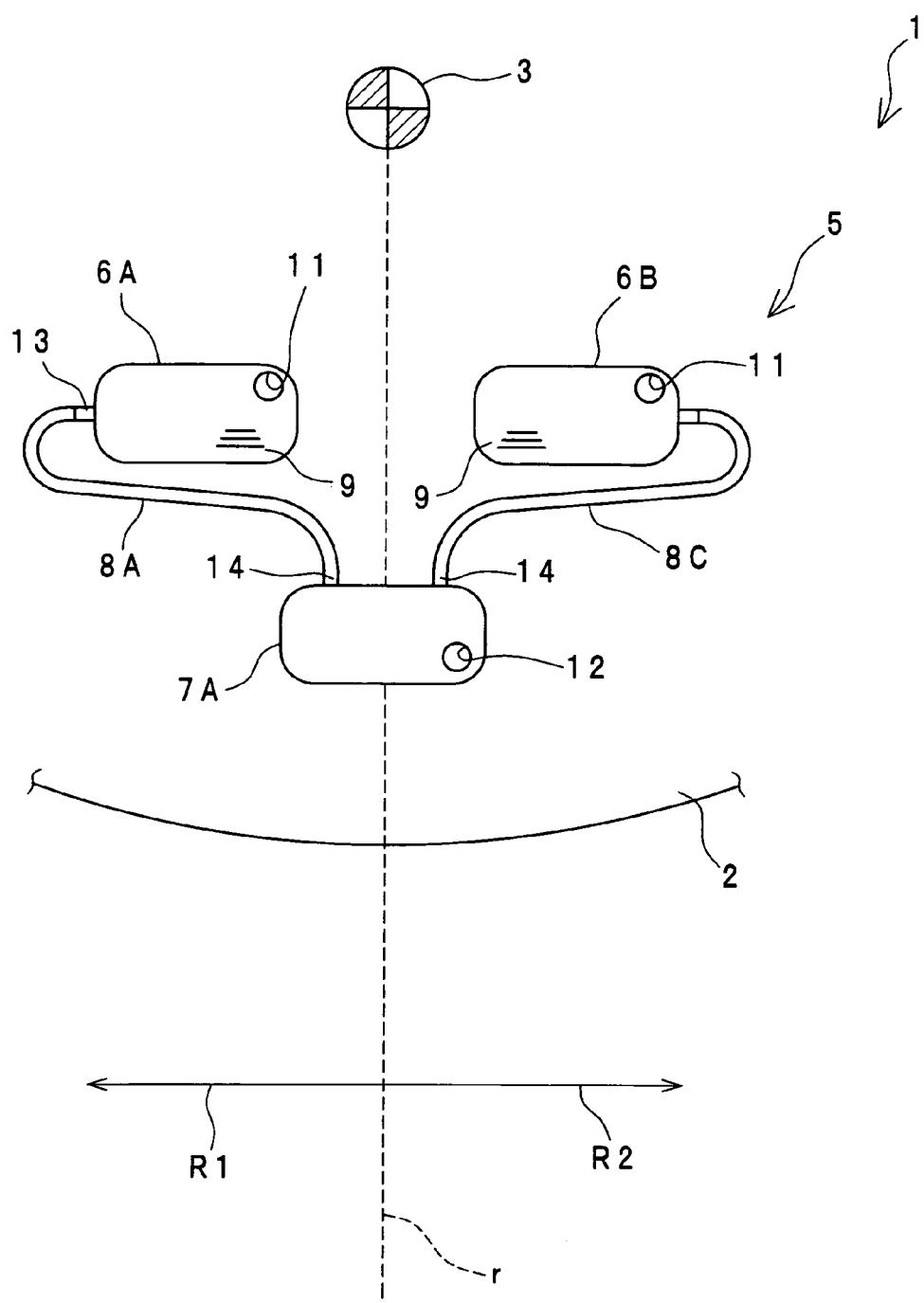
FIG. 40 is a partial enlarged plan view illustrating the rotary substrate of the liquid delivery apparatus according to a sixth embodiment of the present invention.

In the liquid delivery apparatus 1 according to a fifth embodiment of the present invention shown in FIG. 39, the passage site 5 comprises an additional target chamber (third chamber) 7B in addition to the supply chamber 6A and target chamber 7A. Similarly to the target chamber 7A, the target chamber 7B is formed in the rotary substrate 2 so as to be spatially closed except for the air port 12. Further, the passage site 5 comprises a fluid passage (second channel) 8B communicating the supply chamber 6A with the target chamber 7B, in addition to the fluid passage 8A communicating the supply chamber 6A with the target chamber 7A. Similarly to the fluid passage 8A, the fluid passage 8B is formed in the rotary substrate 2 so as to be spatially closed.

Both of the target chambers 7A and 7B are positioned outside in the radial direction "r" with respect to the supply chamber 6A. Both of the target chambers 7A and 7B are arranged on the clockwise direction "R1" side (left side in FIG. 39) to the supply chamber 6A. Therefore, the inlet end portion 13 of the fluid passage 8A extends in the clockwise direction R1 from the supply chamber 6A. Similarly, the inlet end portion (fourth fluid passage end portion) 13 of the fluid passage 8B also extends in the clockwise direction R1 from the supply chamber 6A. The inlet end portion 13 of the fluid passage 8A is closer to the rotation center than the inlet end portion 13 of the fluid passage 8B. Further, the cross-sectional area of the inlet end portion 13 of the fluid passage 8A is larger than the cross-sectional area of the inlet end portion 13 of the fluid passage 8B. Therefore, the pressure per unit area generated by a capillary force Fca applied to the inlet end portion 13 of the fluid passage 8A is necessarily less than the pressure per unit area generated by a capillary force Fcb applied to the inlet end portion 13 of the fluid passage 8B. The outlet end portion 14 of the channel 8A extends outwardly in the radial direction "r" in order to prevent the backward flow. Similarly, the outlet end portion (fifth fluid passage end portion) 14 of the fluid passage 8B also extends outwardly in the radial direction "r". The inlet end portions 13 of the fluid passages 8A and 8B have hydrophobic properties. Remaining portions of the fluid passages 8A and 8B other than the inlet end portions 13, as well as the supply chamber 6A, target chambers 7A and 7B have hydrophilic property.

If the rotary substrate 2 rotating in the clockwise direction R1 is abruptly braked (step C in FIGS. 6 and 8), or if the rotary substrate 2 is rapidly rotated in the counterclockwise direction R2 (step F in FIGS. 20 and 22), after the liquid has been applied into the supply chamber 6A via the application port 11 (step A), the inertial force Fi in the clockwise direction R1 is generated. Depending on the value of the inertial force Fi, three kinds of operation can be realized. Firstly, if the inertial force Fi is less than the capillary force Fca acting on the inlet end portion 13 of the fluid passage 8A, then the inertial force is also necessarily less than the capillary force Fcb acting on the inlet end portion 13 of the fluid passage 8B that is normally larger than the capillary force Fca. Therefore, the liquid 9 does not flow from the supply chamber 6A into the target chamber 7A. Secondly, if the inertial force Fi is larger than the capillary force Fca acting on the inlet end portion 13 of the channel 8A and less than the capillary force Fcb acting on the inlet end portion 13 of the channel 8B, the liquid 9 held in the inlet end portion 13 of the fluid passage 8A flows from the supply chamber 6A into the target chamber 7A through the fluid passage 8A, whereas no liquid flows from the supply chamber 6A to the target chamber 7A through the fluid passage 8B. Thirdly, if the inertial force Fi exceeds the capillary force Fcb acting on the inlet end portion 13 of the fluid passage 8B, then the inertial force Fi also necessarily exceeds the capillary force Fca acting on the inlet end portion 13 of the fluid passage 8A normally smaller than the capillary force Fcb. Therefore, the liquid 9 flows from the supply chamber 6A into the target chamber 7A through the fluid passage 8A and, at the same time, flows from the supply chamber 6A to the target chamber 7B through the fluid passage 8B. Further, when the level of the solution in the supply chamber 6A is between the inlet end portion 13 of the fluid passage 8A and the inlet end portion 13 of the fluid passage 8B, the liquid 9 does not flow from the supply chamber 6A into the target chamber 7A through the fluid passage 8A and only flows from the supply chamber 6A into the target chamber 7B through the fluid passage 8B. Thus, the liquid 9 can be selectively delivered into the target chamber 7A with the wide fluid passage 8A or the target chamber 7B with the narrow fluid passage extending in the same direction from the supply chamber 6A, depending on the value of acceleration at the abrupt braking or rapid rotation.

Sixth Embodiment

The liquid delivery apparatus 1 of the sixth embodiment of the present invention comprises two supply chambers, i.e. supply chambers 6A and 6B. The supply chambers 6A and 6B are arranged in the direction perpendicular to the radial direction "r". The target chamber 7A is arranged in a position father from the rotary shaft 3 than the supply chambers 6A, 6B. The inlet end portion 13 of the fluid passage 8A communicating the supply chamber 6A with the target chamber 7A extends in the clockwise direction R1. On the other hand, the supply chamber 6B is communicated with the target chamber 7A by the fluid passage 8C formed in the rotary substrate 2 so as to be spatially closed. The inlet end portion 13 of the fluid passage 8C extends in the counterclockwise direction R2. The inlet end portions 13 of the fluid passages 8A and 8C have hydrophobic property. Further, the outlet end portions 14 of the fluid passages 8A and 8C extend outwardly in the radial direction "r". Furthermore, remaining portions of the fluid passages 8A and 8C other than the inlet end portions 13, as well as the supply chambers 6A, 6B, and target chamber 7A have hydrophilic property.

If the rotary substrate 2 rotating in the clockwise direction R1 is abruptly braked (step C in FIGS. 6 and 8), or if the rotary substrate 2 is rapidly rotated in the counterclockwise direction R2 (step F in FIGS. 20 and 22), the inertial force Fi in the clockwise direction R1 is generated. When this inertial force Fi exceeds the capillary force Fc, the liquid 9 held in the inlet end portion 13 of the fluid passage 8A flows from the supply chamber 6A into the target chamber 7A through the fluid passage 8A. On the other hand, if the rotary substrate 2 rotating in the counterclockwise direction R2 is abruptly braked, or if the rotary substrate 2 is rapidly rotated in the clockwise direction R1, the inertial force Fi in the counterclockwise direction R2 is generated. If this inertial force Fi exceeds the capillary force Fc, the liquid 9 held in the inlet end portion 13 of the fluid passage 8C flows from the supply chamber 6A into the target chamber 7A through the fluid passage 8C. Therefore, according to the present invention, it possible to realize the liquid delivery control by which liquids that have been accommodated in two chambers are mixed in other chamber.

Other structures and operations of the sixth embodiment are identical to those of the first embodiment.

Seventh Embodiment

Figure 41:
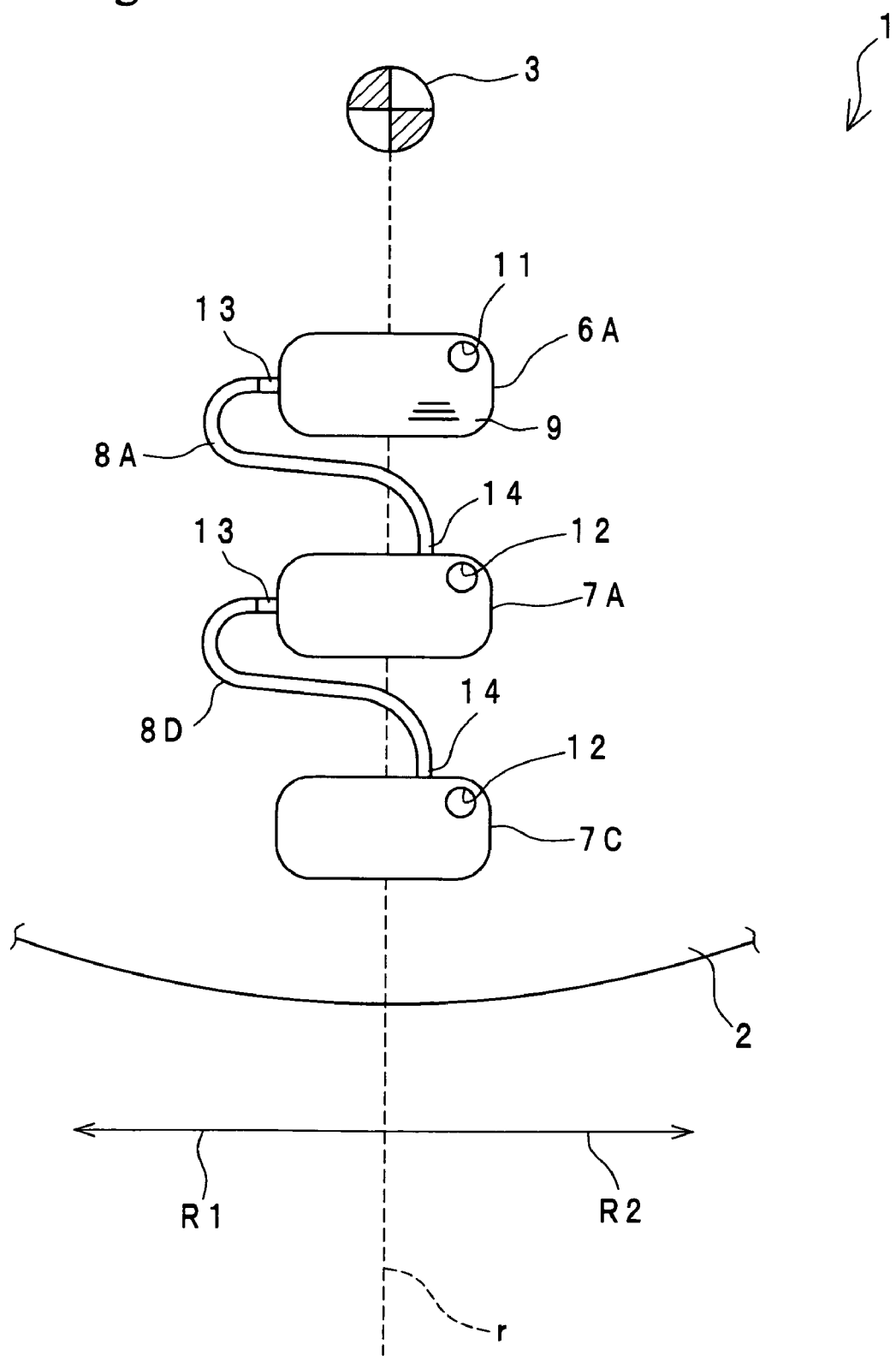
FIG. 41 is a partial enlarged plan view illustrating the rotary substrate of the liquid delivery apparatus according to a seventh embodiment of the present invention.

In the liquid delivery apparatus 1 of a seventh embodiment of the present invention shown in FIG. 41, a target chamber (fourth chamber) 7C is further connected to the target chamber 7A connected to the supply chamber 6A with the fluid passage 8A. The supply chamber 6A and target chambers 7A, 7C are arranged in a row in the radial direction "r". Specifically, the target chamber 7A is arranged on the outer side with respect to the supply chamber 6A, and the target chamber 7C is arranged further on the outer side with respect to the target chamber 7A. The inlet end portion 13 of the fluid passage 8A communicating the supply chamber 6A with the target chamber 7A extends in the clockwise direction R1. The outlet end portion 14 of the fluid passage 8A extends outwardly in the radial direction "r". The inlet end portion (fifth fluid passage end portion) 13 of the fluid passage (third channel) 8D connecting the target chamber 7A and the target chamber 7C also extends in the clockwise direction R1. Further, the outlet end portion (sixth fluid passage end portion) 14 of the fluid passage 8D extends outwardly in the radial direction "r". The inlet end portions 13 of the channels 8A, 8D have hydrophobic property. Furthermore, remaining portions of the fluid passages 8A, 8D other than the inlet end portions 13, as well as the supply chamber 6 and target chambers 7A, 7C have hydrophilic property.

If the rotary substrate 2 rotating in the clockwise direction R1 is abruptly braked, or if the rotary substrate 2 is rapidly rotated in the counterclockwise direction R2, the inertial force Fi in the clockwise direction R1 is generated. When the inertial force Fi exceeds the capillary force Fc, the liquid 9 held in the inlet end portion 13 of the fluid passage 8A flows from the supply chamber 6A into the target chamber 7A through the fluid passage 8A. If the rotary substrate 2 rotating in the clockwise direction R1 is abruptly braked or if the rotary substrate 2 is rapidly rotated in the counterclockwise direction R2 after the liquid 9 has been accommodated in the target chamber 7A, the inertial force Fi in the clockwise direction R1 is generated. Then, when this inertial force Fi exceeds the capillary force Fc, the liquid 9 held in the inlet end portion 13 of the fluid passage 8D flows from the target chamber 7A into the target chamber 7C through the fluid passage 8D. Therefore, multistage liquid delivery by which the liquid 9 located in the supply chamber 6A is successively delivered into the target chambers 7A, 7C can be realized by rotating the rotary substrate 2 according to the velocity characteristic comprising repeated acceleration and deceleration as shown in FIGS. 10, 12, 13, 15, 24, 26, 27, and 29. Such liquid delivery behavior can add functions to the respective liquid delivery. For example, more complex reaction functions including multiple stages, such as extraction, mixing, reaction, and detection of the solution can be executed in each chamber of one passage site.

Figure 42:
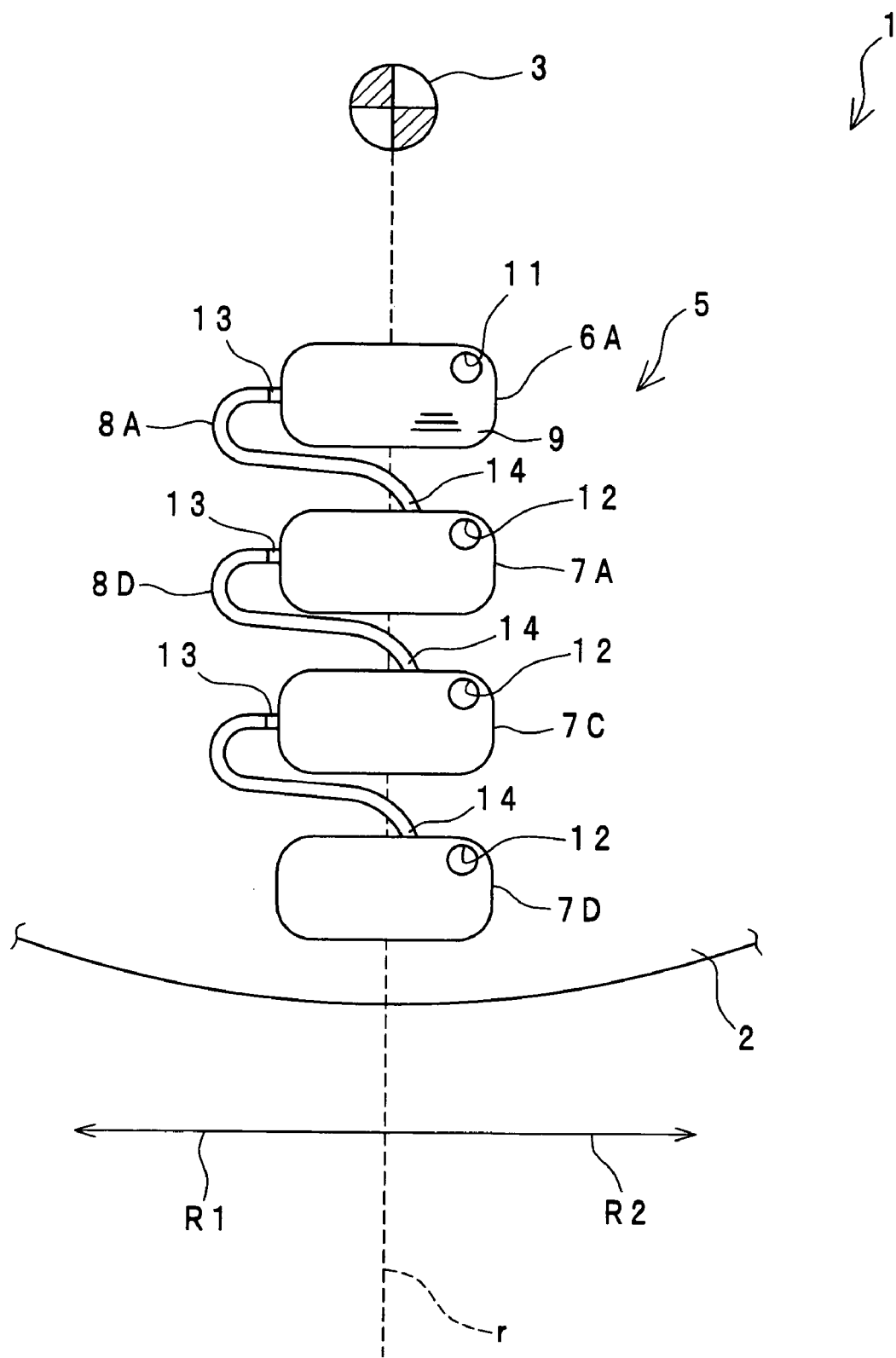
FIG. 42 is a partial enlarged plan view illustrating the rotary substrate of the liquid delivery apparatus according to a modification of the seventh embodiment of the present invention.

As shown in FIG. 42, a target chamber 7D may be additionally provided on the downstream side of the target chamber 7C. Such arrangement can achieve multistage liquid delivery including four or more stages.

Other structures and operations of the seventh embodiment are identical to those of the first embodiment.

Eighth Embodiment

Figure 43:
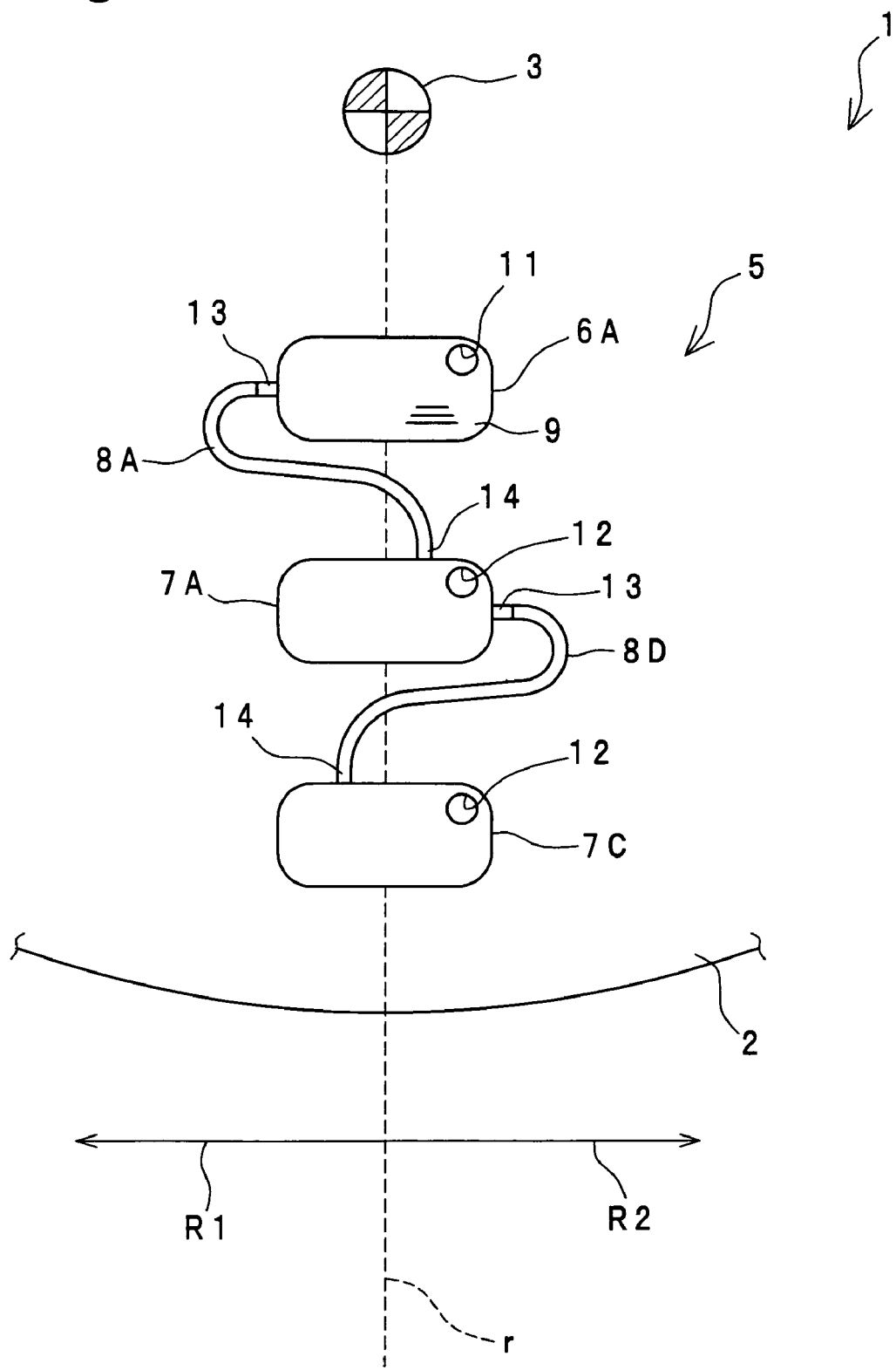
FIG. 43 is a partial enlarged plan view illustrating the rotary substrate of the liquid delivery apparatus according to an eighth embodiment of the present invention.

The liquid delivery apparatus 1 according to an eighth embodiment of the present invention shown in FIG. 43 has similar structure as that of the seventh embodiment (see FIG. 41), except that the inlet end portion 13 of the fluid passage 8A extends in the clockwise direction R1, whereas the inlet end portion 13 of the fluid passage 8D extends in the counterclockwise direction R2 from the target chamber 7A. In other words, in the eighth embodiment, the inlet end portions 13 of the fluid passages 8A and 8D extend in the mutually opposite directions.

If the rotary substrate 2 rotating in the clockwise direction R1 is abruptly braked, or if the rotary substrate 2 is rapidly rotated in the counterclockwise direction R2, the inertial force Fi in the clockwise direction R1 is generated. Then, when this inertial force Fi exceeds the capillary force Fc, the liquid 9 held in the inlet end portion 13 of the fluid passage 8A flows from the supply chamber 6A into the target chamber 7A through the fluid passage 8A. On the other hand, in order to deliver the liquid 9 in the target chamber 7A into the target chamber 7C, the rotary substrate 2 rotating in the counterclockwise direction R2, rather than clockwise direction R1, needs to be abruptly braked, or the rotary substrate 2 needs to be rapidly rotated in the clockwise direction R1, rather than counterclockwise direction R2. Therefore, in order to deliver the liquid 9 in the supply chamber 6A successively into the target chambers 7A, 7C, the abrupt braking of the rotary substrate 2 rotating in the clockwise direction R1 and then the abrupt braking of the rotary substrate 2 rotating in the counterclockwise direction R2 are executed as shown in FIG. 36 and FIG. 37, for example. The opposite extension directions of the inlet end portions 13 of the fluid passages 8A and 8C reliably prevents the liquid 9 from flowing backwardly from the target chamber 7A to the supply chamber 6A during the liquid delivery from the target chamber 7A to the target chamber 7C.

Other structures and operation of the eighth embodiment are identical to those of the first embodiment.

Ninth Embodiment

Figure 44:
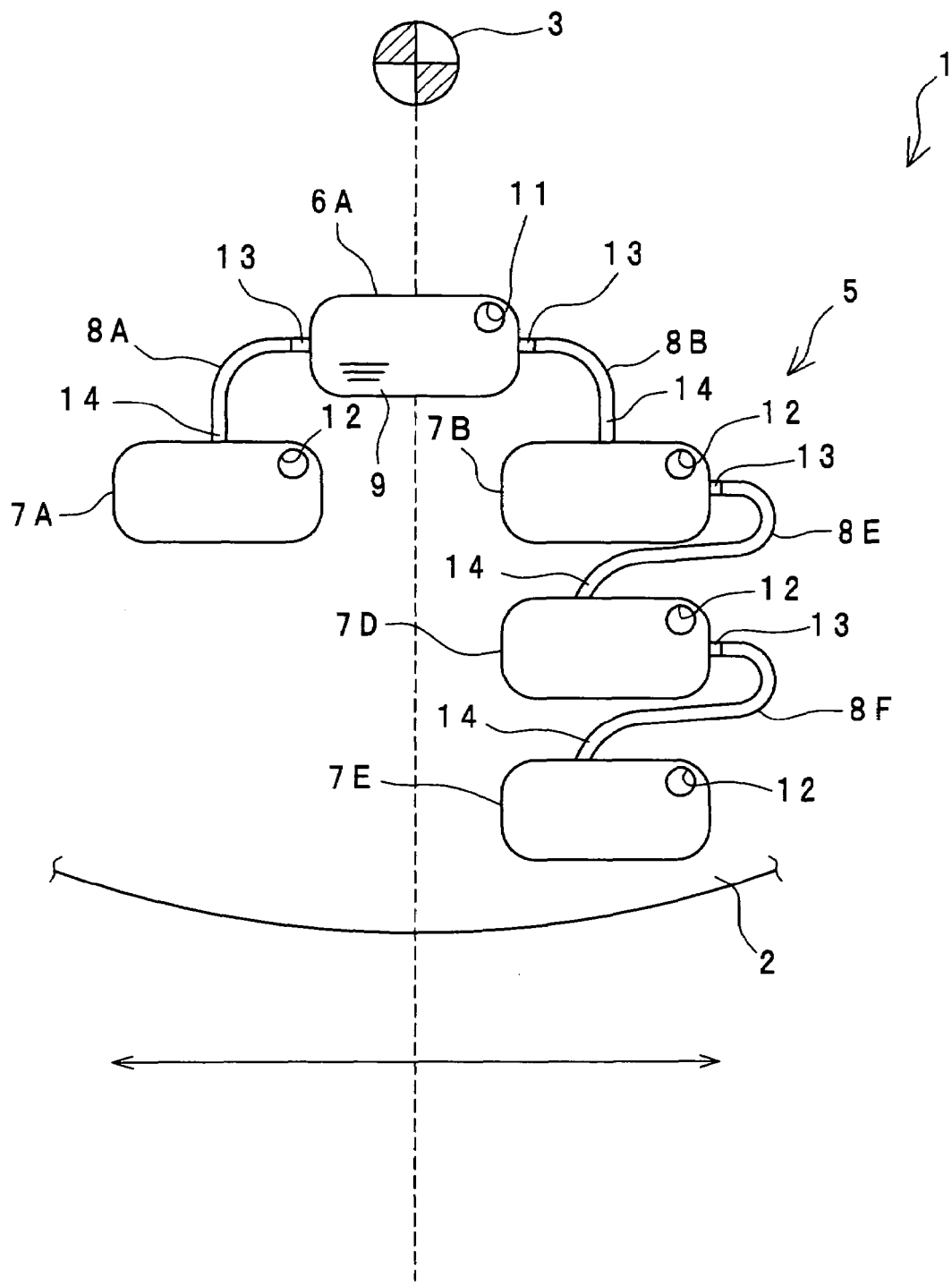
FIG. 44 is a partial enlarged plan view illustrating the rotary substrate of the liquid delivery apparatus according to a ninth embodiment of the present invention.

The liquid delivery apparatus 1 according to a ninth embodiment of the present invention shown in FIG. 44 has a structure further adding two target chambers 7D and 7E arranged downstream of the target chamber 7B to the fourth embodiment (see FIG. 35). The target chambers 7B and 7D are communicated with each other by a fluid passage 8E, and the target chambers 7D and 7E communicated with each other by a fluid passage 8F. The inlet end portions 13 of the fluid passages 8E and 8F extend in the counterclockwise direction R2.

If the rotary substrate rotating in the clockwise direction R1 is abruptly braked (step C shown in FIGS. 6 and 8), or if the rotary substrate is rapidly rotated in the counterclockwise direction R2 (step F shown in FIGS. 20 and 22), the inertial force Fi in the clockwise direction R1 is generated. Then, when this inertial force Fi exceeds the capillary force Fc, the liquid 9 held in the inlet end portion 13 of the fluid passage 8A flows from the supply chamber 6A into the target chamber 7A via the fluid passage 8A. On the other hand, if the rotary substrate 2 rotating in the counterclockwise direction R2, rather than the clockwise direction R1, is abruptly braked, or if the rotary substrate 2 is rapidly rotated in the clockwise direction R1, rather than counterclockwise direction R2, the inertial force Fi in the counterclockwise direction R2 is generated. The liquid 9 can be delivered from the supply chamber 6A into the target chamber 7E via the target chambers 7B, 7D in multistage manner. With the arrangement of chambers of the ninth embodiment, a liquid delivery control can be realized by which the liquid 9 accommodate in the source chamber 6A is supplied for various treatment operations in the target chambers 7B, 7D, and 7E, and the remaining liquid 9 is discarded into the target chamber 7A, for example.

Other structures and operations of the ninth embodiment are identical to those of the first embodiment.

Tenth Embodiment

Figure 45:
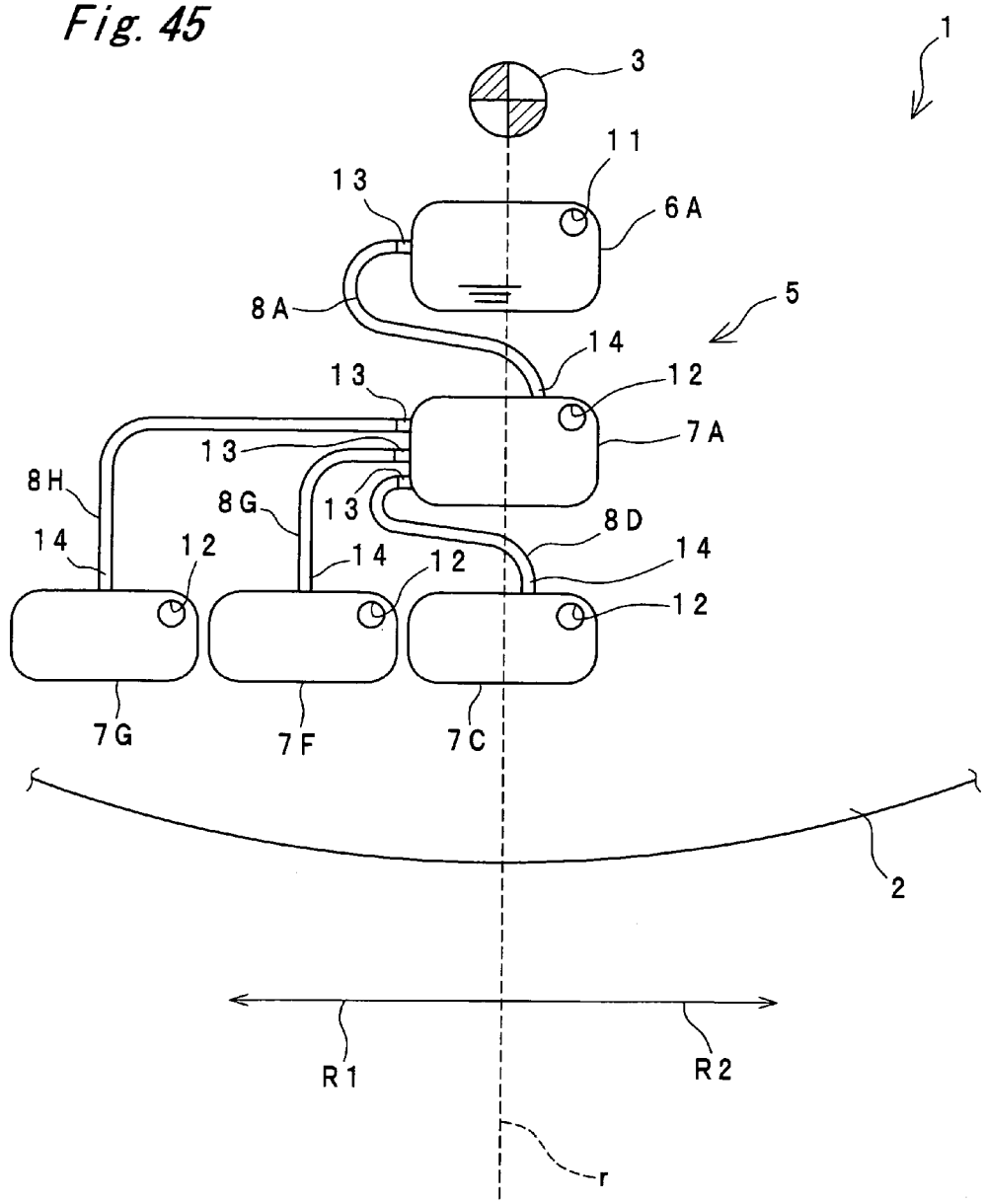
FIG. 45 is a partial enlarged plan view illustrating the rotary substrate of the liquid delivery apparatus according to a tenth embodiment of the present invention.

The liquid delivery apparatus 1 according to a tenth embodiment of the present invention shown in FIG. 45 has an arrangement in which two additional chambers, i.e. target chambers 7F and 7G, are communicated with the target chamber 7A of the sixth embodiment (FIG. 41) in addition to the target chamber 7C.

Both of the fluid passage 8G communicating the target chambers 7A and 7F with each other and the fluid passage 8H communicating the target chambers 7A and 7G with each other have inlet end portions 13 extending in the clockwise direction R1. Further, the outlet end portions 14 of the channels 8G and 8H extend outwardly in the radial direction "r". Three or more chambers as the target chambers 7C, 7F, and 7G of the present embodiment can be connected to one chamber.

Other structures and operations of the tenth embodiment are identical to those of the first embodiment.

Eleventh Embodiment

Figure 46:
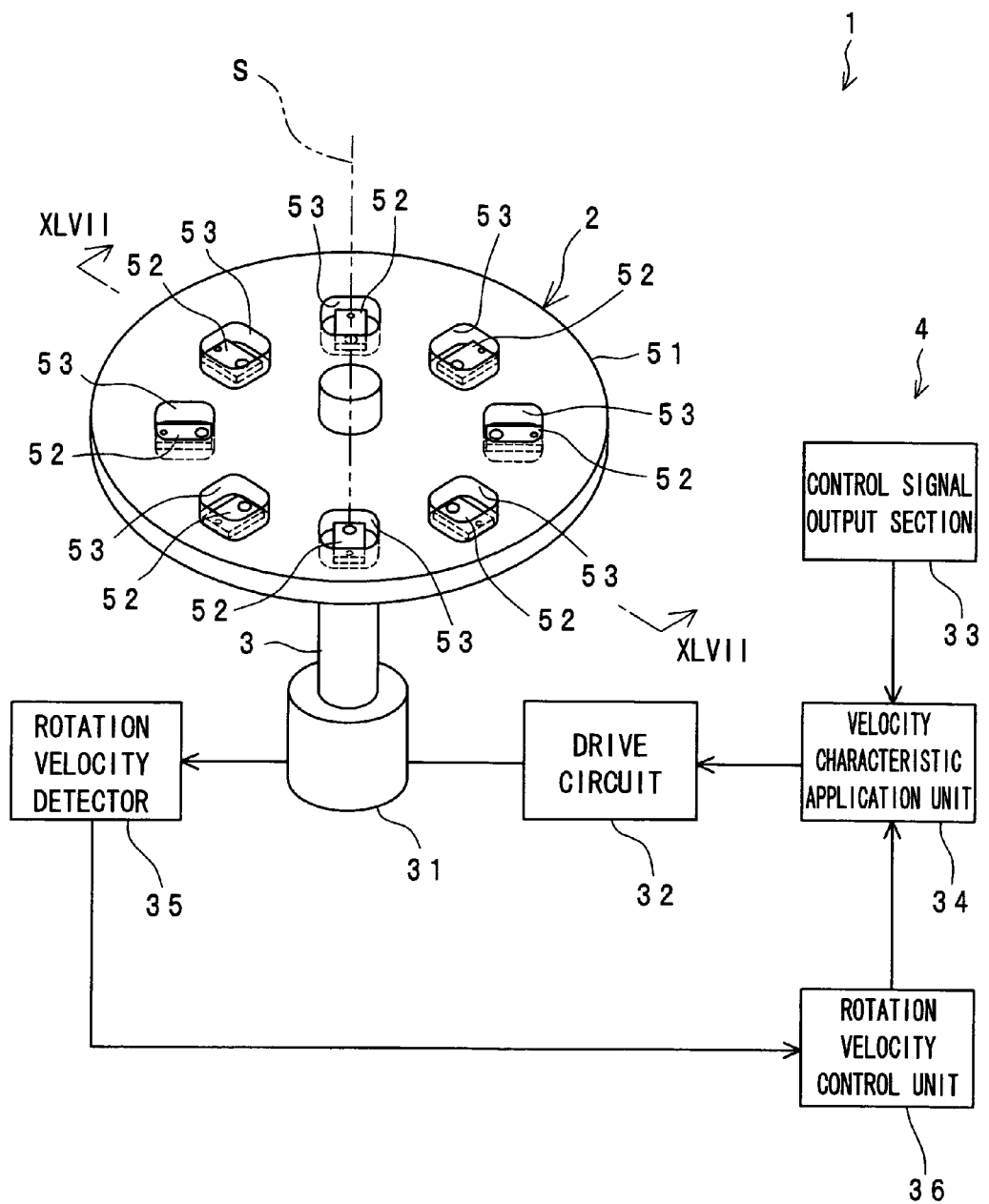
FIG. 46 is a schematic structural diagram illustrating the liquid delivery apparatus according to an eleventh embodiment of the present invention.
Figure 47:
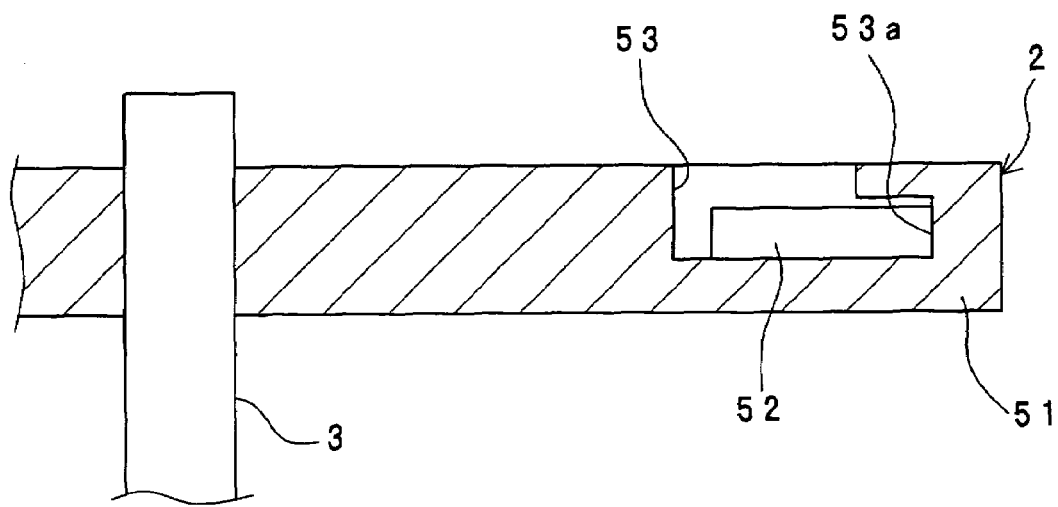
FIG. 47 is a partial enlarged cross-sectional view taken along a lien XLVII-XLVII in FIG. 46.
Figure 48:
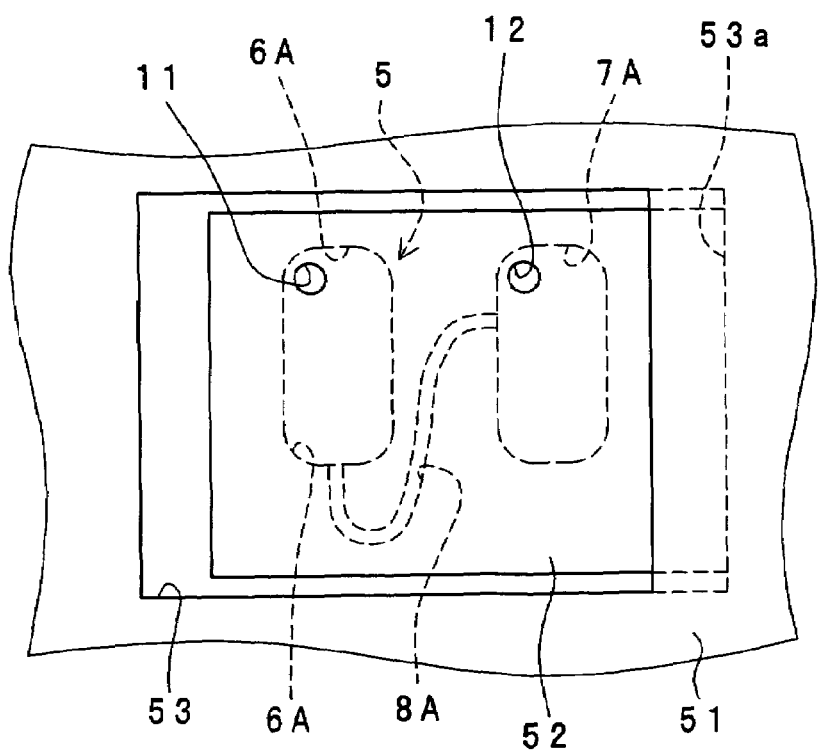
FIG. 48 is a partial enlarged plan view illustrating the rotary substrate according to the eleventh embodiment of the present invention.

In the liquid delivery apparatus 1 according to an eleventh embodiment of the present invention shown in FIGS. 46 to 48, the structure of the rotary substrate 2 is different from that of the first embodiment. Specifically, the rotary substrate 2 comprises a rotary substrate main body 51 and chip bodies 52 can be detachably attached to the rotary substrate main body 51. Each of passage sites 5 is formed in each of the chip bodies 51 rather than the rotary substrate main body 51. A plurality of accommodation holes 53 for accommodating the chip bodies 52 are formed in the upper surface side of the rotary substrate main body 51. The accommodation openings 53 are disposed radially with respect to the rotation shaft 3. Recesses 53a are formed in a wall surface on the outer side of the accommodation holes 53. The chip bodies 52 are held inside the accommodation holes 53 by a part of chip bodies 52 being arranged inside the recesses 53a. In particular, because the chip bodies 52 are urged toward the recesses 53a by the centrifugal force when the rotary substrate 2 is rotated, the chip bodies are reliably held in the rotary substrate main body 51 without falling out of the accommodation holes 53.

Other structures and operations of the eleventh embodiment are identical to those of the first embodiment.

The liquid delivery apparatus and liquid delivery method according to the present invention are useful as drive sources of devices for analyzing bio-ingredient such as proteins contained in biosamples, in particular, blood. In particular, blood samples are separated into blood cells and blood plasma at a preliminary stage, and proteins contained in blood plasma are measured. Further, centrifugal separation using a centrifugal force is preferably used for such separation. Therefore, liquid delivery systems using rotary substrates can be easily combined with blood cells—blood plasma separation using a centrifugal force. Further, by supporting a reagent in each chamber or by implementing physical operations such as heating in each chamber, it is possible to provide functions such as reactions, purification, and detection. Therefore, the present invention can be applied to applications such as POCT (Point Of Care Test: field diagnostics thereof) diagnostic biosensors for conducting separation, purification, reactions, and detection of proteins or health indicators contained in blood samples. A specific feature of the liquid delivery method according to the present invention over conventional methods is that liquid delivery can be conducted without using the centrifugal force. By this feature, channels and chambers can be easily unified for blood cells-blood plasma separation. Specifically, because blood cells-blood plasma separation uses the difference in density between blood cells and blood plasma induced by a centrifugal force, blood cells having a larger density always sediment in the centrifugal direction. With the conventional liquid delivery methods, a blood cell component that sediments in the centrifugal direction impeded the process when the separated blood plasma was delivered into another chamber. However, because the directions of the fluid passage end portions in the liquid delivery method according to the present invention is not limited to the outward direction for using centrifugal force and can be set in the rotation direction, the separated blood plasma component can be easily delivered.

Although the present invention has been fully described in conjunction with preferred embodiments thereof with reference to the accompanying drawings, various changes and modifications are possible for those skilled in the art. Therefore, such changes and modifications should be construed as included in the present invention unless they depart from the intention and scope of the invention as defined by the appended claims.

What is claimed is:

1. A liquid delivery method comprising:
    a first step for preparing a rotary substrate capable of rotating in at least a first rotation direction around a central axis of rotation, the rotary substrate being formed with a first chamber spatially closed, a second chamber spatially closed, and a fluid passage having a hydrophobic first fluid passage end portion connected to the first chamber and a second fluid passage end portion connected to the second chamber and connecting the first chamber with the second chamber, the first fluid passage end portion extending from the first chamber in the first rotation direction of the rotary substrate;
    a second step for accommodating a liquid in the first chamber;
    a third step for rotating the rotary substrate about the central axis of rotation at an acceleration a1 directed to the same direction as the first rotation direction until a rotation velocity of the rotary substrate reaches at a predetermined rotation velocity RV1, resulting in that a centrifugal force directed to a radial direction r orthogonal to the first rotation direction acts on the liquid, but a capillary force due to the hydrophobicity of the first fluid passage end portion holds the liquid in the first chamber; and
    a fourth step for abruptly breaking the rotation of the rotary substrate at the rotary velocity RV1 by an acceleration a2 directed to an opposite direction with the first rotation direction and having an absolute value larger than that of the acceleration a1, thereby generating an inertial force exceeding the capillary force and oriented in the first rotation direction on the liquid in the first chamber, the inertial force causing the liquid to flow from the first chamber through the first fluid passage end portion and the fluid passage into the second chamber.

2. The liquid delivery method according to claim 1, wherein the rotary substrate is formed with an application port for communicating the first chamber with an outside of the rotary substrate, and
    wherein the liquid is applied to the first chamber through the application port during the second step.

3. The liquid delivery method according to claim 1, wherein the fluid passage rather than the first fluid passage end portion is hydrophilic.

4. The liquid delivery method according to claim 1, further comprising a fifth step for maintaining the rotation of the rotary substrate at the rotation velocity RV1 between the third step and the fourth step.

5. The liquid delivery method according to claim 1, wherein the third step and the fourth step are repeated.

6. The liquid delivery method according to claim 5, further comprising a sixth step for halting the rotary substrate before the repetition of the third step subsequent to the fourth step.

7. A liquid delivery method comprising:
    a first step for preparing a rotary substrate capable of rotating in at least a first rotation direction about a central axis of rotation, the rotary substrate being formed with a first chamber spatially closed, a second chamber spatially closed, and a fluid passage having a hydrophobic first fluid passage end portion connected to the first chamber and a hydrophobic second fluid passage end portion connected to the second chamber and connecting the first chamber with the second chamber, the first fluid passage end portion extending from the first chamber in the first rotation direction of the rotary substrate;
    a second step for accommodating a liquid in the first chamber;
    a third step for holding the liquid in the first chamber by a capillary force due to hydrophobicity of the first fluid passage end portion;
    a fourth step for rapidly rotating the rotary substrate until a rotation velocity of the rotary substrate reaches at a predetermined rotation velocity RV2 by an acceleration b1 directed to an opposite direction with the first rotation direction, thereby generating an inertial force exceeding the capillary force and directed to the first rotation direction on the liquid so that the liquid flows from the first chamber through the first fluid passage end portion and the fluid passage into the second chamber.

8. The liquid delivery method according to claim 7, wherein the rotary substrate is formed with an application port for communicating the first chamber with an outside of the rotary substrate, and
    wherein the liquid is applied to the first chamber through the application port during the second step.

9. The liquid delivery method according to claim 7, wherein the first fluid passage rather than the first fluid passage end portion and the second fluid passage end portion is hydrophilic.

10. The liquid delivery method according to claim 7, further comprising a fifth step for decelerating the rotation of the rotary substrate around the central axis of rotation at an acceleration b2 directed to the same direction as the first rotation direction and having an absolute value smaller than that of the acceleration b1 after the fourth step.

11. The liquid delivery method according to claim 7, further comprising a sixth step for maintaining the rotation of the rotary substrate at the rotary velocity RV2 between the fourth step and the fifth step.

12. The liquid delivery method according to claim 11, further comprising a seventh step for halting the rotary substrate before the repetition of the fourth step subsequent to the fifth step.

13. The liquid delivery method according to claim 7, wherein the fourth step and the fifth step are repeated.

* * * * *

UNITED STATES PATENT AND TRADEMARK OFFICE
CERTIFICATE OF CORRECTION

| | |
|---|---|
| PATENT NO. | : 7,497,996 B2 |
| APPLICATION NO. | : 11/516008 |
| DATED | : March 3, 2009 |
| INVENTOR(S) | : Nobuhiko Ozaki et al. |

It is certified that error appears in the above-identified patent and that said Letters Patent is hereby corrected as shown below:

On the title page Item "(56) References Cited", under "FOREIGN PATENT DOCUMENTS", change "EP   0 629 580 A2   5/1990" to --EP   0 629 850 A2   5/1990--.

Signed and Sealed this

Thirtieth Day of June, 2009

JOHN DOLL
*Acting Director of the United States Patent and Trademark Office*